(12) United States Patent
Lu et al.

(10) Patent No.: US 11,530,234 B2
(45) Date of Patent: *Dec. 20, 2022

(54) CD73 INHIBITORS AND PHARMACEUTICAL USES THEREOF

(71) Applicant: RISEN (SUZHOU) PHARMA TECH CO., LTD., Jiangsu (CN)

(72) Inventors: Jiasheng Lu, Shanghai (CN); Jiamin Gu, Suzhou (CN); Gang Chen, Suzhou (CN); Feng Zhou, Suzhou (CN); Qiguo Zhang, Suzhou (CN); Xuli Wang, Suzhou (CN); Xiang Ji, Suzhou (CN); Lin Wang, Suzhou (CN); Xianqi Kong, Dollard-des-Ormeaux (CA)

(73) Assignee: RISEN (SUZHOU) PHARMA TECH CO., LTD., Suzhou (CN)

(*) Notice: Subject to any disclaimer, the term of this patent is extended or adjusted under 35 U.S.C. 154(b) by 50 days.

This patent is subject to a terminal disclaimer.

(21) Appl. No.: 17/133,348

(22) Filed: Dec. 23, 2020

(65) Prior Publication Data

US 2021/0139526 A1      May 13, 2021

Related U.S. Application Data

(63) Continuation-in-part of application No. 16/566,327, filed on Sep. 10, 2019, now Pat. No. 10,881,681.

(60) Provisional application No. 62/773,267, filed on Nov. 30, 2018.

(30) Foreign Application Priority Data

Sep. 11, 2018   (CN) .................. 201811057145.X

(51) Int. Cl.
| | | |
|---|---|---|
| *C07H 19/20* | (2006.01) | |
| *A61P 35/00* | (2006.01) | |
| *C07H 19/23* | (2006.01) | |
| *A61K 31/7076* | (2006.01) | |
| *A61K 39/395* | (2006.01) | |
| *A61K 39/00* | (2006.01) | |

(52) U.S. Cl.
CPC ......... *C07H 19/20* (2013.01); *A61K 31/7076* (2013.01); *A61K 39/3955* (2013.01); *C07H 19/23* (2013.01); *A61K 2039/505* (2013.01); *A61K 2039/545* (2013.01)

(58) Field of Classification Search
None
See application file for complete search history.

(56) References Cited

U.S. PATENT DOCUMENTS

| | | |
|---|---|---|
| 5,817,641 A | 10/1998 | Waldman et al. |
| 6,881,725 B2 | 4/2005 | Yerxa et al. |
| 7,018,985 B1 | 3/2006 | Boyer et al. |
| 7,109,181 B2 | 9/2006 | Cowlen et al. |
| 7,115,585 B2 | 10/2006 | Yerxa et al. |
| 7,435,724 B2 | 10/2008 | Douglas et al. |
| 7,851,456 B2 | 12/2010 | Boyer et al. |
| 9,505,796 B2 | 11/2016 | Schrader et al. |
| 10,881,681 B2 * | 1/2021 | Lu ................. A61K 31/7076 |
| 2013/0109645 A1 | 5/2013 | Gahl et al. |
| 2017/0044203 A1 | 2/2017 | Cacatian et al. |
| 2017/0267710 A1 | 9/2017 | Debien et al. |
| 2018/0030453 A1 | 2/2018 | Zakharenko et al. |
| 2018/0072742 A1 | 3/2018 | Chen et al. |

FOREIGN PATENT DOCUMENTS

| | | |
|---|---|---|
| CA | 3009196 A1 | 7/2017 |
| ES | 2469290 B2 | 1/2015 |
| FR | 3011240 A1 | 4/2015 |
| JP | 2019535720 A | 12/2019 |
| WO | 2006038865 | 4/2006 |
| WO | 2015164573 A1 | 10/2015 |
| WO | 2017098421 A1 | 6/2017 |

(Continued)

OTHER PUBLICATIONS

Bhattarai, S. et al., "α-β-Methylene-ADP (AOPCP) Derivatives and Analogues: Development of Potent and Selective ecto-5'-Nucleotidase (CD73) Inhibitors", J. Med. Chem. 2015, 58(15), 6248-6263.

Zhou et al., "Phloroglucinol induces apoptosis via apoptotic signaling pathways in HT-29 colon cancer cells", Oncol Rep. 32 (2014): 1341-1346.

Stagg and Smyth, "Extracellular adenosine triphosphate and adenosine in cancer", Oncogene, 29 (2010): 5346-5358.

M. Al-Rashida et al., "2-Alkoxy-3-(sulfonylarylaminomethylene)-chroman-4-ones as potent and selective inhibitors of ectonucleotidases", Eur. J. Med. Chem., 115 (2016): 484-494.

(Continued)

*Primary Examiner* — Traviss C Mcintosh, III
(74) *Attorney, Agent, or Firm* — BCF LLP

(57) ABSTRACT

CD73 (also known as ecto-5'-nucleotidase) inhibitor compounds are provided, as well as compositions and uses thereof for treating or preventing CD73-associated or related diseases, disorders and conditions, including cancer- and immune-related disorders. CD73 inhibitor compounds include compounds having the structure set forth in Formula I and pharmaceutically acceptable esters or salts thereof.

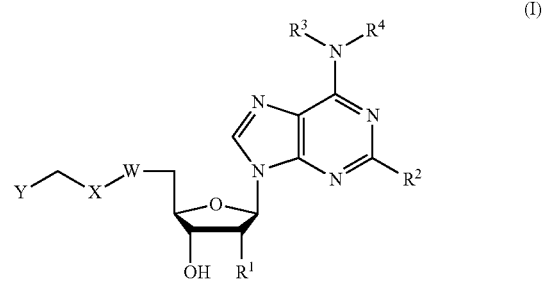

21 Claims, 1 Drawing Sheet

(56) References Cited

FOREIGN PATENT DOCUMENTS

| WO | 2017120508 A1 | 7/2017 |
| WO | 2018049145 A1 | 3/2018 |
| WO | 2018094148 A1 | 5/2018 |
| WO | 2019173682 A1 | 9/2019 |
| WO | 2020051686 A1 | 3/2020 |

OTHER PUBLICATIONS

M.H. Kazemi et al., "Adenosine and Adenosine Receptors in the Immunipathogenesis and Treatment of Cancer", J. Cell. Physiol., 233 (2018): 2032-2057.

Stagg, J. et al., "Anti-CD73 Antibody Therapy Inhibits Breast Tumor Growth and Metastasis", Proc. Natl. Acad. Sci. USA.: 107 (2010): 1547-1552.

Stagg, J. et al., "CD73-Deficient Mice Have Increased Antitumor Immunity and Are Resistant to Experimental Metastasis", Cancer Res. 71 (2011): 2892-2900.

Y.-P. Gong et al., "Evaluation of WO2017098421: GSK's benzothiazine compounds as CD73 inhibitor filings", Expert Opin. Ther. Pat., 28 (2018): 167-171.

Whiteside, T.L., "Targeting adenosine in cancer immunotherapy: a review of recent progress", Expert Rev. Anticancer Ther., 17 (2017): 527-535.

\* cited by examiner

CD73 INHIBITORS AND PHARMACEUTICAL USES THEREOF

CROSS-REFERENCE TO RELATED APPLICATIONS

This application is a continuation-in-part of U.S. patent application Ser. No. 16/566,327, filed Sep. 10, 2019, which claims the benefit of priority from U.S. Provisional Application No. 62/773,267, filed Nov. 30, 2018, and Chinese Patent Application No. 201811057145.X, filed Sep. 11, 2018, each of which is hereby incorporated by reference in its entirety. This application also claims the benefit of priority from Chinese Patent Application No. 202011346141.0, filed Nov. 25, 2020, which is hereby incorporated by reference in its entirety.

FIELD

The present disclosure relates to compounds and compositions that inhibit CD73 (ecto-5'-nucleotidase), and uses thereof for treating and/or preventing CD73-associated or related diseases, disorders and conditions, including cancer- and immune-related disorders.

BACKGROUND

Ecto-nucleotidases are a group of cell-surface located ecto-enzymes. The members of the ecto-nucleotidase family include ecto-nucleotide pyrophosphatase/phosphodiesterases (E-NPPs), ecto-nucleoside triphosphate diphosphohydrolases (E-NTPDases), ecto-5'-nucleotidase (e5NT, also known as CD73) and alkaline phosphatase (AP). These enzymes hydrolyze a variety of extracellular nucleotides to nucleosides including adenosine. Extracellular nucleotides are important signaling molecules that trigger cellular responses by acting on their respective receptors (for example, adenosine activates P1 receptors, and nucleotides thereof (ADP, ATP) activate P2 receptors). Adenosine 5'-monophosphate (AMP) is a major substrate of CD73 that is hydrolyzed to adenosine. Adenosine is ubiquitously present in the body and is an important regulator of purinergic cell signaling that is vital for many physiological and pathophysiological processes.

There is a wealth of data implicating CD73 enzymatic activity in promotion and metastasis of cancer. CD73 is up-regulated in many cancer cell-types and tumors, and its expression has been shown to be associated with tumor neovascularization, invasiveness and metastasis. The hydrolytic cascade from extracellular ATP to adenosine is an important immunosuppressive regulatory pathway in the tumor microenvironment. CD73 overexpression impairs adaptive antitumor immune responses, and enhances tumor growth and metastasis. Extracellular adenosine is also implicated in regulating adaptive responses to hypoxia. Decreasing e5NT activity with monoclonal antibodies, siRNA, and small molecule inhibitors including AMPCP (adenosine [(α,β)-methylene] diphosphate) has been shown to attenuate the growth and metastasis of tumors (see, e.g., Zhou et al., *Oncol. Rep.* 17 (2007): 1341-1346; Stagg and Smyth, *Oncogene*, 29 (2010): 5346-5358). Tumor growth is also impaired in CD73-deficient mice and it has been established that these effects are largely mediated by diminished adenosine production in these mice. Inhibitors of CD73 have thus been actively explored for their therapeutic potential against cancer (see, e.g., M. al-Rashida et al., *Eur. J. Med. Chem.,* 115 (2016): 484-494, and references cited therein).

Tumor cells overcome anti-tumor responses in part through immunosuppressive mechanisms. There are several such immune modulatory mechanisms. Among them, adenosine is a key factor which can be generated by both cancer and immune cells in the tumor microenvironment to suppress anti-tumor responses. The generation of adenosine from adenosine triphosphate (ATP) is catalyzed by two cell-surface proteins, CD73 and CD39, and can be enhanced under metabolic stress, such as tumor hypoxic conditions. Adenosine exerts its immune-regulatory functions through four adenosine receptors (ARs), called A1, A2A, A2B, and A3, which are expressed on various immune cells. Overexpression of adenosine-generating enzymes such as CD73 and ARs has been correlated with tumor progression in a multitude of cancer types. Since the signaling of ARs enhances tumor progression, their modulation also represents a promising therapeutic approach for cancer (M. H. Kazemi, et al., *J. Cell. Physiol.,* 233 (2018): 2032-2057, and references cited therein).

As mentioned above, ecto-nucleotidases are cell surface-located enzymes that regulate purinergic (and pyrimidinergic) signaling pathways. There are four distinct families of ecto-nucleotidases: ecto-nucleoside triphosphate diphosphohydrolasea (CD39), ecto-nucleotide pyrophosphatases/phosphodiesterases, alkaline phosphatases, and ecto-5'-nucleotidase (e5NT, also known as CD73). CD73 is a glycophosphatidylinositol-anchored di-Zn metallophosphatase. CD73 catalyzes the dephosphorylation of extracellular adenosine monophosphate (AMP) to adenosine. This ecto-enzymatic cascade in tandem with CD39 generates adenosine from ATP. The CD73-catalyzed conversion of AMP to adenosine is considered to be a major contributor to the elevated levels of extracellular adenosine in the tumor microenvironment (Stagg, J. et al., *Proc. Natl. Acad. Sci. USA.:* 107 (2010): 1547-1552). Expression of CD73 is directly upregulated by the hypoxia-inducible factor-1α, which explains the observed increase in extracellular adenosine in hypoxic malignant tumors. CD73 is also expressed by T-regulatory cells (Tregs) and promotes Treg-mediated immunosuppression (Stagg J, et al., *Cancer Res.* 71 (2011): 2892-2900). In addition, CD73 is induced by transforming growth factor-β (TGF-β), tumor necrosis factor-α (TNF-α), hepatocyte growth factor (HGF), interleukin-6 (IL-6), mitogen-activated protein kinase (MAPK), signal transducers and activators of transcription 3 (STAT3), interleukin-2 (IL-2), retinoic acid, int/wingless (WNT), epithelial-to-mesenchymal transition, and p53 mutations. CD73 is overexpressed in a multitude of tumor types and promotes the invasion, migration, and adhesion of tumor cells. CD73 is also associated with immune tolerance and poor prognosis in cancer. CD73 is thus a promising target for the development of anti-cancer drugs. Furthermore, CD73 inhibitors have potential for the treatment of other diseases mediated by adenosine and its receptors (Y.-P. Gong, et al., *Expert Opin. Ther. Pat.,* 28 (2018): 167-171).

The adenosine pathway is also known to be a major immunosuppressive component of many human tumors (for review, see Whiteside, T. L., *Expert Rev. Anticancer Ther.,* 17 (2017): 527-535). Adenosine and inosine emerge as critical immune checkpoints in cancer. Cooperation of the adenosine and PGE2 pathways in the tumor microenvironment contributes to suppression of anti-tumor immune effector cells. Targeting of the adenosine pathway with pharmacologic inhibitors or antibodies is thus a promising therapeutic strategy in cancer.

Blocking activities of ecto-nucleotidases or of adenosine receptor signaling in preclinical in vivo studies has been successful in inhibiting tumor growth and metastasis. The adenosine pathway blockade alone or in combination with other immune therapies, including checkpoint inhibitors, is currently being implemented in initial phase I clinical trials for subjects with advanced malignancies.

Small-molecule inhibitors of CD73 have been reported. For example, Adams et al. (International PCT Application Publication No. WO2017/098421) describe substituted benzothiadiazine derivatives that are inhibitors of CD73, pharmaceutical compositions thereof, and their use in the treatment of cancer, pre-cancerous syndromes and diseases associated with CD73 inhibition.

Debien et al. (International PCT Application Publication No. WO2017/120508; U.S. Patent Application Publication No. US2017/0267710) describe compounds that modulate the conversion of AMP to adenosine by 5'-nucleotidase, ecto, compositions containing the compounds, methods for synthesizing the compounds, and the use of such compounds and compositions for the treatment and/or prevention of a diverse array of diseases that are mediated by 5'-nucleotidase, ecto.

Cacatian et al. (International PCT Application Publication No. WO2015/164573) describe purine derivatives and pharmaceutical compositions thereof which are inhibitors of CD73 and are useful in the treatment of cancer.

Chen et al. (International PCT Application Publication No. WO 2018/049145) disclose preparation of nucleotides as ectonucleotidase inhibitors, and the use of the compounds in treating or preventing cancer.

The contents of all documents and references cited herein are hereby incorporated by reference in their entirety.

SUMMARY

The present disclosure relates to compounds and compositions comprising the compounds that inhibit the activity of ecto-5'-nucleotidase (also known as e5NT, CD73, NT5E, and 5NT). Inhibition of CD73 enzymatic activity leads to inhibition or modulation of extracellular adenosine levels and thus modulates the physiological environment of cells and tissues.

The present disclosure also relates to the use of such compounds and compositions for the treatment and/or prevention of diseases, disorders and conditions mediated, in whole or in part, by CD73. CD73 inhibitors have been linked to the treatment of many disorders, including cancer, fibrosis, neurological and neurodegenerative disorders (e.g., depression and Parkinson's disease), cerebral and cardiac ischemic diseases, immune-related disorders, and disorders with an inflammatory component. In particular embodiments, the CD73 inhibitor compounds and compositions described herein can act to inhibit the immunosuppressive activity and/or the anti-inflammatory activity of CD73, and are useful as therapeutics or prophylactic therapies when such inhibition is desirable.

In a first broad aspect, there are provided compounds of Formula I and pharmaceutically acceptable salts or esters thereof.

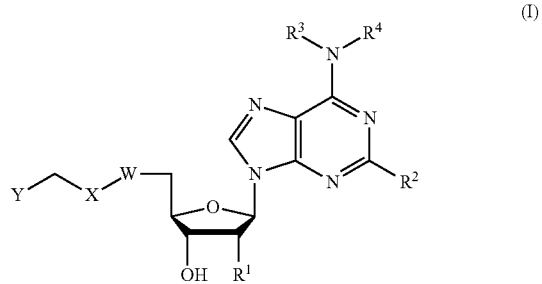

where W is oxygen, sulfur, nitrogen, or a methylene group; X is a moiety selected from phosphonyl (—P(=O)(OR)—), sulfonyl (—S(=O)$_2$—), and carbonyl (—C(=O)—) fragment, where R is hydrogen, ester-forming group, or protecting group; or X and W together form the —(CR$^7$R$^8$)$_n$—, where n is an integer from 0 to 3, and R$^7$ and R$^8$ are independently selected from a hydrogen, a halogen, a hydroxyl group and a lower alkyl group having 1 to 4 carbon atoms; Y is selected from phosphonate (—PO$_3$R$_2$), sulfonate (—SO$_3$R), and carboxylate (—CO$_2$R), where R is a hydrogen, an ester-forming group, or a protecting group; R$^1$ is a hydroxyl group or a hydrogen; R$^2$ is chlorine or a hydrogen; and R$^3$ and R$^4$ are independently selected from hydrogen, alkyl group, alkenyl group and alkynyl group, where at least one of R$^3$ and R$^4$ has a carbon number of from 1 to 30, such as without limitation from 1 to 10, from 11 to 20, from 11 to 30, or from 21 to 30, and wherein, when W is O or S, the carbon number is not 1 to 10 (i.e., when W is O or S, at least one of R$^3$ and R$^4$ has a carbon number of from 11 to 30).

In one embodiment, R$^3$, R$^4$, and the nitrogen atom to which they are attached form a heterocyclic system which is independently selected from a monocycle, a bicycle, a tricycle, a spiral-ring, a fused-ring, or a bridged-ring system.

In one embodiment, R$^3$ and R$^4$ are independently selected from hydrogen and a ring system, the ring system being a monocycle, bicycle, tricycle, spiral-ring, fused-ring or bridged-ring containing carbocyclic (aromatic or non-aromatic) or heterocyclic ring system, and the ring system being substituted or non-substituted, provided that R$^3$ and R$^4$ are not both hydrogen at the same time, and provided that the ring system is not a monocycle when W is O or S.

In a further embodiment, R$^3$ is hydrogen or a lower alkyl (e.g., C$_{1-6}$) and R$^4$ is —C(=O)R$^5$, —C(=O)NHR$^5$ or —C(=O)OR$^5$, where R$^5$ is a C$_{1-30}$ alkyl group, a C$_{2-30}$ alkenyl group or a C$_{2-30}$ alkynyl group, wherein the C$_{1-10}$ and C$_{2-10}$ groups are excluded when W is O or S (i.e., R$^5$ is a C$_{1-30}$ alkyl, C$_{1-30}$ alkenyl or C$_{11-30}$ alkynyl group when W is O or S).

In some embodiments, R$^3$ is hydrogen or a lower alkyl and R$^4$ is —C(=O)R$^5$, —C(=O)NHR$^5$ or —C(=O)OR$^5$, where R$^5$ is a ring system which is a monocycle, bicycle, tricycle, spiral-ring, fused-ring or bridged-ring containing a carbocyclic (aromatic or non-aromatic) or heterocyclic ring system, the carbocyclic or heterocyclic ring system being substituted or non-substituted, wherein the R$^5$ ring system is not a monocycle when W is O or S.

In one embodiment, there are provided compounds of Formula II and/or Formula III, and pharmaceutically acceptable salts or esters thereof:

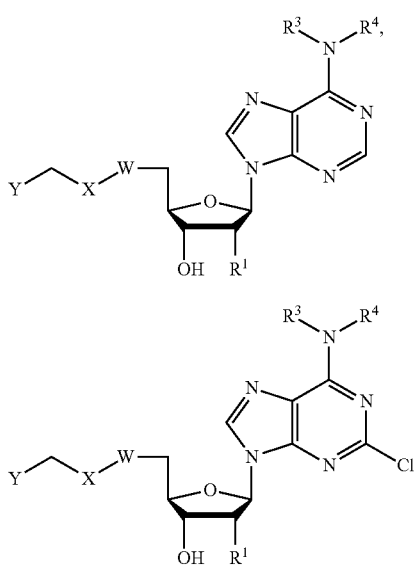

(II)

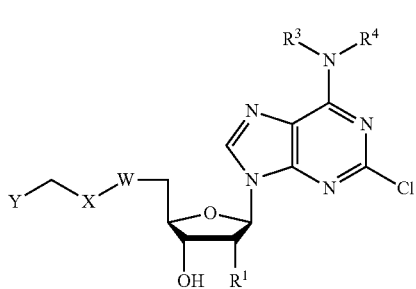

(III)

where W, X, Y, $R^1$, $R^3$, and $R^4$ are as defined above.

In another embodiment, there are provided compounds of Formula IV, and pharmaceutically acceptable salts or esters thereof:

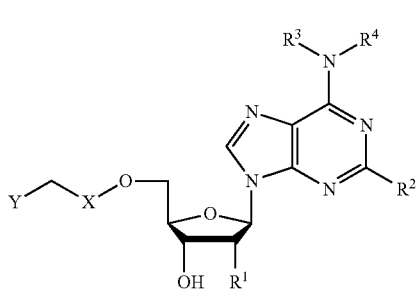

(IV)

where X, Y, $R^1$, $R^2$, $R^3$, and $R^4$ are as defined above.

In another embodiment, there are provided compounds of Formula IVa, and pharmaceutically acceptable salts or esters thereof:

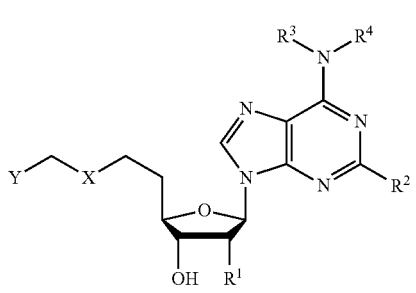

(IVa)

where X, Y, $R^1$, $R^2$, $R^3$, and $R^4$ are as defined above.

In another embodiment, there are provided compounds of Formula IVb, and pharmaceutically acceptable salts or esters thereof:

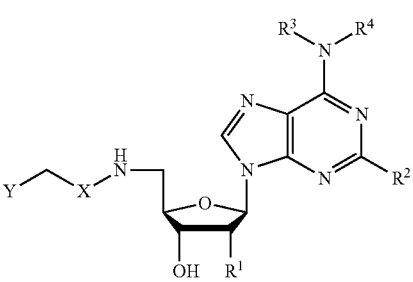

(IVb)

where X, Y, $R^1$, $R^2$, $R^3$, and $R^4$ are as defined above.

In another embodiment, there are provided compounds of Formula IVc, and pharmaceutically acceptable salts or esters thereof:

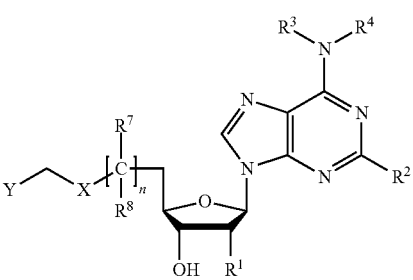

(IVc)

where n, X, Y, $R^1$, $R^2$, $R^3$, and $R^4$ are as defined above.

In yet another embodiment, there are provided compounds of Formulae V and/or VI, and pharmaceutically acceptable salts or esters thereof:

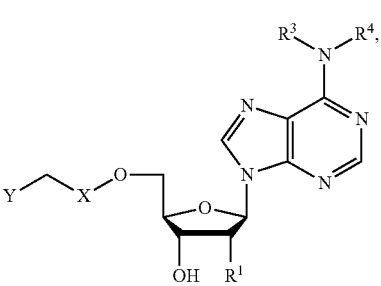

(V)

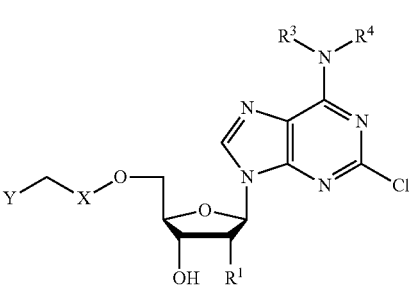

(VI)

where X, Y, $R^1$, $R^3$, and $R^4$ are as defined above.

In another embodiment, there are provided compounds of Formulae Va and/or VIa, and pharmaceutically acceptable salts or esters thereof:

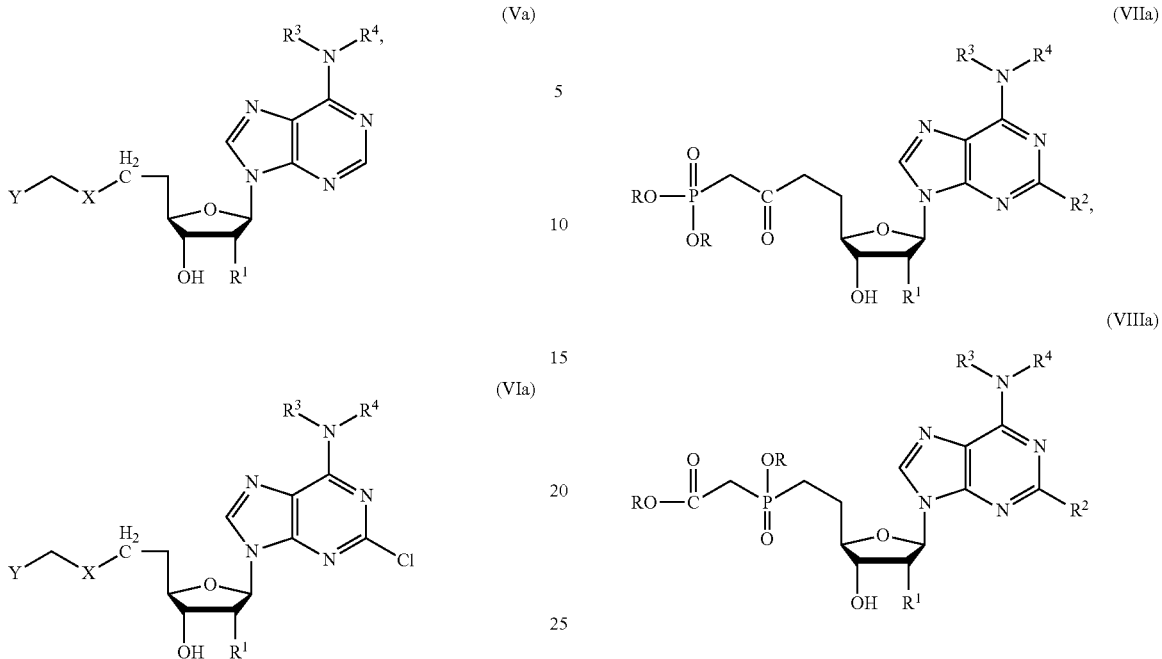

(Va)

(VIIa)

(VIa)

(VIIIa)

where R is hydrogen, an ester-forming group, or a protecting group; and $R^1$, $R^2$, $R^3$, and $R^4$ are as defined above.

where X, Y, $R^1$, $R^3$, and $R^4$ are as defined above.

In another embodiment, there are provided compounds of Formulae VII and/or VIII, and pharmaceutically acceptable salts or esters thereof:

In yet another embodiment, there are provided compounds of Formulae IX, and pharmaceutically acceptable salts or esters thereof:

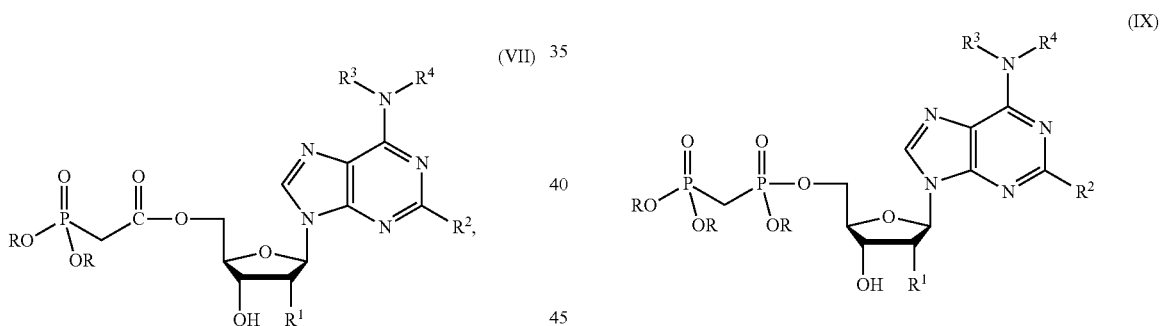

(VII)

(IX)

where R is hydrogen, an ester-forming group, or a protecting group; and $R^1$, $R^2$, $R^3$, and $R^4$ are as defined above.

In another embodiment, there are provided compounds of Formulae IXa, and pharmaceutically acceptable salts or esters thereof:

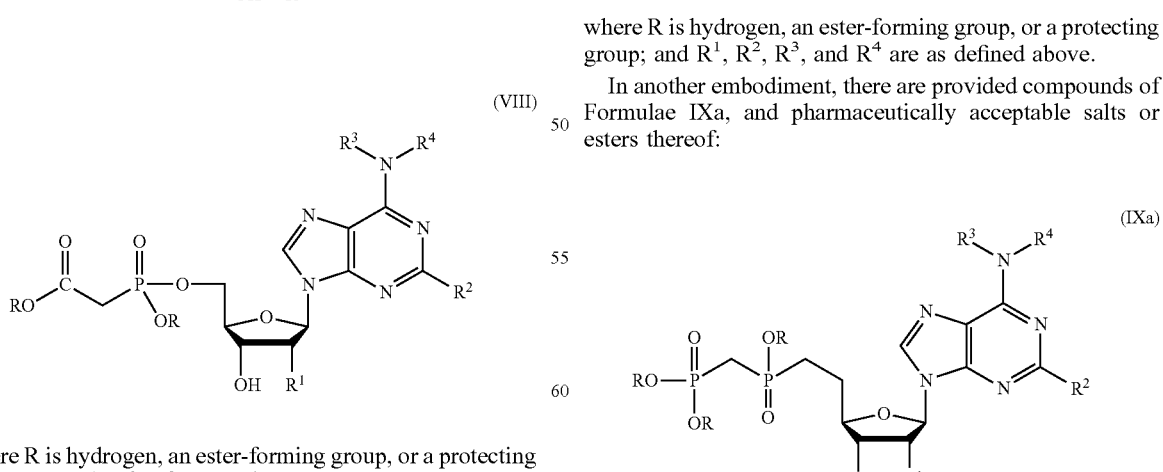

(VIII)

(IXa)

where R is hydrogen, an ester-forming group, or a protecting group; and $R^1$, $R^2$, $R^3$, and $R^4$ are as defined above.

In another embodiment, there are provided compounds of Formulae VIIa and/or VIIIa, and pharmaceutically acceptable salts or esters thereof:

where R is hydrogen, an ester-forming group, or a protecting group; and $R^1$, $R^2$, $R^3$, and $R^4$ are as defined above.

In one embodiment, $R^1$ is a hydroxyl group (i.e., the carbohydrate moiety in the compound is a D-ribosyl moiety). In another embodiment, $R^1$ is hydrogen (i.e., the carbohydrate moiety in the compound is a 2-deoxy-D-ribosyl moiety).

In another embodiment, $R^2$ is hydrogen. In yet another embodiment, $R^2$ is hydrogen and $R^1$ is a hydroxyl group (i.e., the compound is an adenosine derivative). In another embodiment, $R^2$ is hydrogen and $R^1$ is hydrogen (i.e., the compound is a deoxyadenosine derivative). In still another embodiment, $R^2$ is hydrogen and both $R^3$ and $R^4$ are not hydrogen (i.e., the compound is an adenosine derivative or a deoxyadenosine derivative with substituent groups on the amino group of the adenine moiety). In another embodiment, $R^2$ is chlorine and the compound is a 2-chloro-D-adenosine derivative or a 2-chloro-D-deoxyadenosine derivative.

In some embodiments, $R^3$ is hydrogen or a lower alkyl (e.g., $C_{1-6}$), and $R^4$ is an alkyl, alkenyl, or alkynyl group having 1 to 30 carbon atoms (i.e., a $C_{1-30}$ alkyl group, a $C_{2-30}$ alkenyl group, or a $C_{2-30}$ alkynyl group) and $R^4$ has 11 to 30 carbon atoms when W is O or S. In some embodiments, $R^3$ is a hydrogen or a lower alkyl, and $R^4$ is a group containing an adamantyl moiety. $R^4$ may be, for example, substituted or non-substituted 1-adamantyl, substituted or non-substituted 2-adamantyl, substituted or non-substituted 1-adamantylmethyl, substituted or non-substituted 1-adamantylethyl, substituted or non-substituted 1-adamantylpropyl, or substituted or non-substituted 1-adamantylbutyl. In some embodiments, $R^3$ is a hydrogen or a lower alkyl, and $R^4$ is a group containing a naphthyl moiety. $R^4$ may be, for example, substituted or non-substituted α-naphthyl, substituted or non-substituted β-naphthyl, substituted or non-substituted α-naphthylmethyl, substituted or non-substituted β-naphthylmethyl, substituted or non-substituted naphthylethyl, substituted or non-substituted naphthylpropyl, or substituted or non-substituted naphthylbutyl.

In another embodiment, $R^3$ is hydrogen or a lower alkyl, and $R^4$ is a substituent group containing a monocycle, bicyclic, tricyclic, or multicyclic ring system, where the ring system is fused, spiral, bridged, or parallel, and where the ring system is carbocyclic, aliphatic, aromatic, heterocyclic, or a combination thereof.

In a further embodiment, $R^3$ is hydrogen or a lower alkyl, and $R^4$ is —C(=O)$R^5$, —C(=O)NH$R^5$ or —C(=O)O$R^5$, where $R^5$ is an alkyl group or an alkenyl group or an alkynyl group having 1 to 30 carbon atoms, wherein $C_1$ to $C_{10}$ groups are excluded when W is O or S.

In some embodiments, $R^3$ is hydrogen or a lower alkyl, and $R^4$ is —C(=O)$R^5$, —C(=O)NH$R^5$ or —C(=O)O$R^5$, where $R^5$ is a substituent group containing a monocyclic, bicyclic, tricyclic, or multicyclic ring system, where the ring system is fused, spiral, bridged, or parallel, and where the ring system is carbocyclic, aliphatic, aromatic, heterocyclic, or a combination thereof, wherein R is not a monocyclic ring system when W is O or S.

In one embodiment, $R^4$ is a group containing an adamantyl moiety. In further embodiment, $R^4$ is a substituted or non-substituted 1-adamantyl or 2-adamantyl. In yet another embodiment, $R^4$ is a substituted or non-substituted 1-adamantylmethyl. In some embodiments, $R^4$ is 1-adamantylethyl, 1-adamantylpropyl, or 1-adamantylbutyl, where the adamantyl moiety can be substituted or non-substituted.

In another embodiment, $R^4$ is a group containing naphthyl moiety. In further embodiment, $R^4$ is substituted or non-substituted α-naphthy or β-naphthyl. In other embodiment, $R^4$ is α-naphthylmethyl or β-naphthylmethyl, without or with further substitution. In yet another embodiment, $R^4$ is selected from naphthylethyl, naphthylpropyl, and naphthylbutyl, where the naphthyl moiety can be non-substituted or substituted.

In another embodiment, $R^3$ and $R^4$, together with the nitrogen to which they are attached, form a tricyclic fused ring system, such as without limitation a substituted or unsubstituted carbazolyl moiety.

In another embodiment, $R^3$ and $R^4$, together with the nitrogen to which they are attached, form a heterocyclic system independently selected from monocycle, bicycle, tricycle, spiral-ring, fused-ring, and bridged-ring.

In some embodiments, there are provided compounds of Table 1 and pharmaceutically acceptable salts or esters thereof.

TABLE 1

Structures of example compounds.

| Compound No. | Structure |
|---|---|
| 1 | (structure shown) |

TABLE 1-continued
Structures of example compounds.
| Compound No. | Structure |
|---|---|
| 2 | 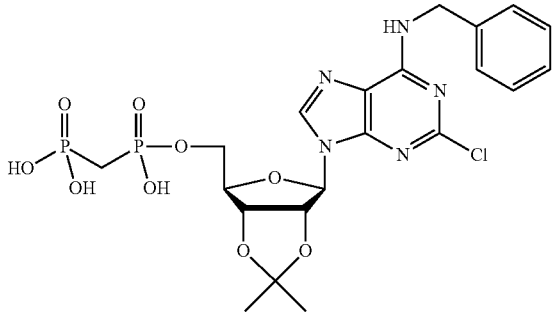 |
| 3 | 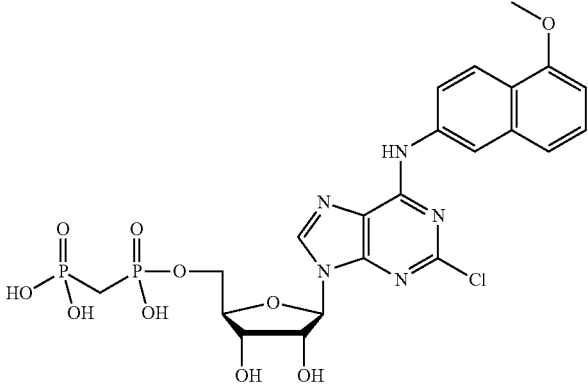 |
| 4 | 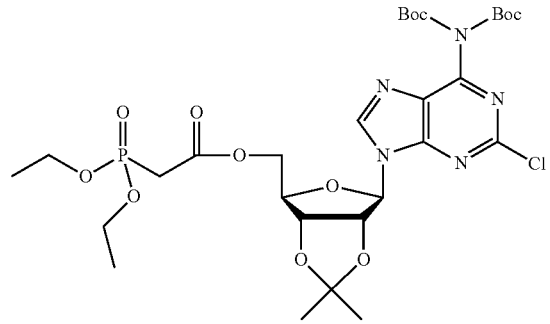 |
| 5 | 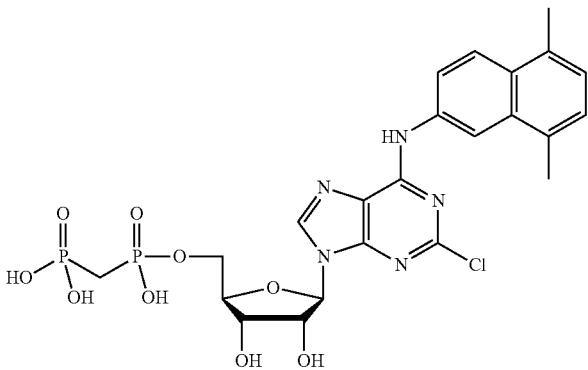 |

TABLE 1-continued
Structures of example compounds.
| Compound No. | Structure |
|---|---|
| 6 | 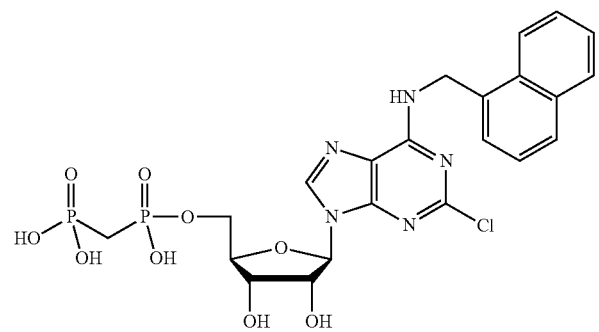 |
| 7 | 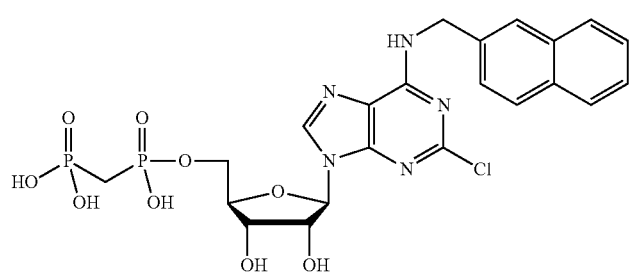 |
| 8 | 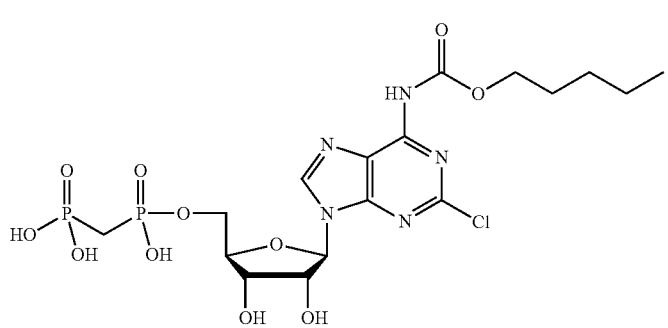 |
| 9 | 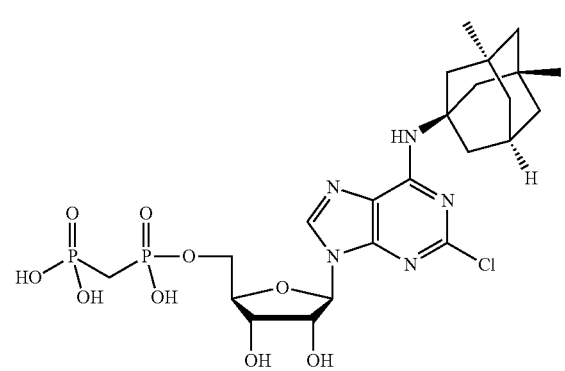 |

TABLE 1-continued
Structures of example compounds.
| Compound No. | Structure |
|---|---|
| 10 | 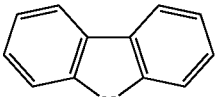 |
| 11 | 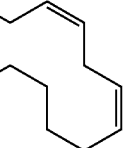 |
| 12 | 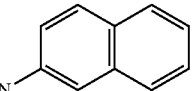 |
| 13 | 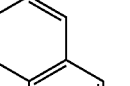 |

TABLE 1-continued

Structures of example compounds.

| Compound No. | Structure |
|---|---|
| 14 | (structure: bisphosphonate-ribose-2-chloro-N6-(1H-indol-2-yl)adenine) |
| 15 | (structure: bisphosphonate-ribose-2-chloro-N6-(dodecyloxycarbonyl)adenine) |
| 16 | (structure: bisphosphonate-ribose-2-chloro-N6-(adamantan-1-ylacetyl)adenine) |
| 17 | (structure: bisphosphonate-ribose-2-chloro-N6-(adamantan-2-yl)adenine) |

TABLE 1-continued
Structures of example compounds.
| Compound No. | Structure |
|---|---|
| 18 | 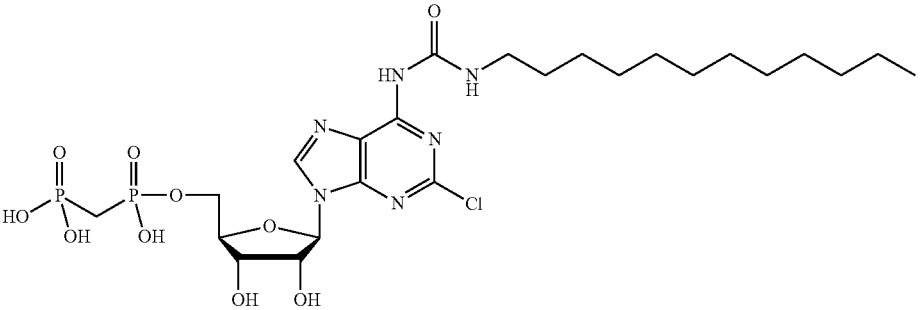 |
| 19 | 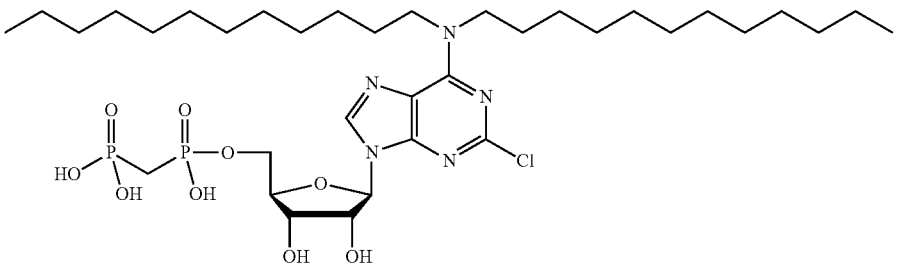 |
| 20 | 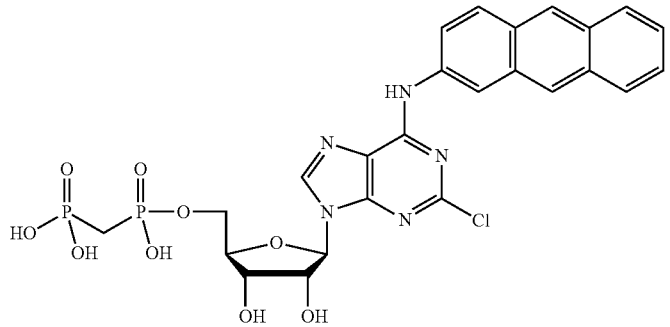 |
| 21 | 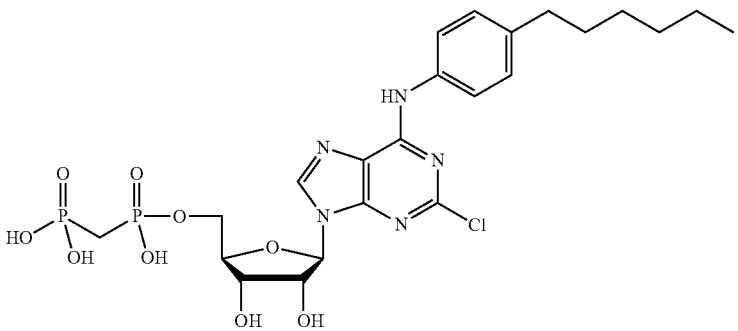 |

TABLE 1-continued
Structures of example compounds.
| Compound No. | Structure |
|---|---|
| 22 | 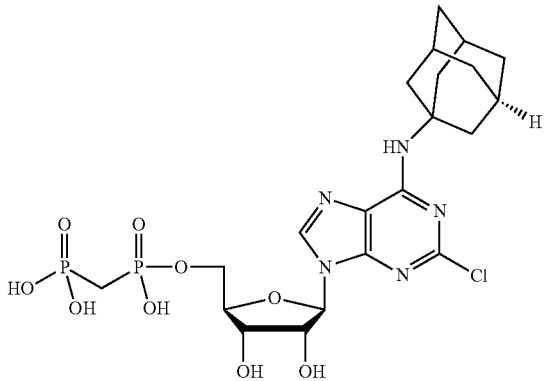 |
| 23 | 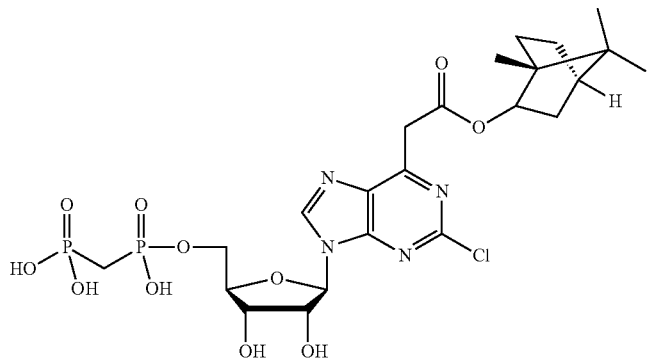 |
| 24 | 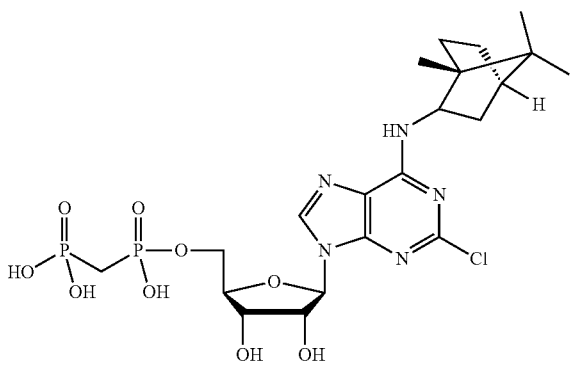 |
| 25 | 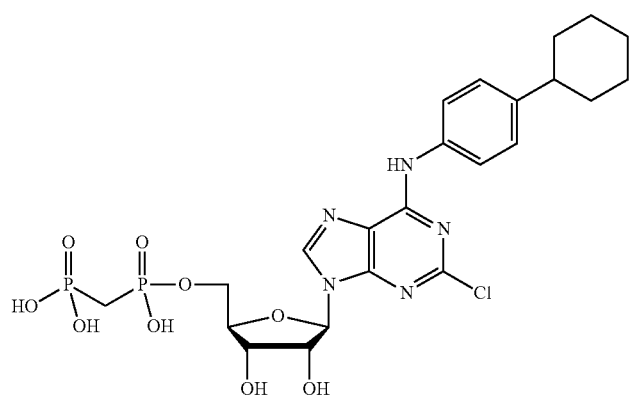 |

TABLE 1-continued
Structures of example compounds.
| Compound No. | Structure |
|---|---|
| 26 | 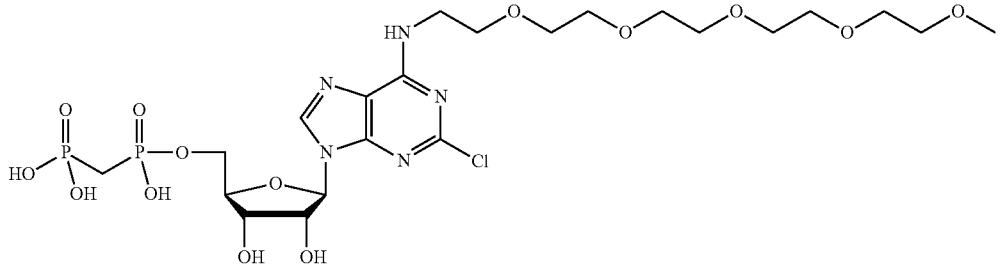 |
| 27 | 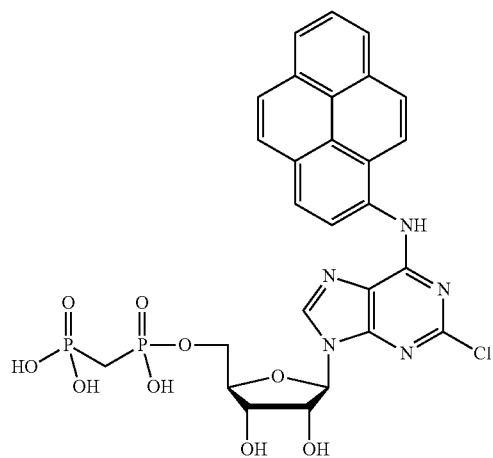 |
| 28 | 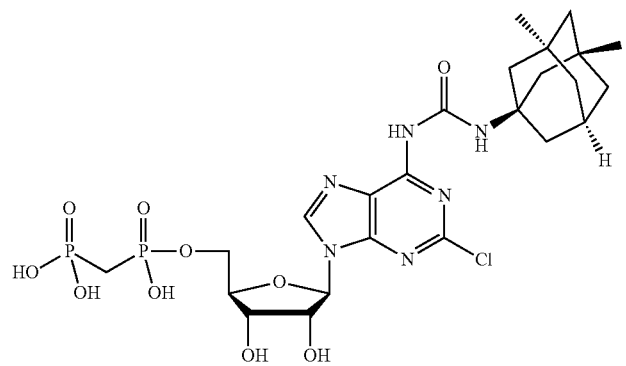 |
| 29 | 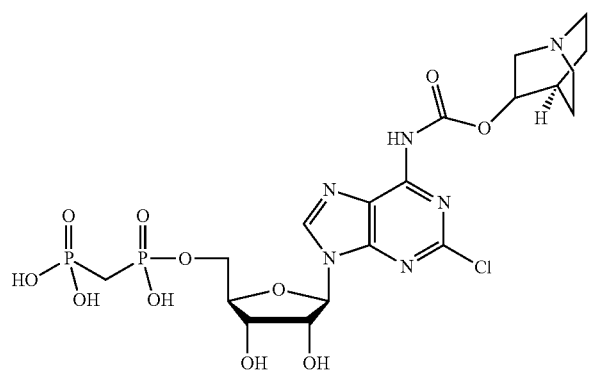 |

TABLE 1-continued

Structures of example compounds.

| Compound No. | Structure |
|---|---|
| 30 | 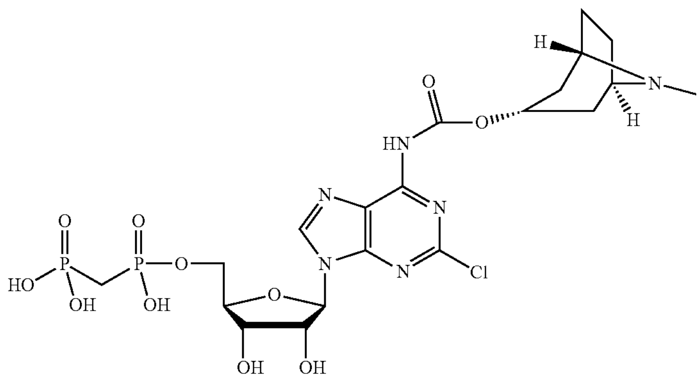 |
| 31 | 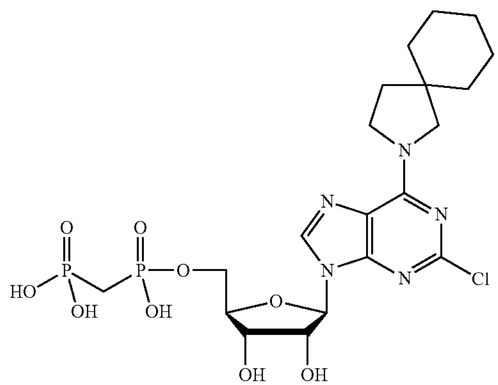 |
| 32 | 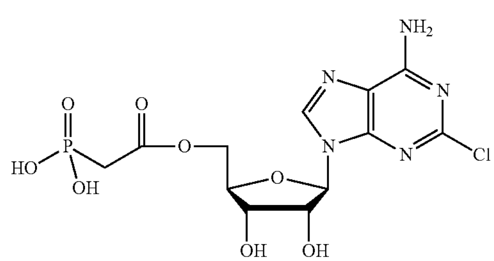 |
| 33 | 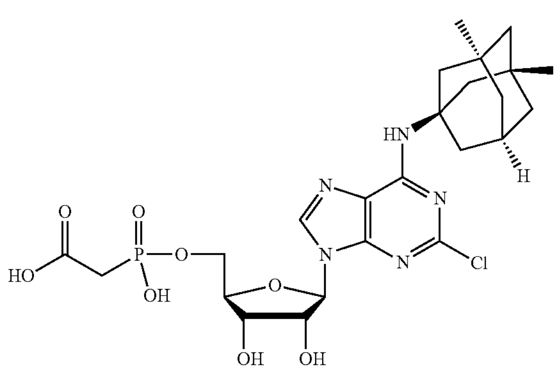 |

TABLE 1-continued
Structures of example compounds.
| Compound No. | Structure |
|---|---|
| 34 | 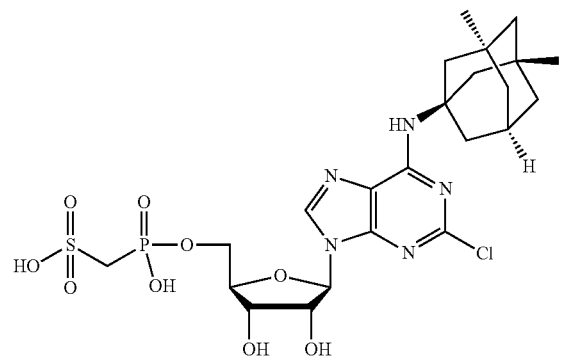 |
| 35 | 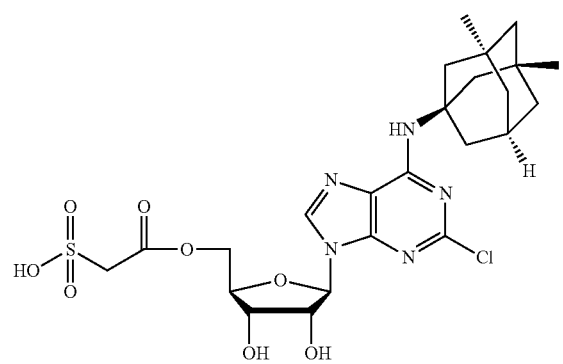 |
| 36 | 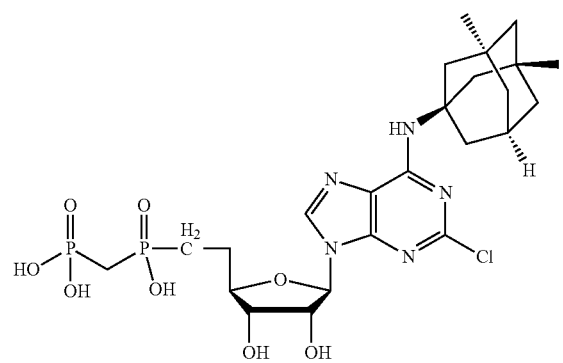 |
| 37 | 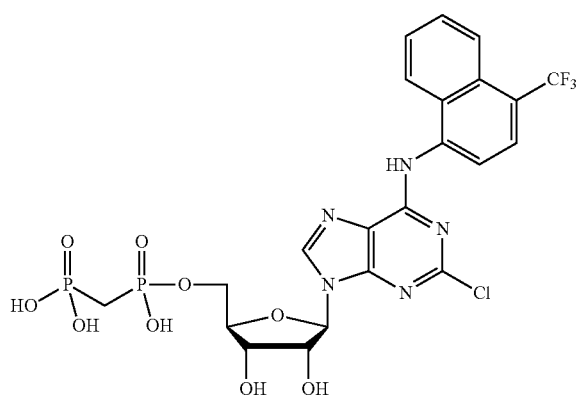 |

TABLE 1-continued
Structures of example compounds.
| Compound No. | Structure |
|---|---|
| 38 | 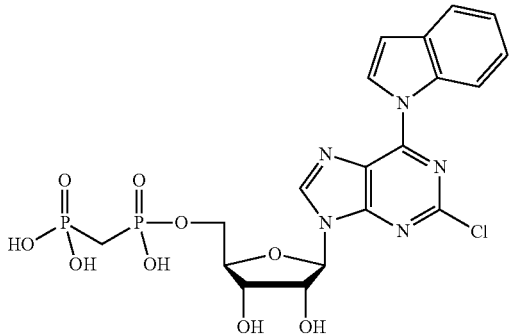 |
| 39 | 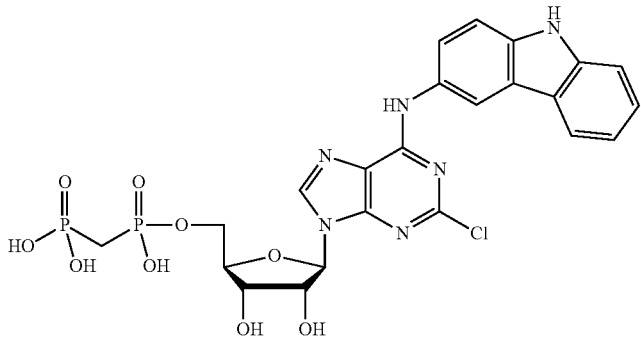 |
| 40 | 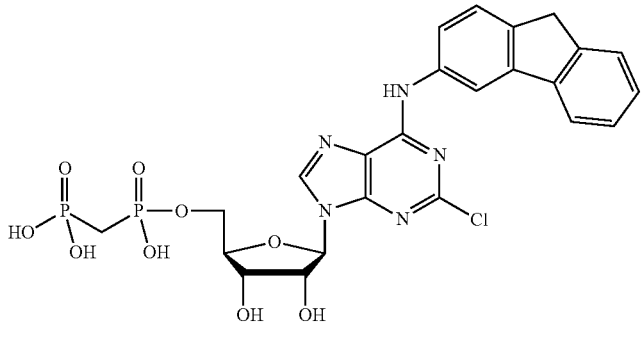 |
| 41 | 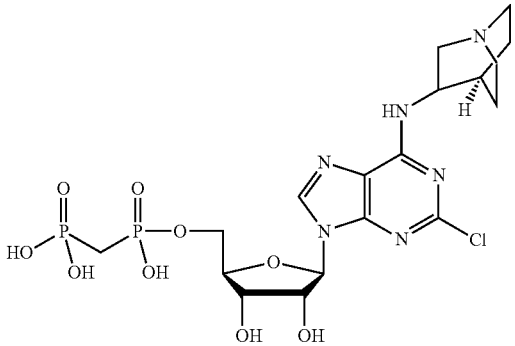 |

TABLE 1-continued
Structures of example compounds.
| Compound No. | Structure |
|---|---|
| 42 | 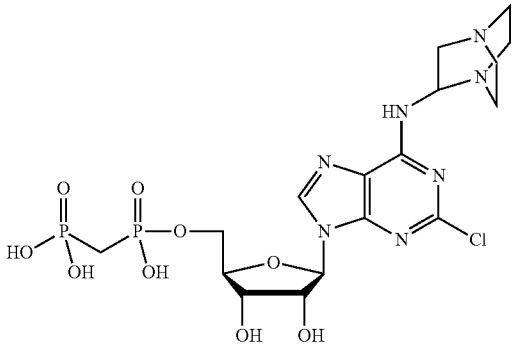 |
| 43 | 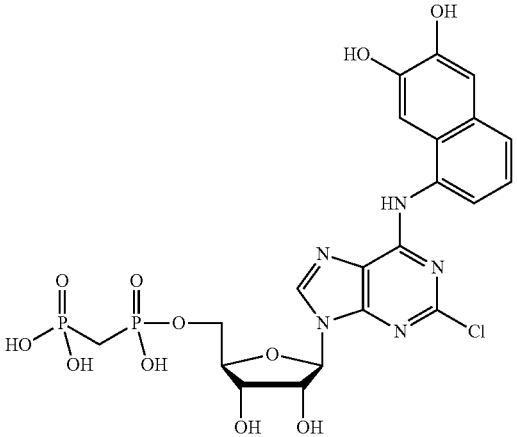 |
| 44 | 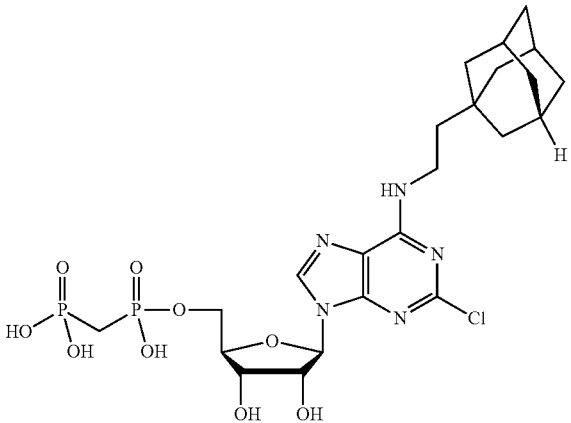 |

TABLE 1-continued

Structures of example compounds.

| Compound No. | Structure |
|---|---|
| 45 | 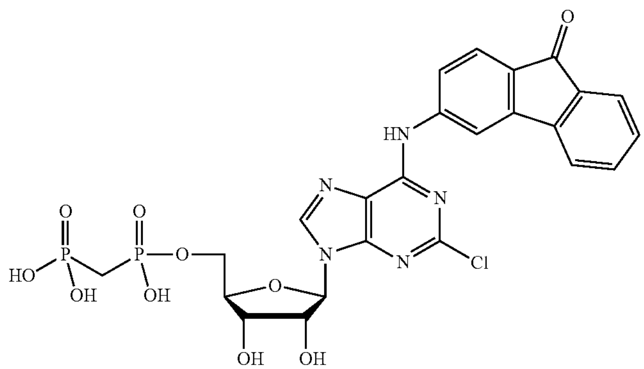 |
| 46 | 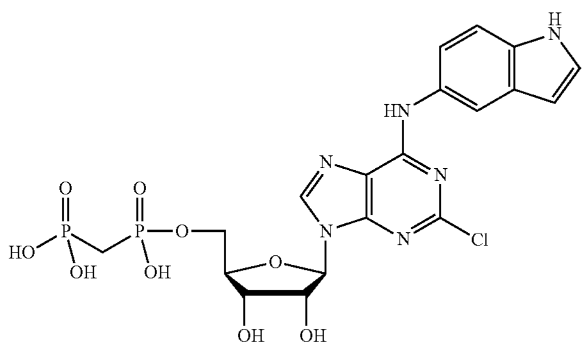 |
| 47 | 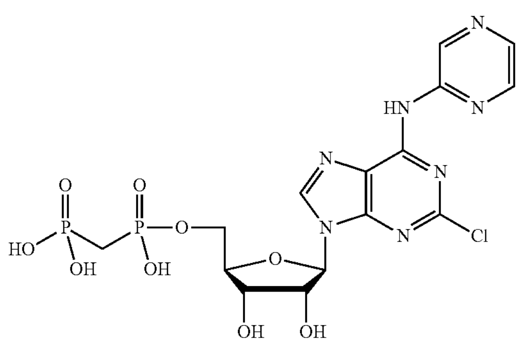 |
| 48 | 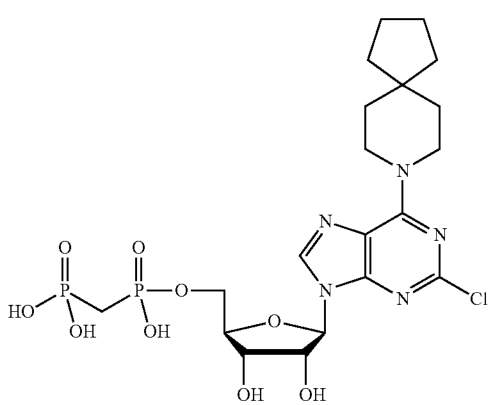 |

TABLE 1-continued
Structures of example compounds.
| Compound No. | Structure |
|---|---|
| 49 | 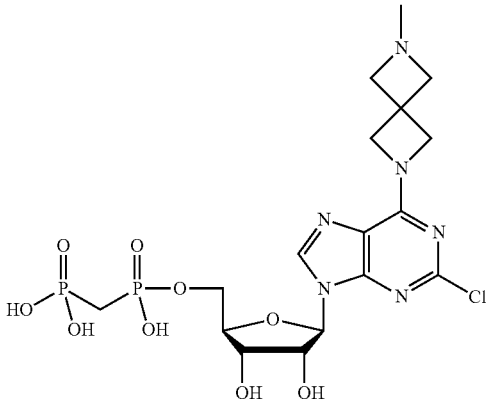 |
| 50 | 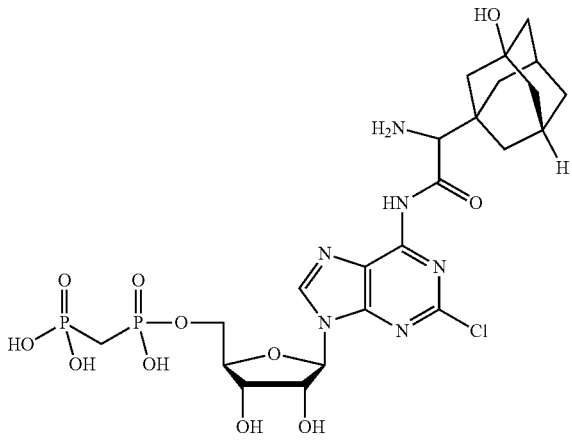 |
| 51 | 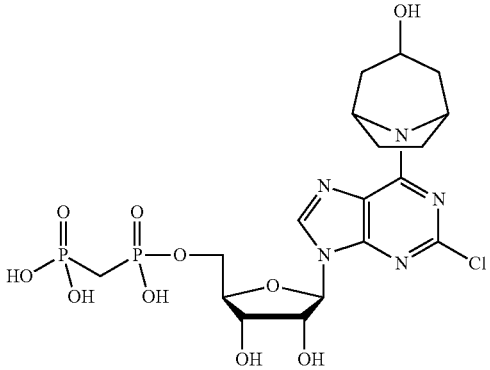 |

TABLE 1-continued
Structures of example compounds.
| Compound No. | Structure |
|---|---|
| 52 | 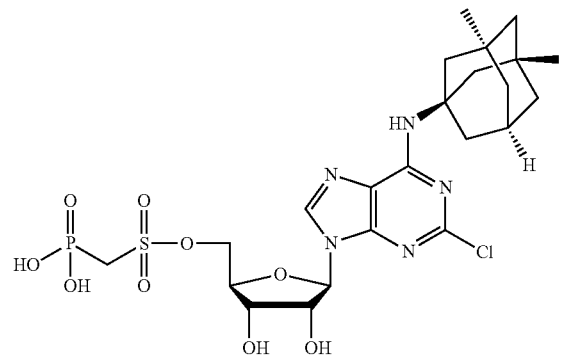 |
In some embodiments, there are provided compounds of Table 1a and pharmaceutically acceptable salts or esters thereof.
TABLE 1a
Structures of example compounds.
| Compound Number | Structure |
|---|---|
| a-1 | 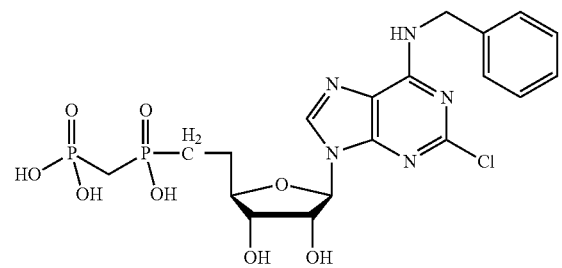 |
| a-2 | 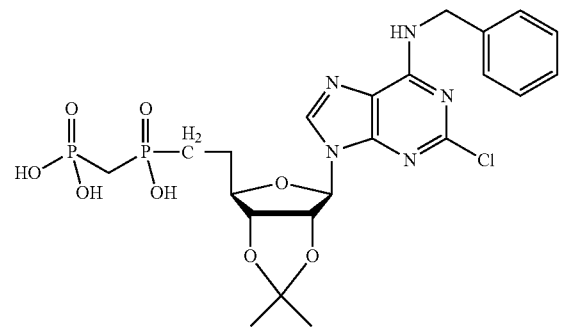 |

TABLE 1a-continued
Structures of example compounds.
| Compound Number | Structure |
|---|---|
| a-3 | 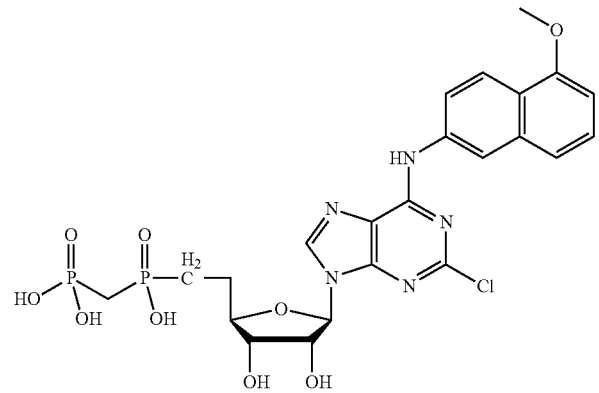 |
| a-4 | 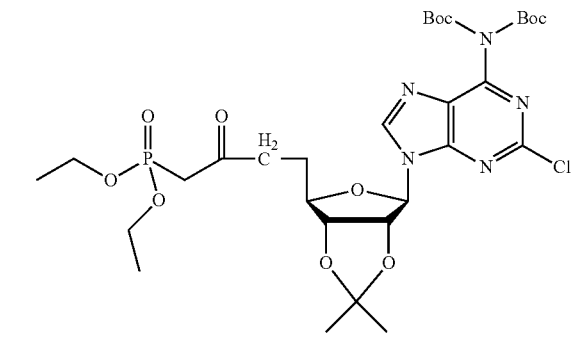 |
| a-5 | 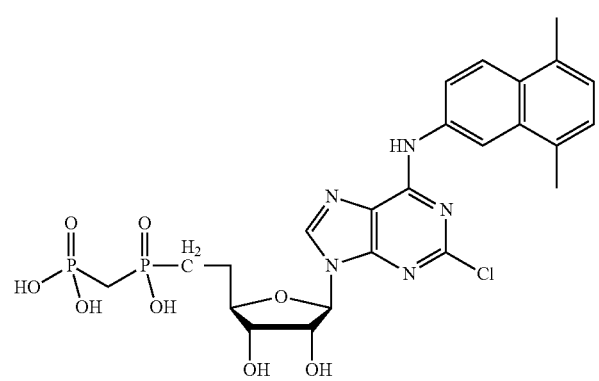 |
| a-6 | 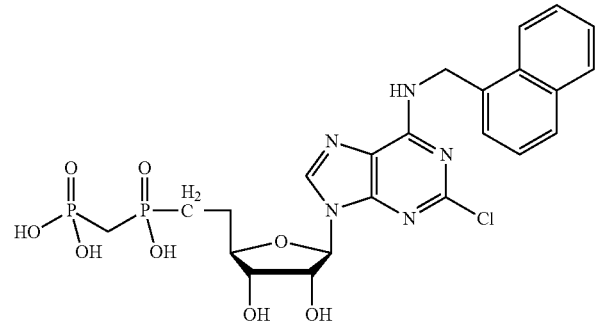 |

TABLE 1a-continued

Structures of example compounds.

| Compound Number | Structure |
|---|---|
| a-7 | (structure: 6-(naphthalen-2-ylmethylamino)-2-chloro-purine ribose with methylenebisphosphonate at 5') |
| a-8 | (structure: 6-(pentyloxycarbonylamino)-2-chloro-purine ribose with methylenebisphosphonate at 5') |
| a-9 | (structure: 6-(dimethyladamantylamino)-2-chloro-purine ribose with methylenebisphosphonate at 5') |
| a-10 | (structure: 6-(carbazol-9-yl)-2-chloro-purine ribose with methylenebisphosphonate at 5') |

TABLE 1a-continued
Structures of example compounds.
| Compound Number | Structure |
|---|---|
| a-11 | 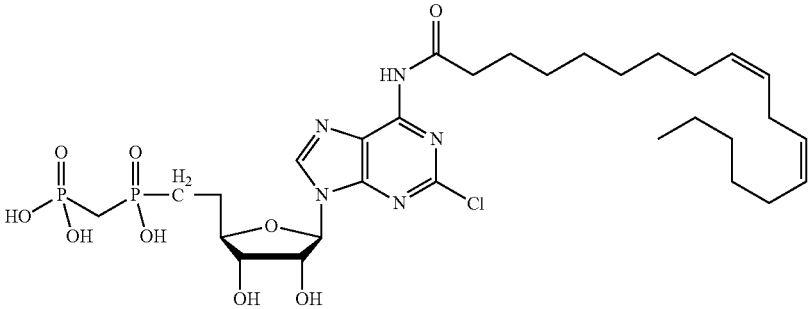 |
| a-12 | 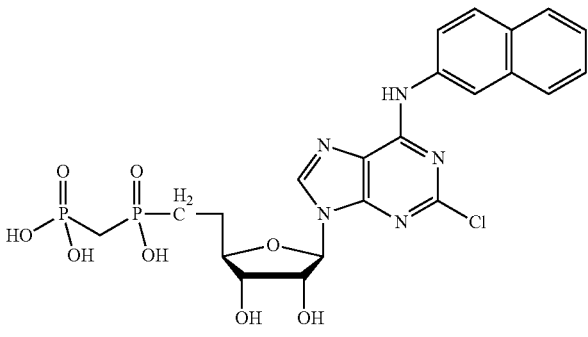 |
| a-13 | 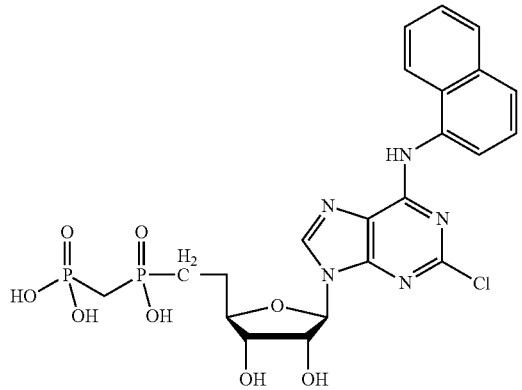 |
| a-14 | 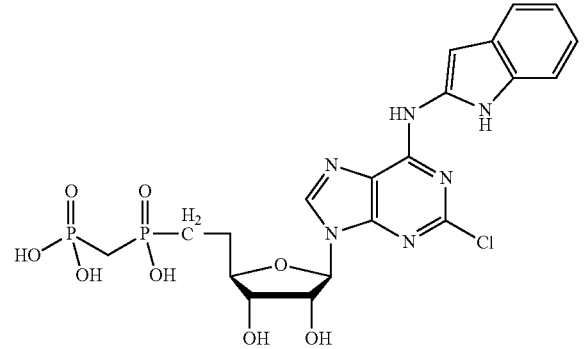 |

TABLE 1a-continued

Structures of example compounds.

| Compound Number | Structure |
| --- | --- |
| a-15 | 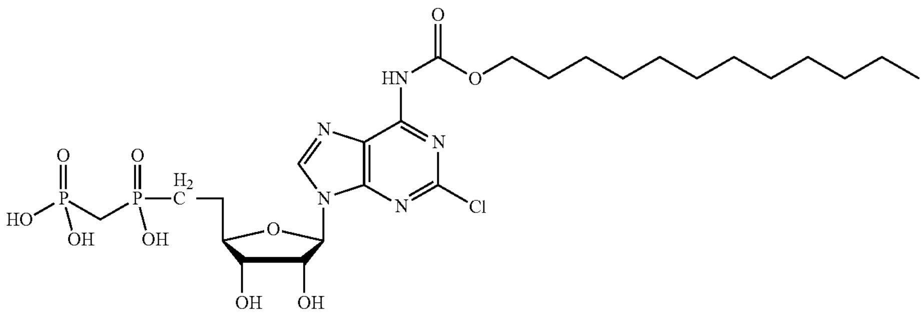 |
| a-16 | 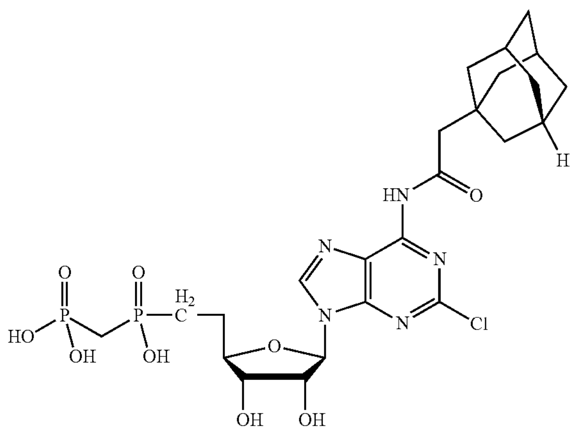 |
| a-17 | 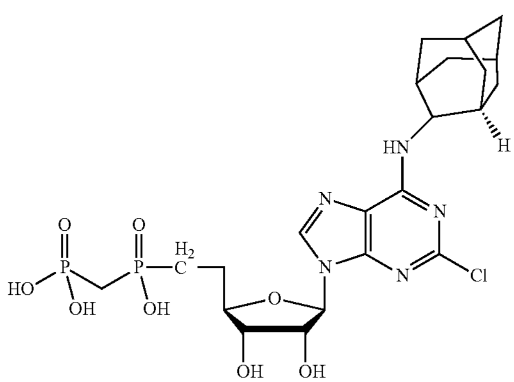 |
| a-18 | 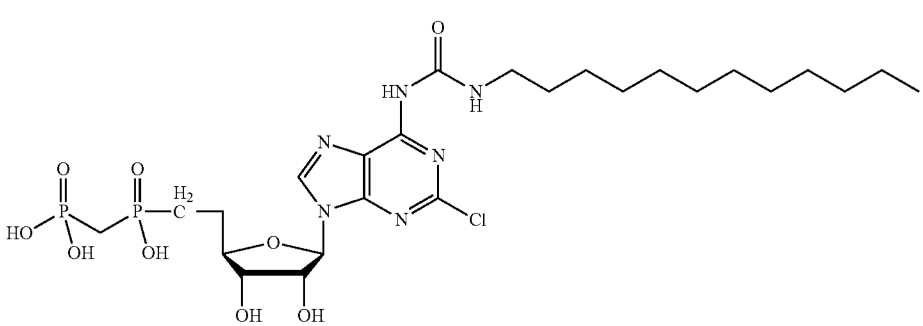 |

TABLE 1a-continued
Structures of example compounds.
| Compound Number | Structure |
|---|---|
| a-19 | 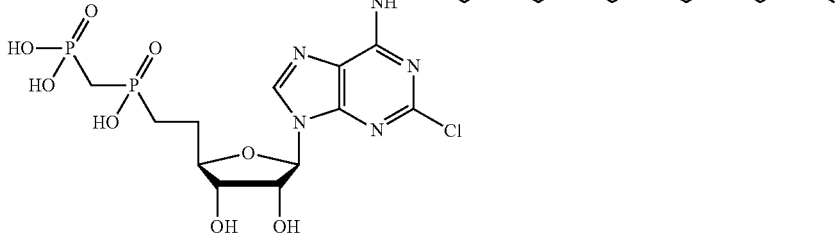 |
| a-20 | 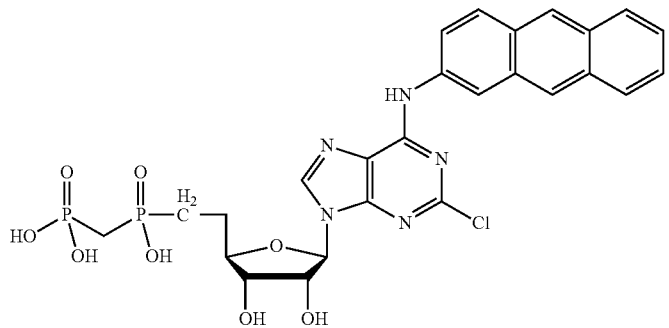 |
| a-21 | 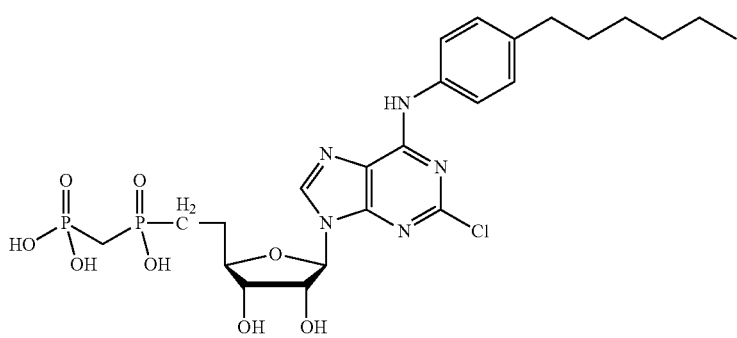 |
| a-22 | 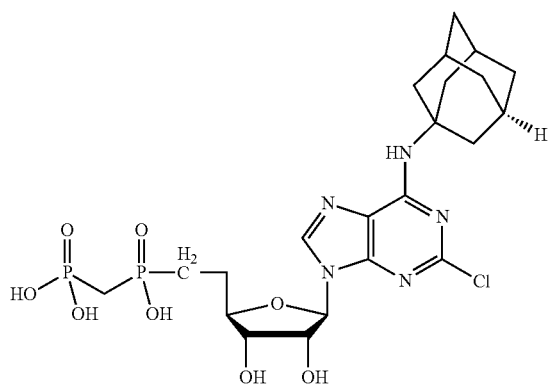 |

TABLE 1a-continued
Structures of example compounds.
| Compound Number | Structure |
|---|---|
| a-23 | 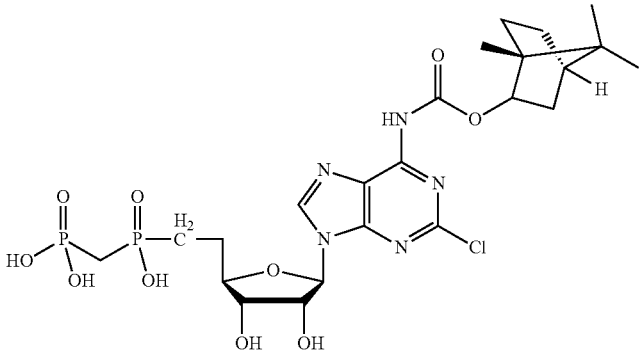 |
| a-24 | 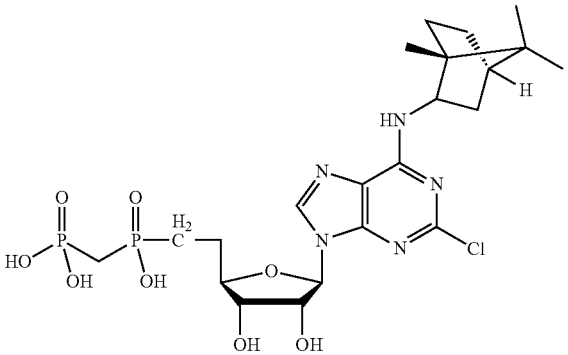 |
| a-25 | 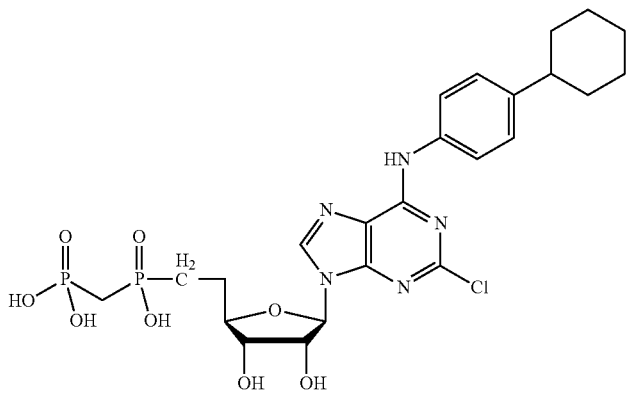 |
| a-26 | 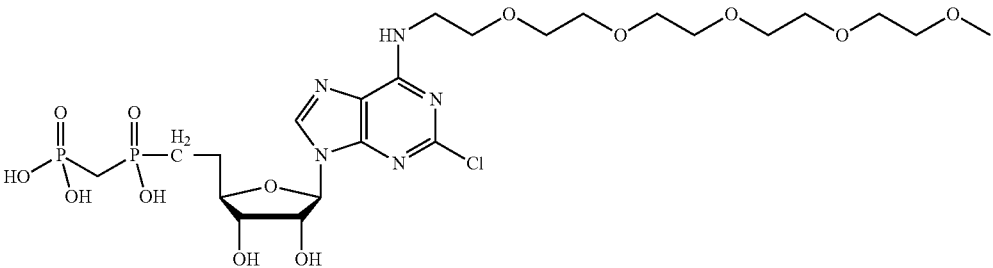 |

TABLE 1a-continued
Structures of example compounds.
| Compound Number | Structure |
|---|---|
| a-27 | 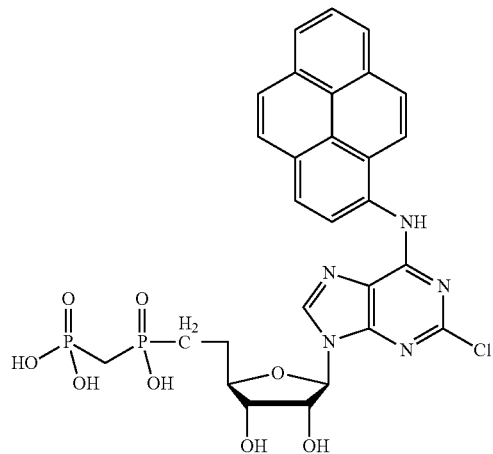 |
| a-28 | 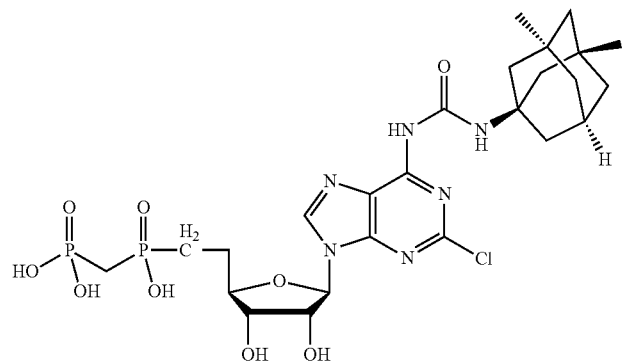 |
| a-29 | 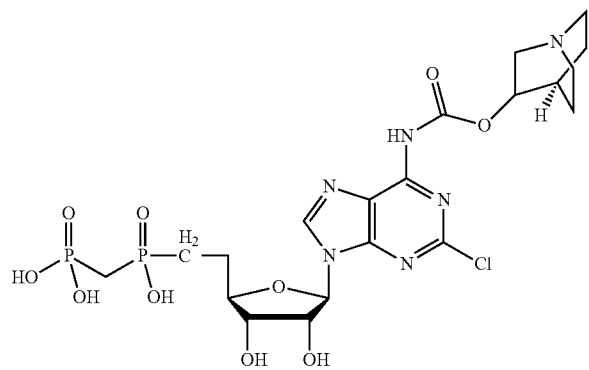 |

TABLE 1a-continued

Structures of example compounds.

| Compound Number | Structure |
|---|---|
| a-30 | 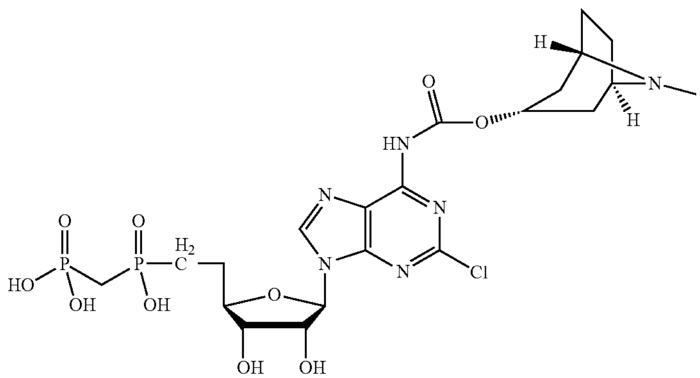 |
| a-31 | 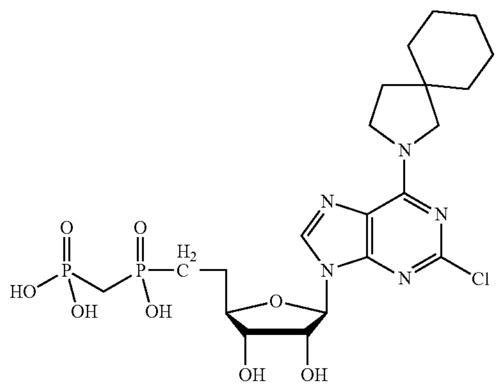 |
| a-32 | 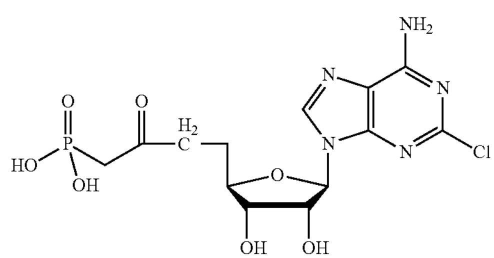 |
| a-33 | 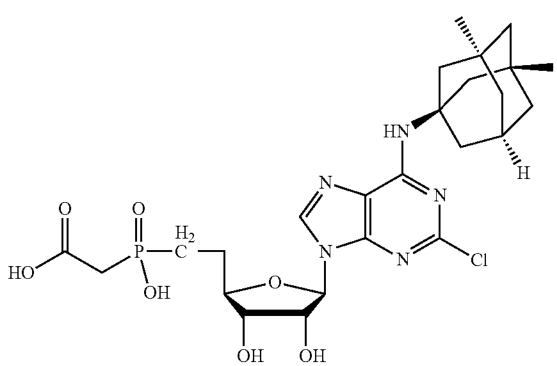 |

TABLE 1a-continued

Structures of example compounds.

| Compound Number | Structure |
|---|---|
| a-34 | 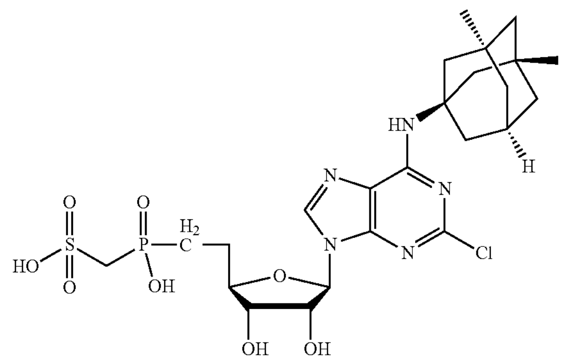 |
| a-35 | 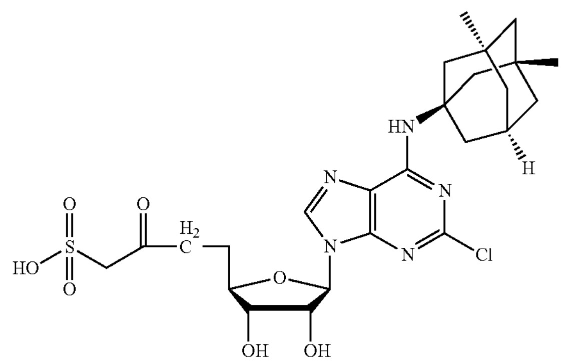 |
| a-36 | 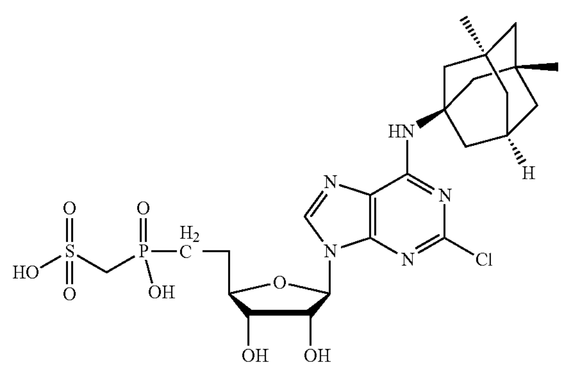 |
| a-37 | 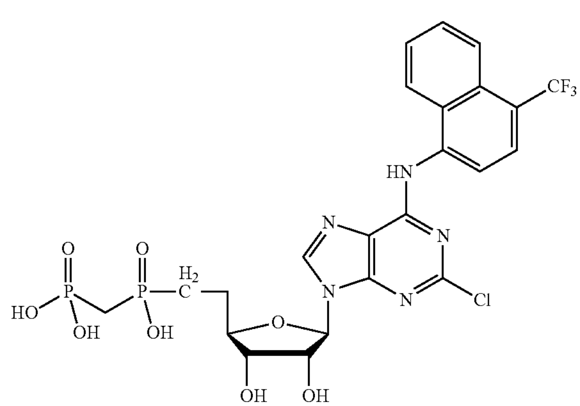 |

TABLE 1a-continued

Structures of example compounds.

| Compound Number | Structure |
|---|---|
| a-38 | 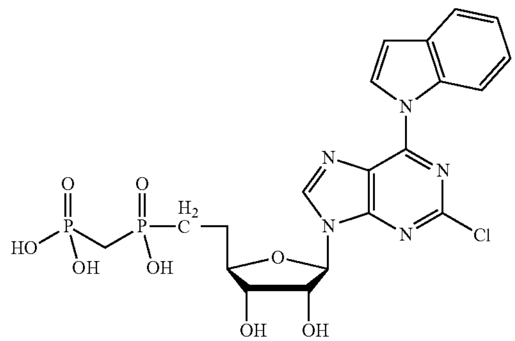 |
| a-39 | 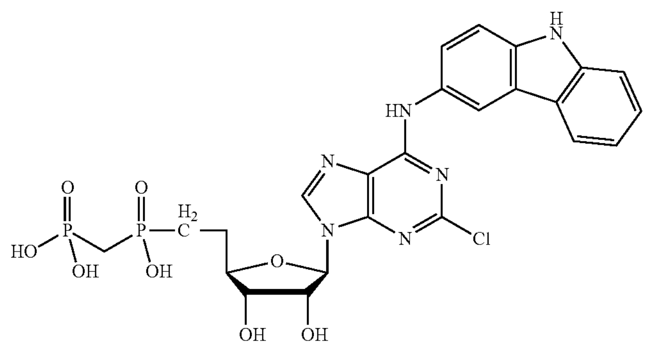 |
| a-40 | 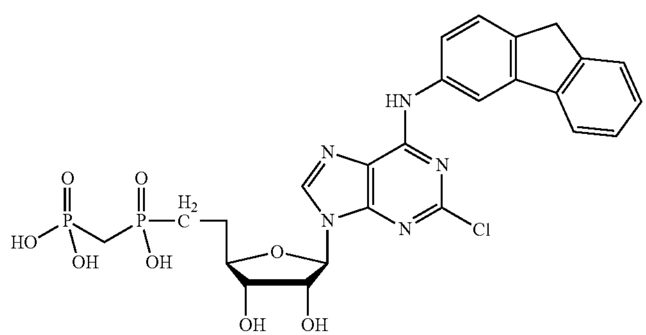 |
| a-41 | 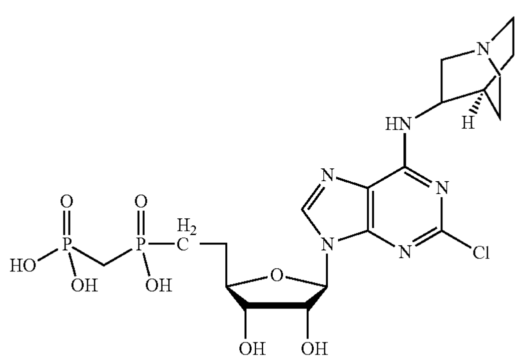 |

TABLE 1a-continued

Structures of example compounds.

| Compound Number | Structure |
|---|---|
| a-42 | 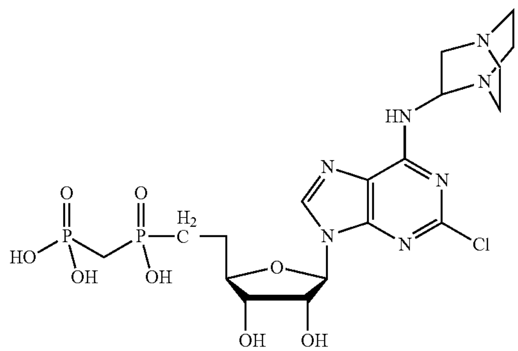 |
| a-43 | 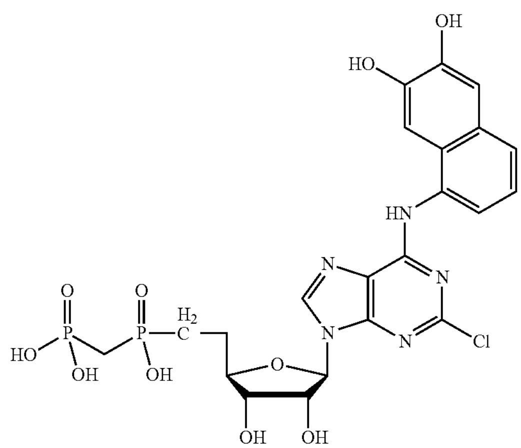 |
| a-44 | 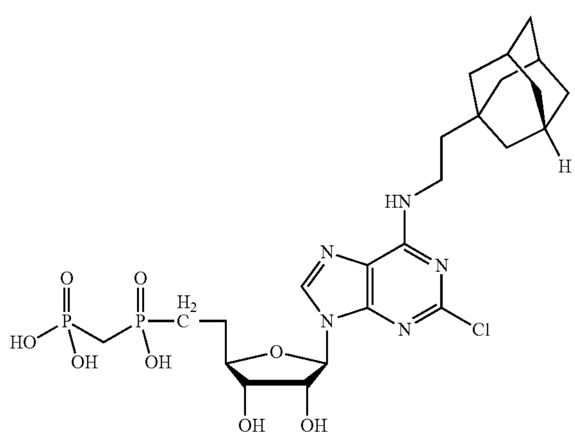 |

TABLE 1a-continued

Structures of example compounds.

| Compound Number | Structure |
|---|---|
| a-45 | 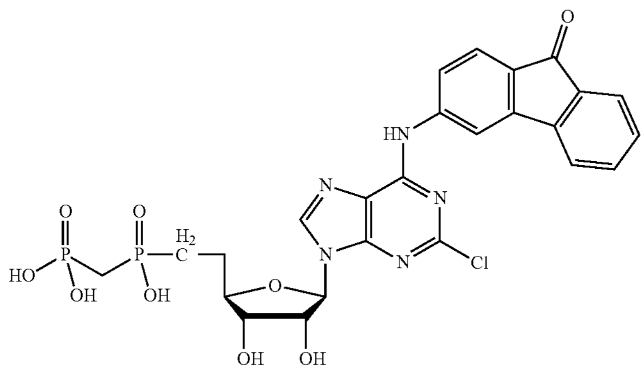 |
| a-46 | 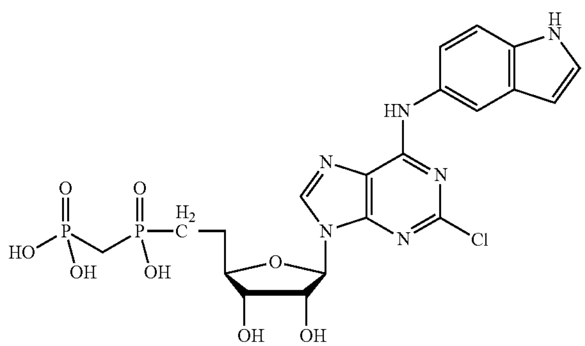 |
| a-47 | 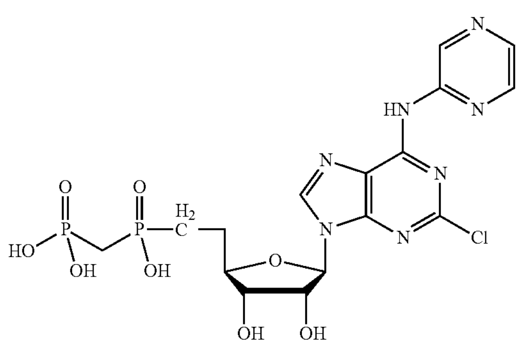 |
| a-48 | 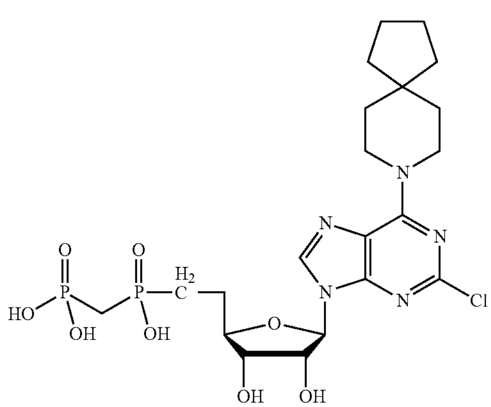 |

TABLE 1a-continued
Structures of example compounds.
| Compound Number | Structure |
|---|---|
| a-49 | 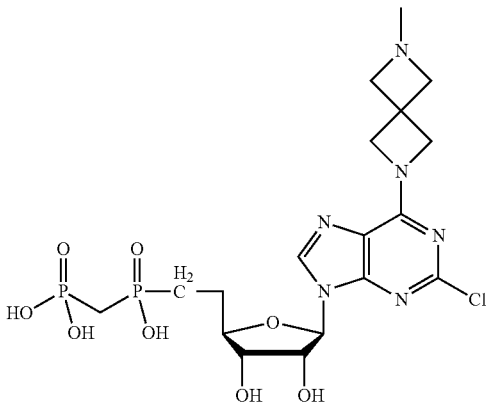 |
| a-50 | 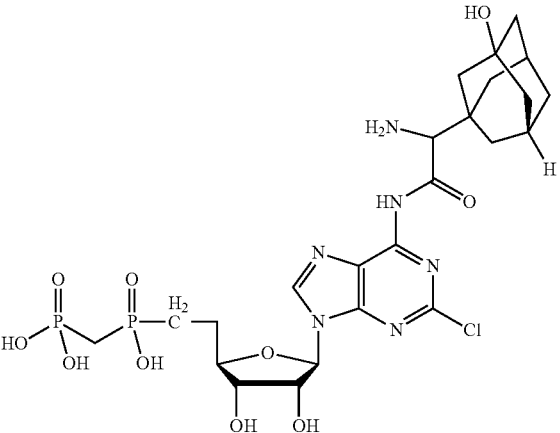 |
| a-51 | 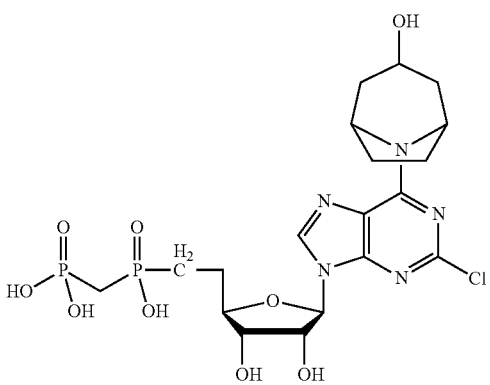 |
| a-52 | 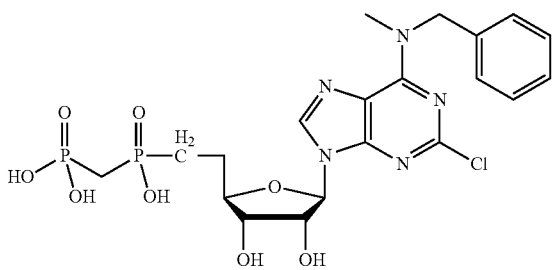 |

TABLE 1a-continued
Structures of example compounds.
| Compound Number | Structure |
|---|---|
| a-53 | 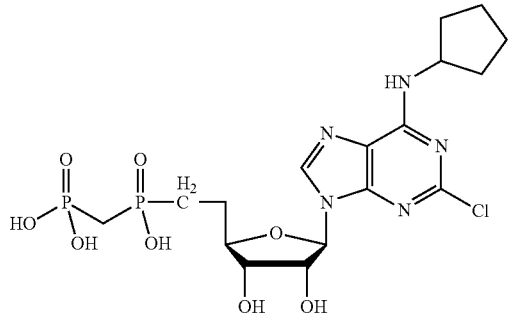 |
| a-54 | 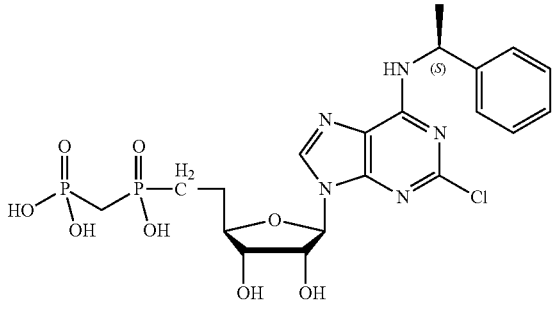 |
| a-55 | 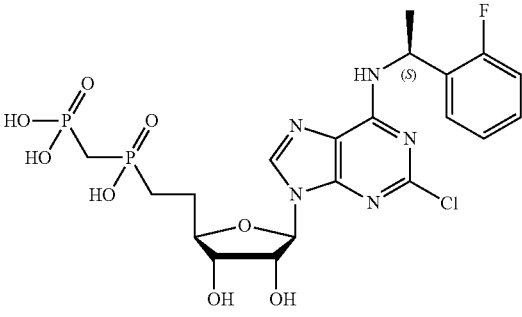 |
| a-56 | 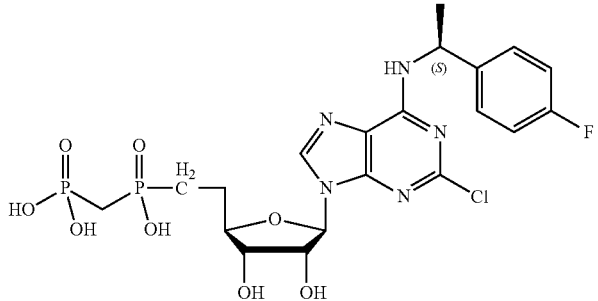 |

TABLE 1a-continued

Structures of example compounds.

| Compound Number | Structure |
| --- | --- |
| a-57 | 6-(pyrrolidin-1-yl)-2-chloro purine ribose methylenebisphosphonate |
| a-58 | 6-(2-chlorobenzylamino)-2-chloro purine ribose methylenebisphosphonate |
| a-59 | 6-(N-cyclopentyl-N-methylamino)-2-chloro purine ribose methylenebisphosphonate |
| a-60 | 6-amino-2-chloro purine ribose methylenebisphosphonate |

TABLE 1a-continued
Structures of example compounds.
| Compound Number | Structure |
|---|---|
| a-61 | 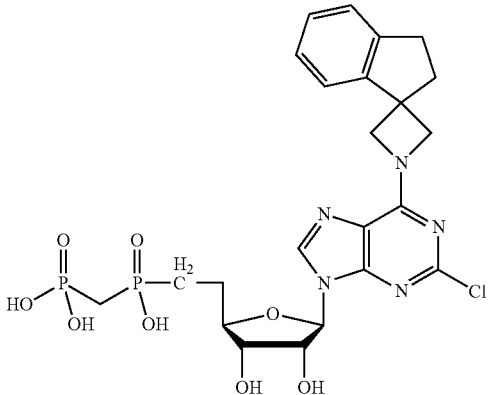 |
In some embodiments, there are provided compounds of Table 1b and pharmaceutically acceptable salts or esters thereof.
TABLE 1b
Structures of example compounds.
| Compound Number | Structure |
|---|---|
| b-1 | 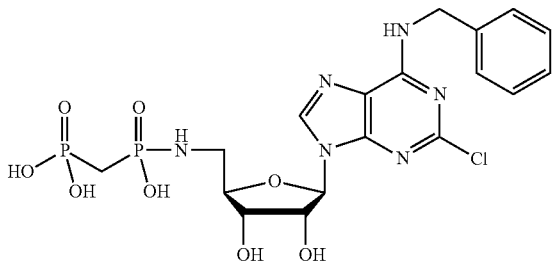 |
| b-2 | 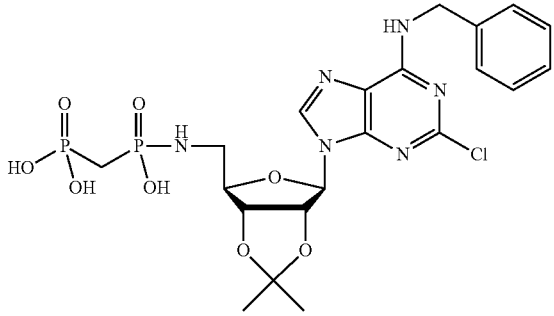 |

TABLE 1b-continued

Structures of example compounds.

| Compound Number | Structure |
| --- | --- |
| b-3 | 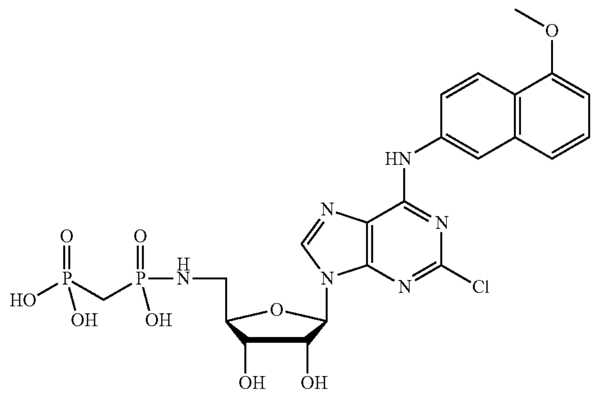 |
| b-4 | 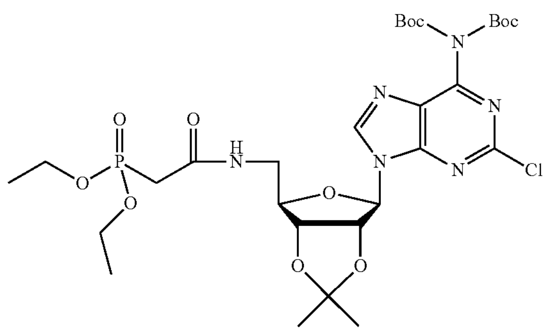 |
| b-5 | 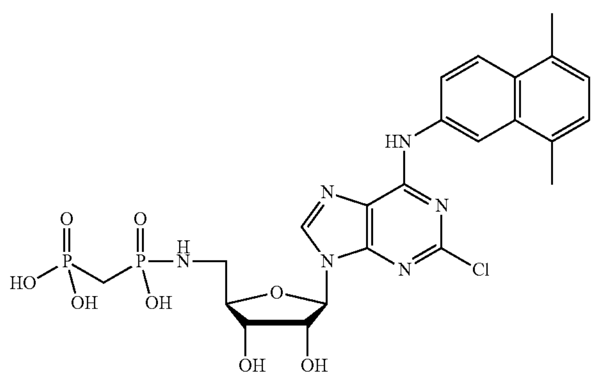 |
| b-6 | 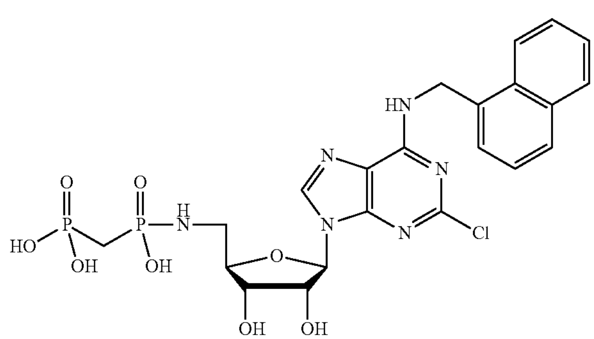 |

TABLE 1b-continued
Structures of example compounds.
| Compound Number | Structure |
|---|---|
| b-7 | 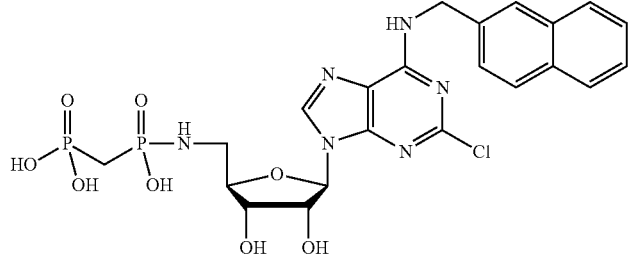 |
| b-8 | 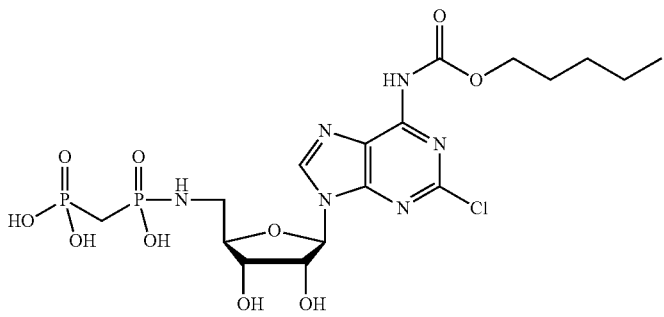 |
| b-9 | 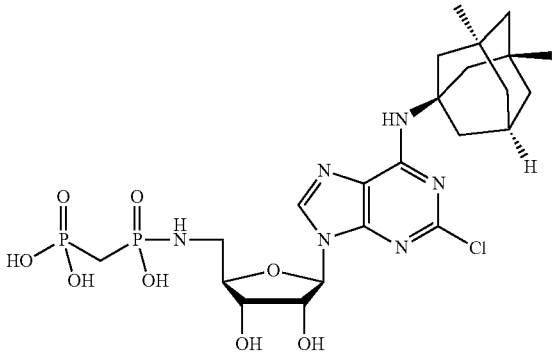 |
| b-10 | 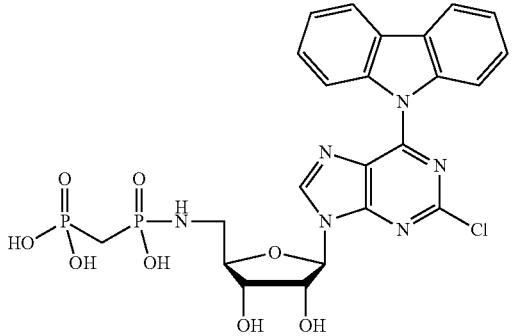 |

TABLE 1b-continued
Structures of example compounds.
| Compound Number | Structure |
|---|---|
| b-11 | 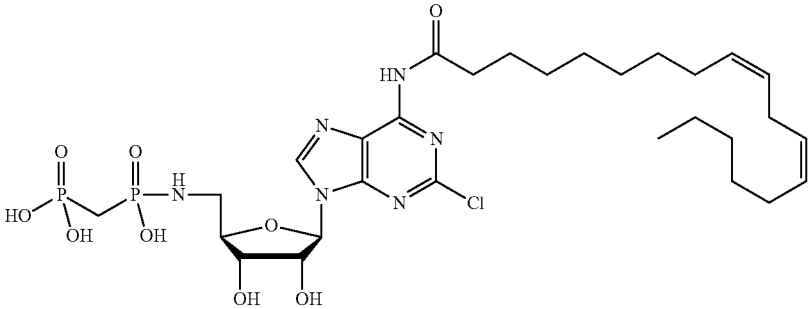 |
| b-12 | 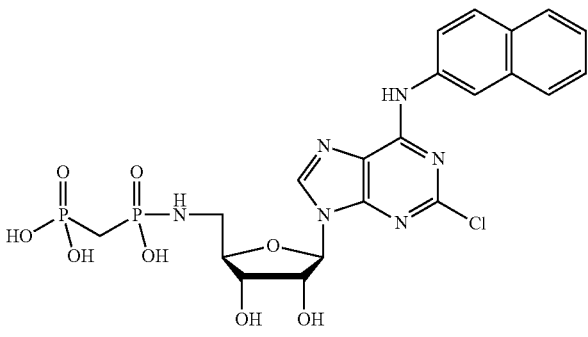 |
| b-13 | 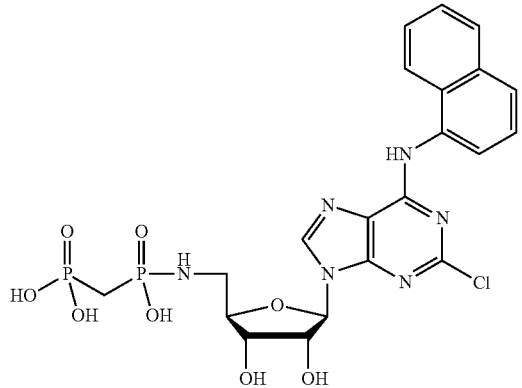 |
| b-14 | 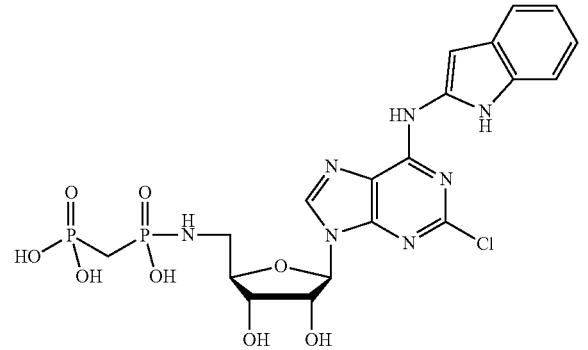 |

TABLE 1b-continued

Structures of example compounds.

| Compound Number | Structure |
|---|---|
| b-15 | 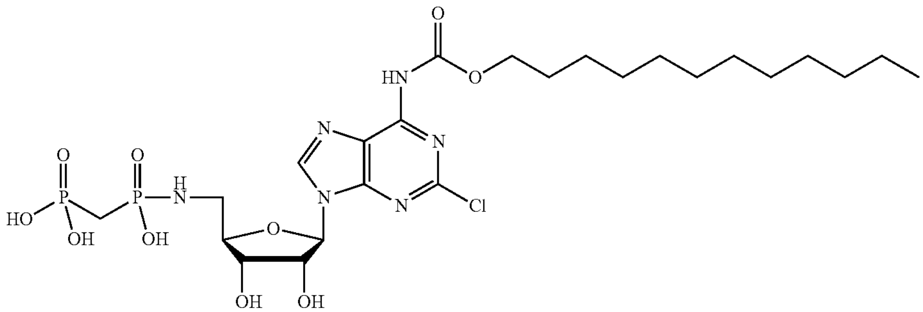 |
| b-16 | 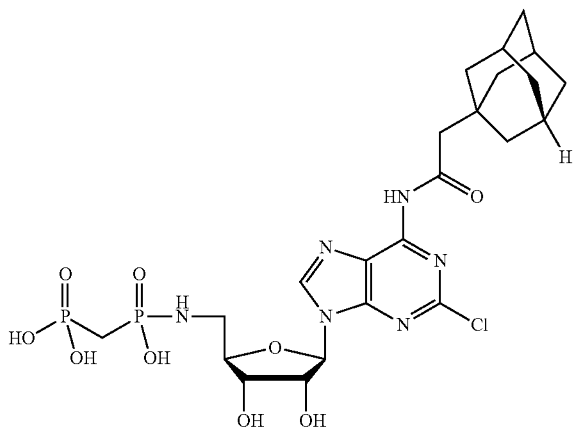 |
| b-17 | 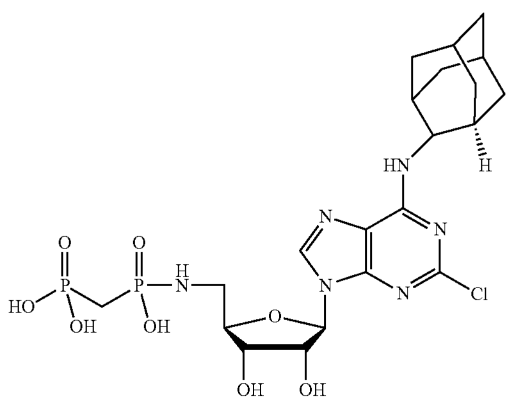 |
| b-18 | 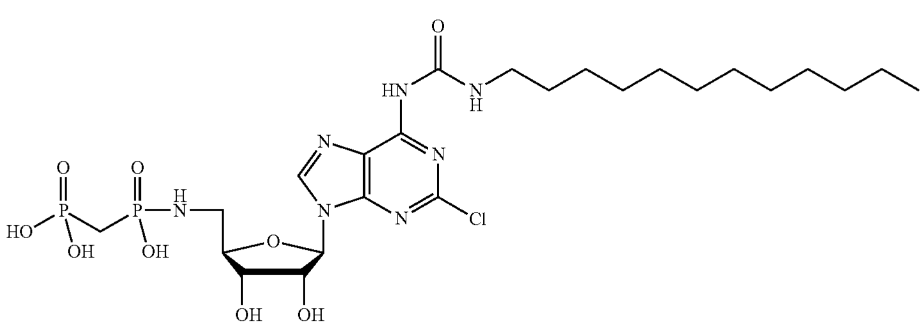 |

TABLE 1b-continued
Structures of example compounds.
| Compound Number | Structure |
|---|---|
| b-19 | 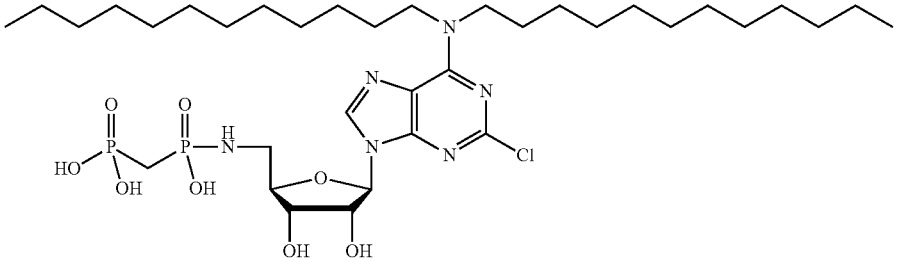 |
| b-20 | 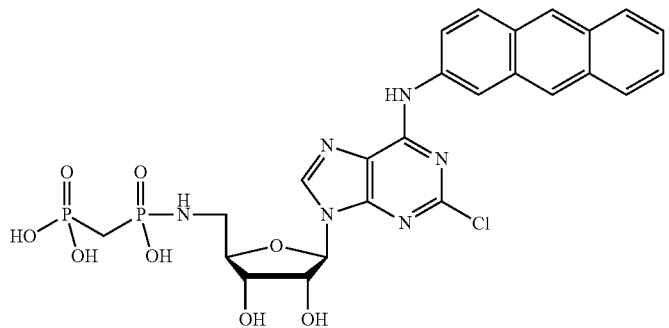 |
| b-21 | 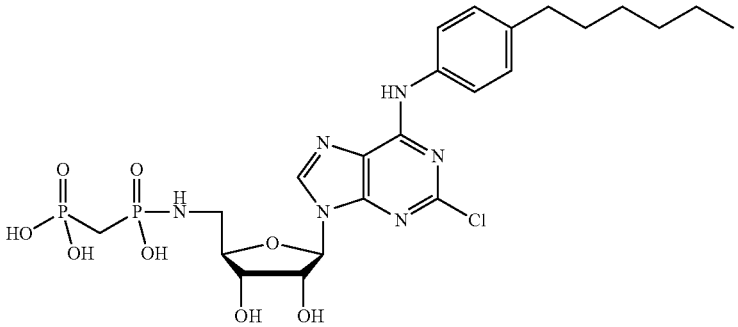 |
| b-22 | 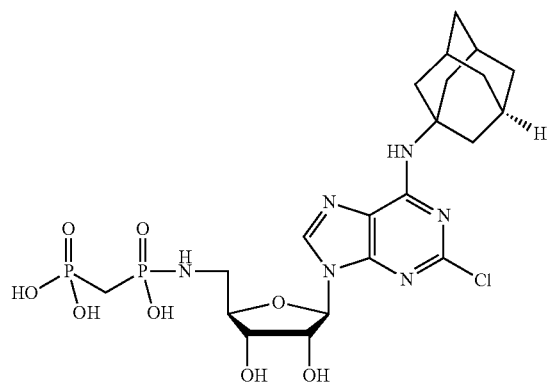 |

TABLE 1b-continued

Structures of example compounds.

| Compound Number | Structure |
| --- | --- |
| b-23 | 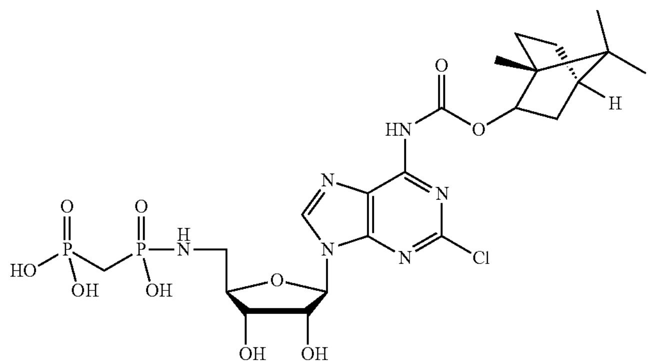 |
| b-24 | 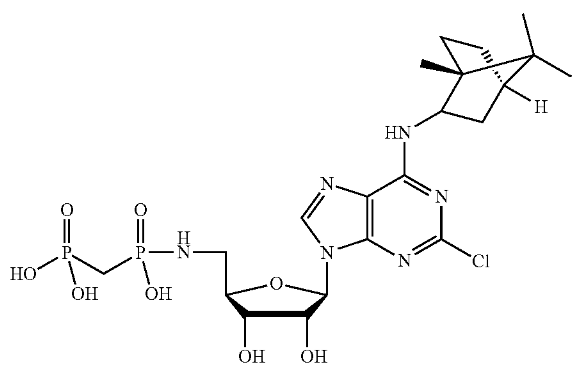 |
| b-25 | 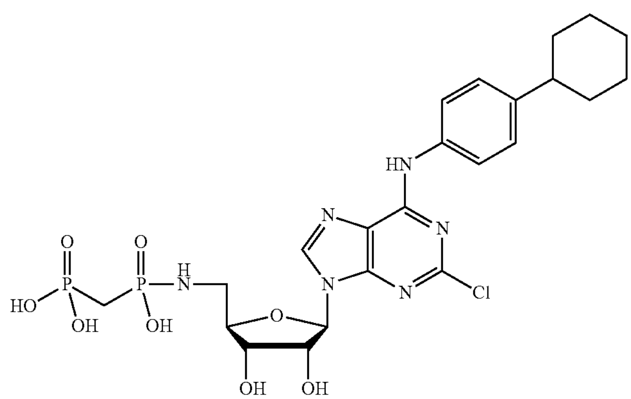 |
| b-26 | 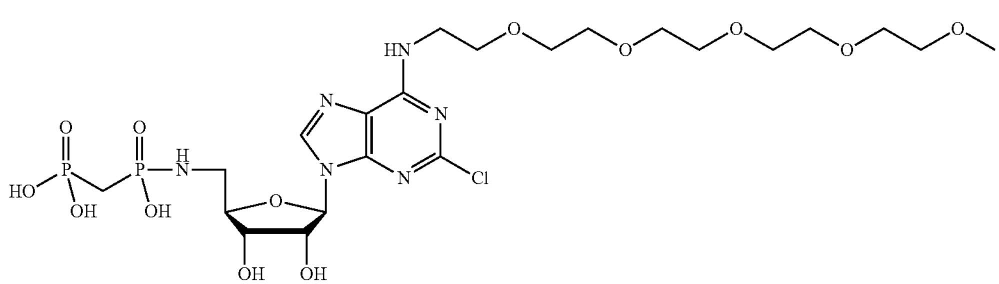 |

TABLE 1b-continued
Structures of example compounds.
| Compound Number | Structure |
|---|---|
| b-27 | 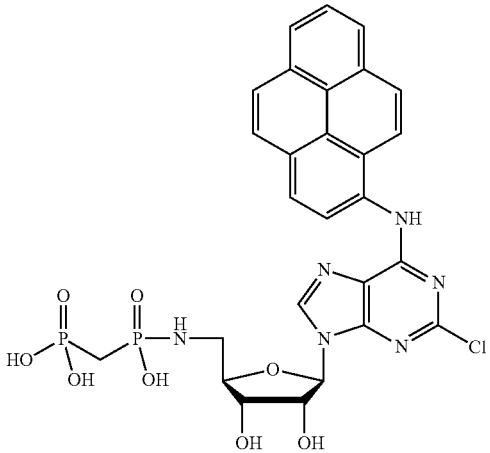 |
| b-28 | 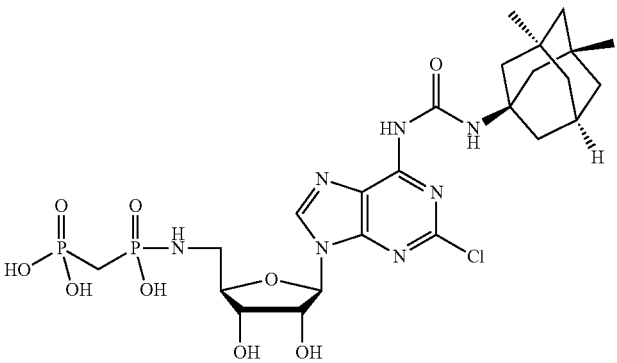 |
| b-29 | 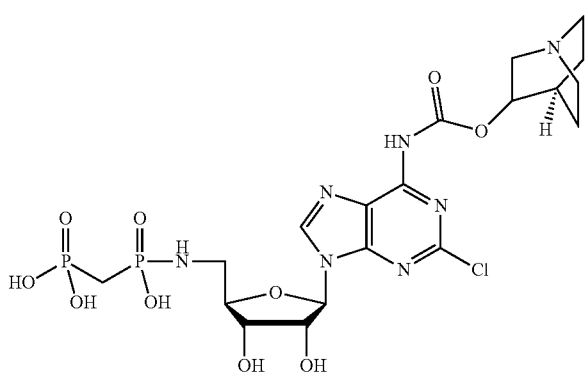 |

TABLE 1b-continued

Structures of example compounds.

| Compound Number | Structure |
| --- | --- |
| b-30 | 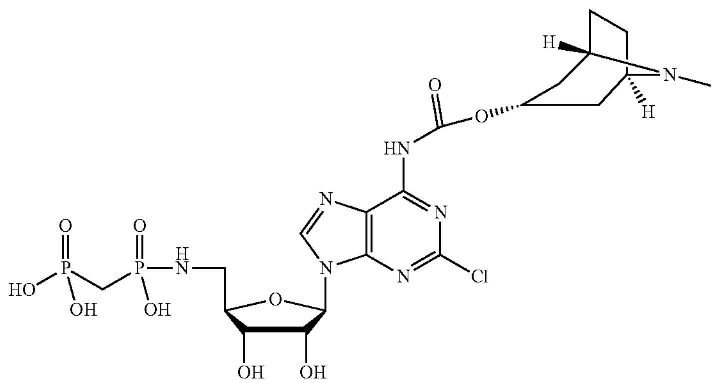 |
| b-31 | 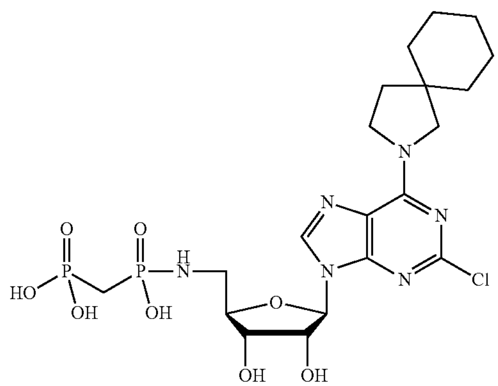 |
| b-32 | 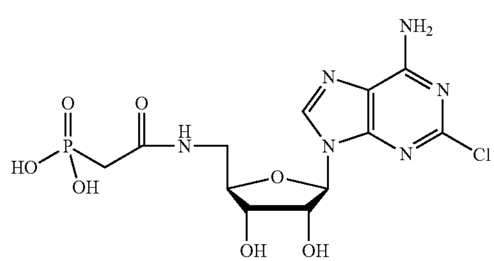 |
| b-33 | 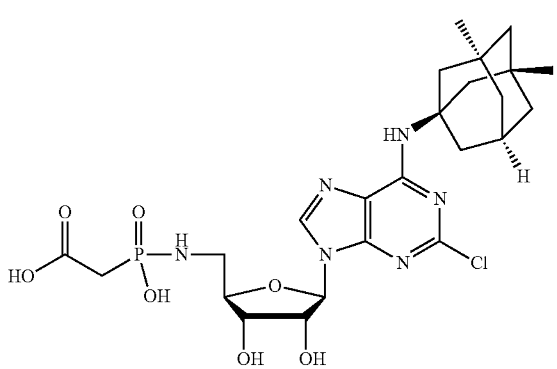 |

TABLE 1b-continued
Structures of example compounds.
| Compound Number | Structure |
|---|---|
| b-34 | 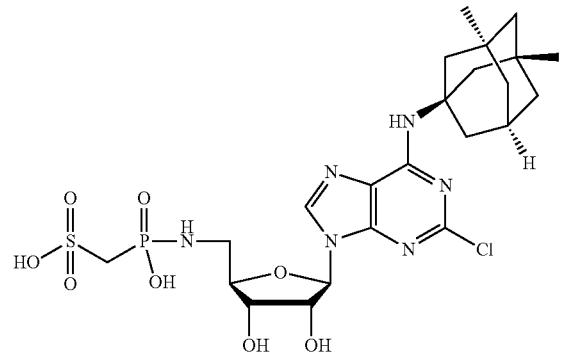 |
| b-35 | 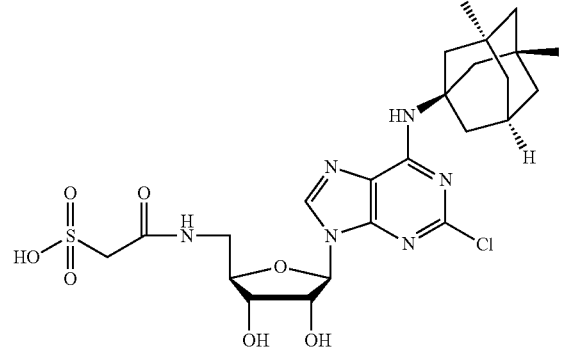 |
| b-36 | 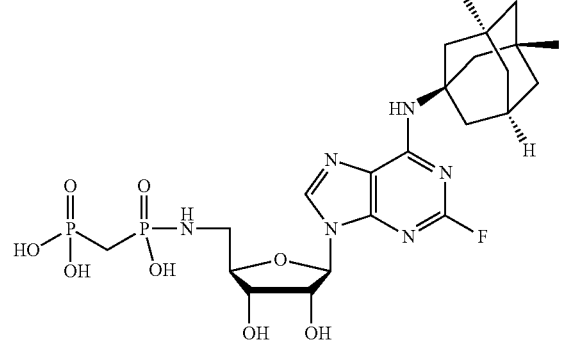 |
| b-37 | 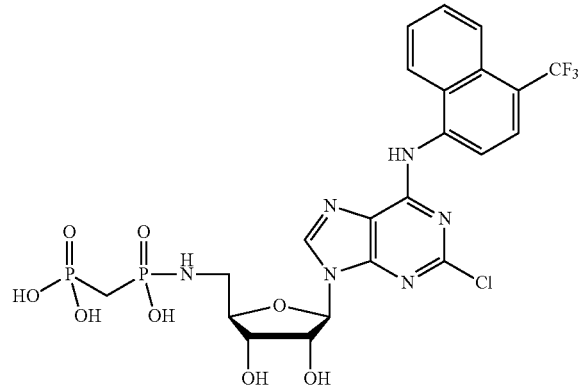 |

TABLE 1b-continued

Structures of example compounds.

| Compound Number | Structure |
|---|---|
| b-38 | 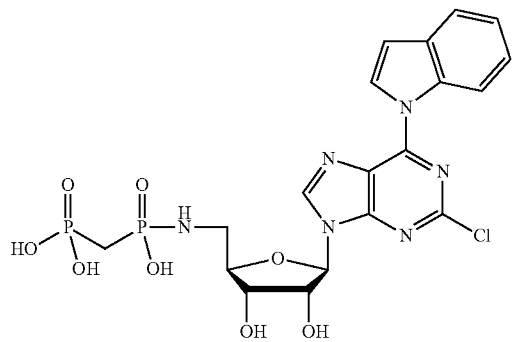 |
| b-39 | 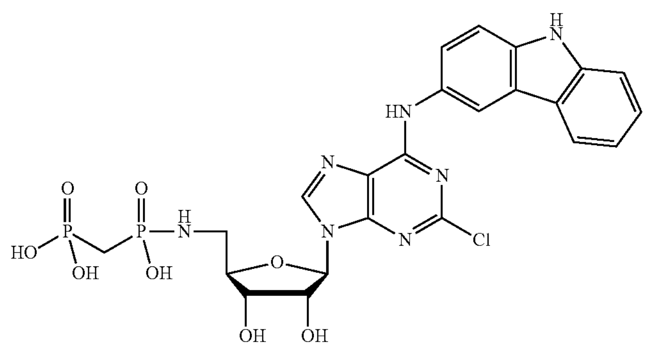 |
| b-40 | 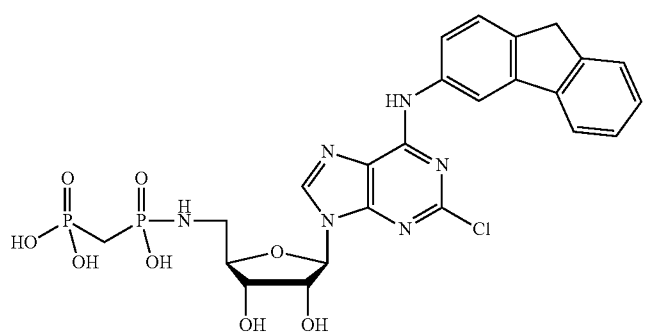 |
| b-41 | 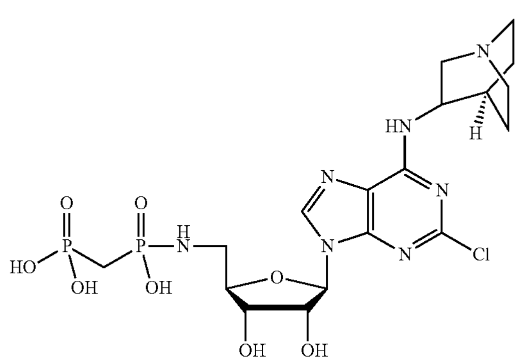 |

TABLE 1b-continued
Structures of example compounds.
| Compound Number | Structure |
|---|---|
| b-42 | 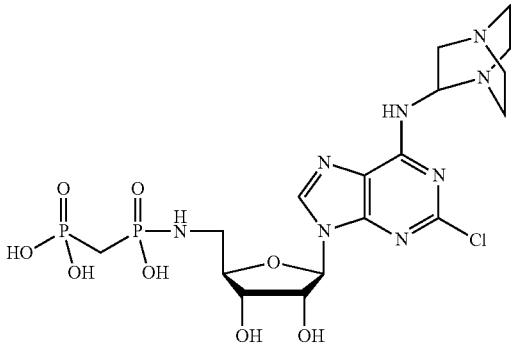 |
| b-43 | 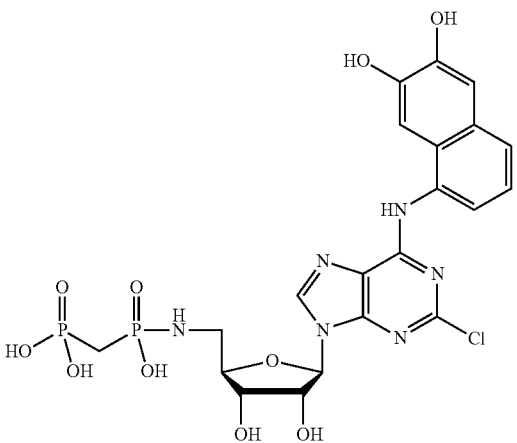 |
| b-44 | 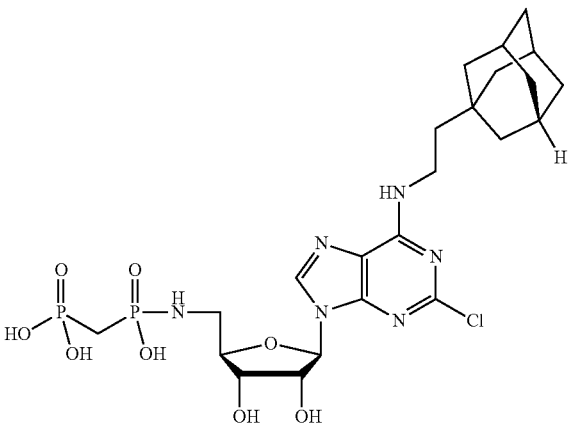 |

TABLE 1b-continued
Structures of example compounds.
| Compound Number | Structure |
|---|---|
| b-45 | 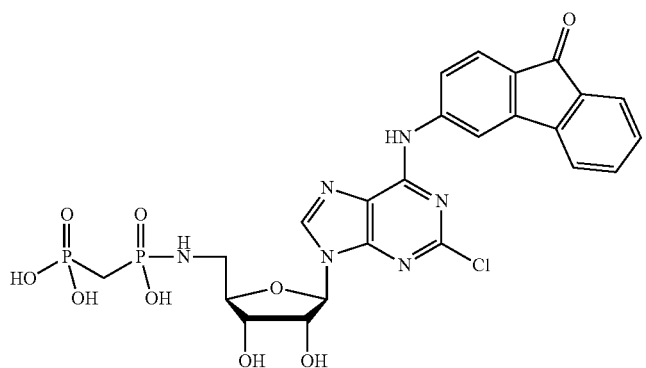 |
| b-46 | 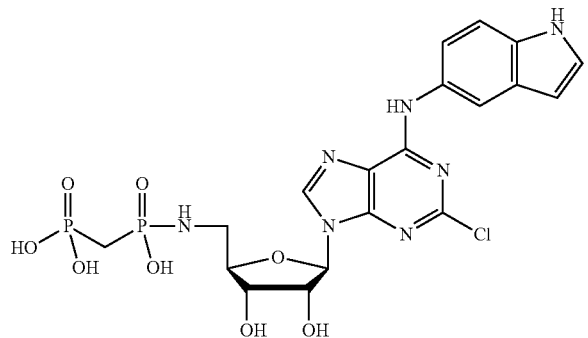 |
| b-47 | 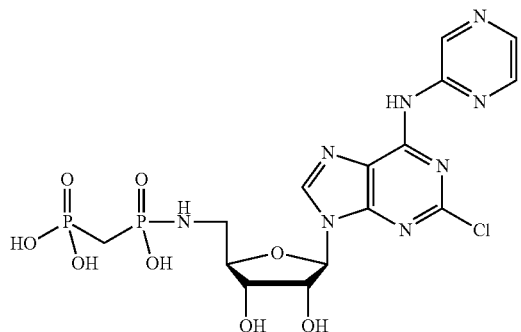 |
| b-48 | 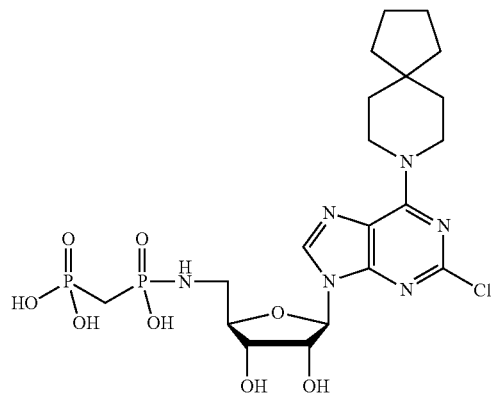 |

TABLE 1b-continued
Structures of example compounds.
| Compound Number | Structure |
|---|---|
| b-49 | 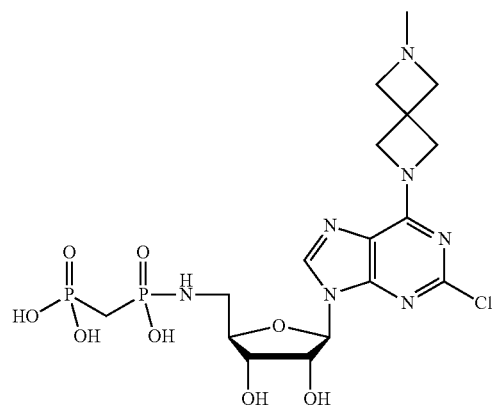 |
| b-50 | 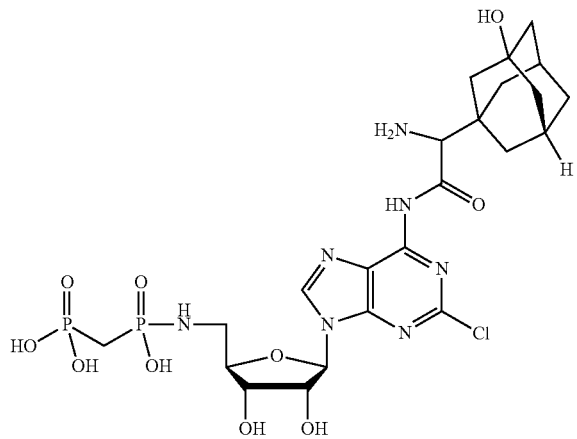 |
| b-51 | 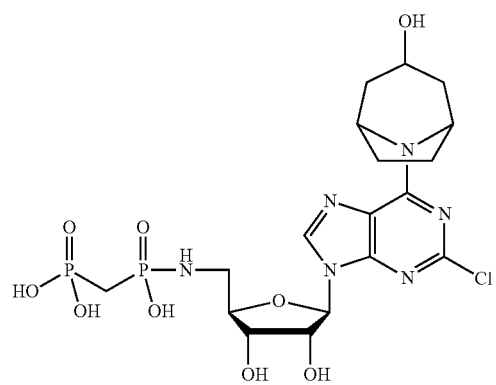 |
| b-52 | 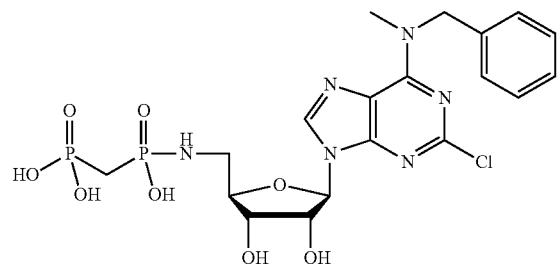 |

TABLE 1b-continued
Structures of example compounds.
| Compound Number | Structure |
|---|---|
| b-53 | 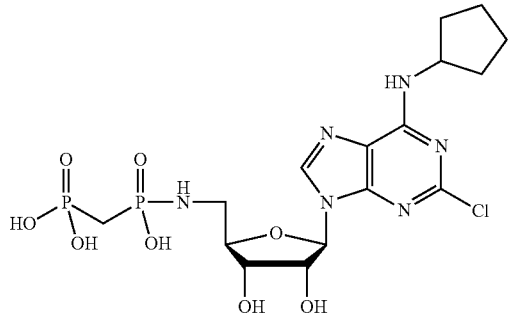 |
| b-54 | 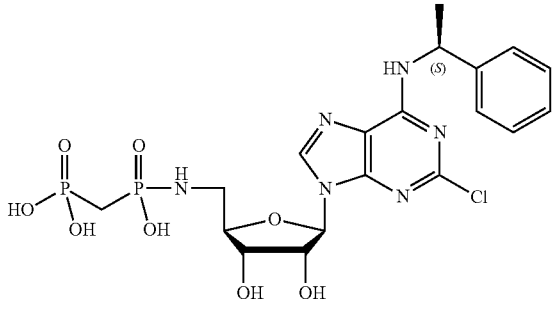 |
| b-55 | 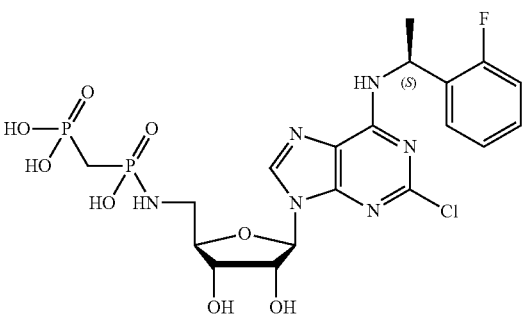 |
| b-56 | 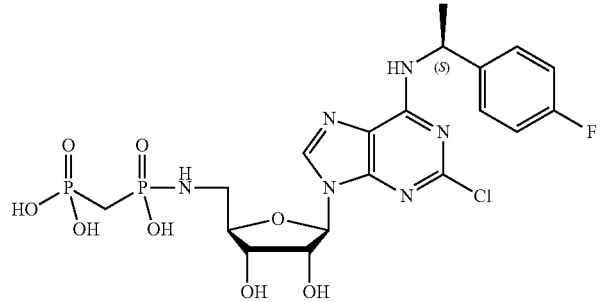 |

TABLE 1b-continued
Structures of example compounds.
| Compound Number | Structure |
|---|---|
| b-57 | 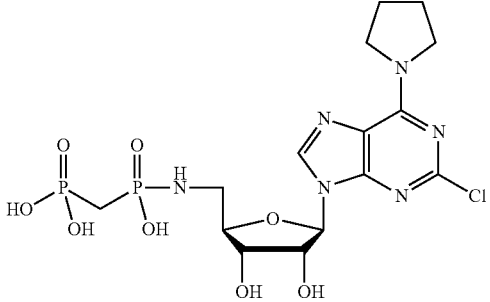 |
| b-58 | 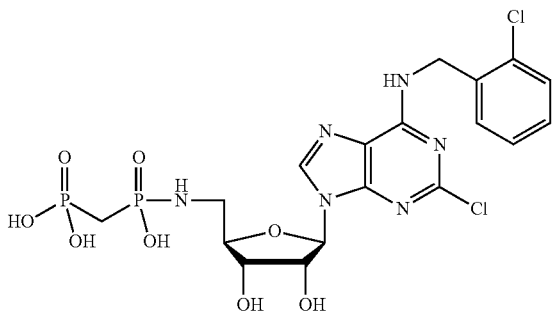 |
| b-59 | 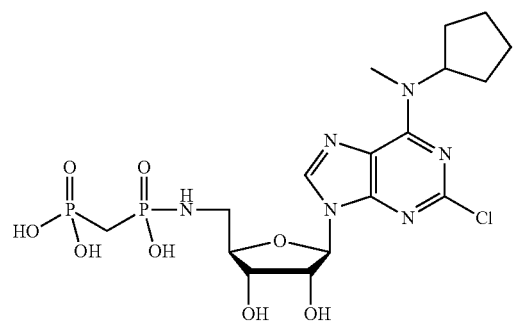 |
| b-60 | 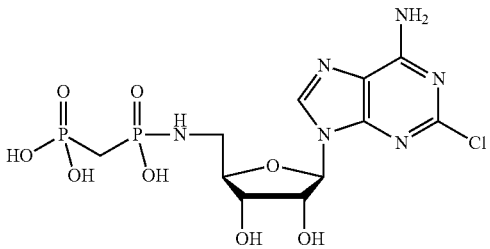 |

TABLE 1b-continued
Structures of example compounds.
| Compound Number | Structure |
|---|---|
| b-61 | 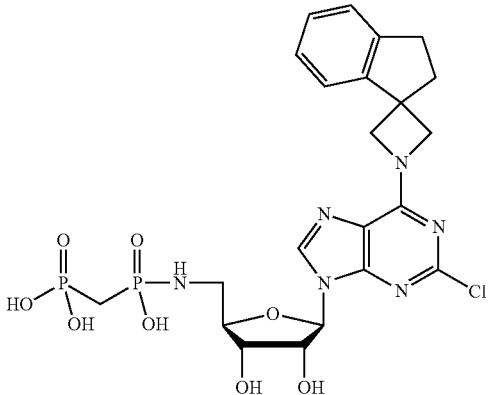 |
In some embodiments, there are provided compounds of Table 1c and pharmaceutically acceptable salts or esters thereof.
TABLE 1c
Structures of example compounds.
| Compound Number | Structure |
|---|---|
| c-1 | 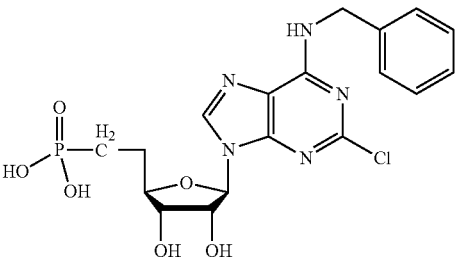 |
| c-2 | 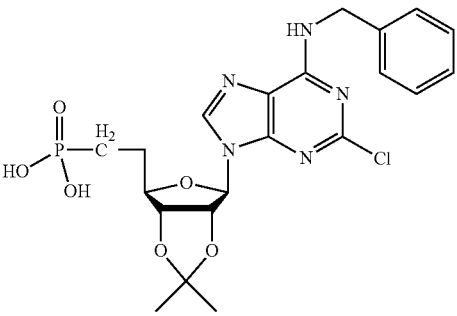 |

TABLE 1c-continued
Structures of example compounds.
| Compound Number | Structure |
|---|---|
| c-3 | 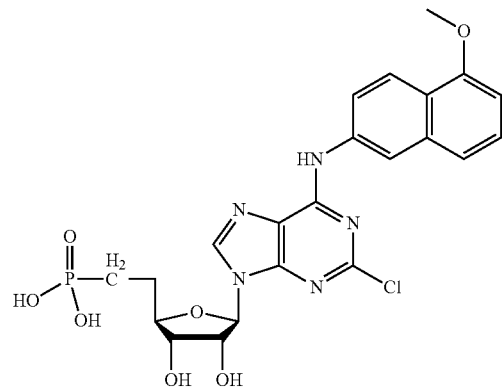 |
| c-4 | 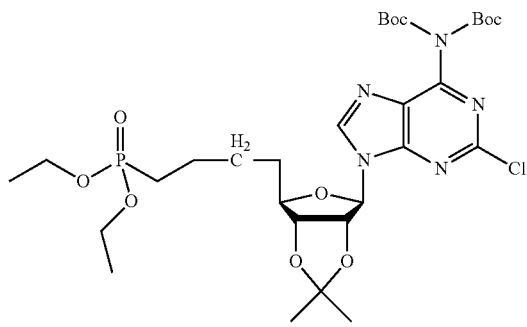 |
| c-5 | 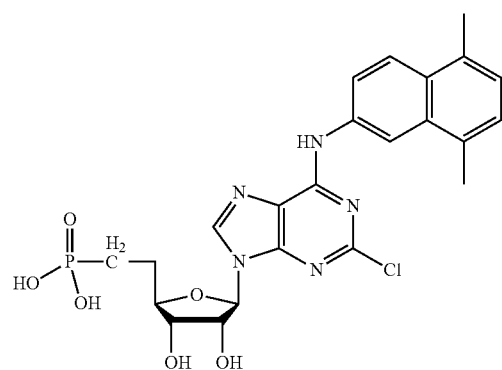 |
| c-6 | 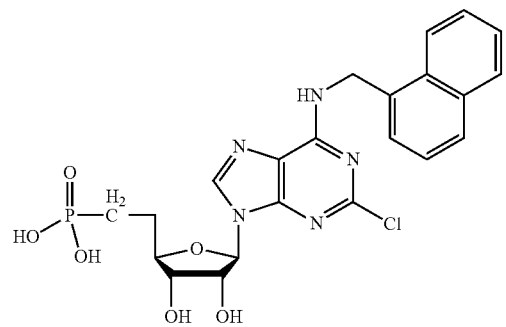 |

TABLE 1c-continued

Structures of example compounds.

| Compound Number | Structure |
|---|---|
| c-7 | 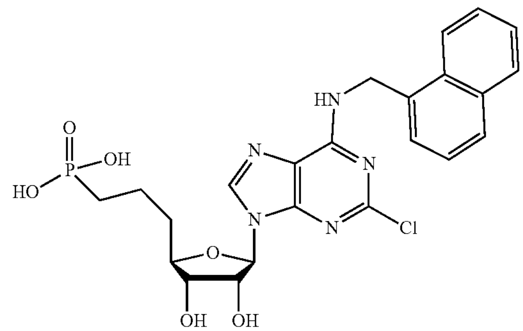 |
| c-8 | 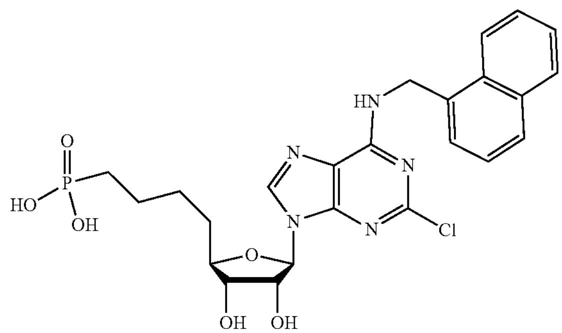 |
| c-9 | 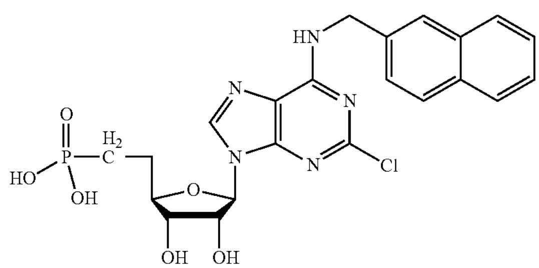 |
| c-10 | 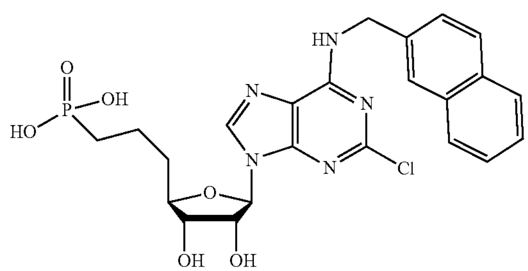 |
| c-11 | 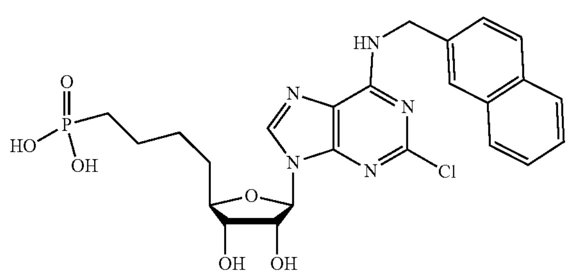 |

TABLE 1c-continued
Structures of example compounds.
| Compound Number | Structure |
|---|---|
| c-12 | 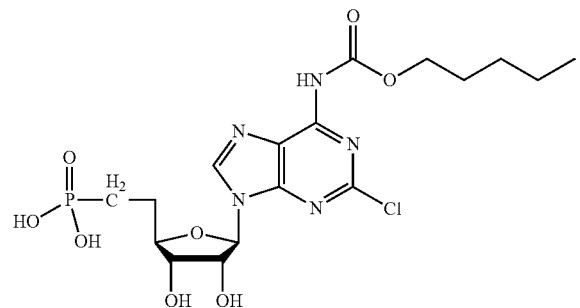 |
| c-13 | 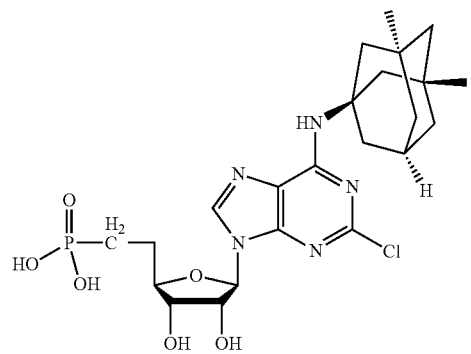 |
| c-14 | 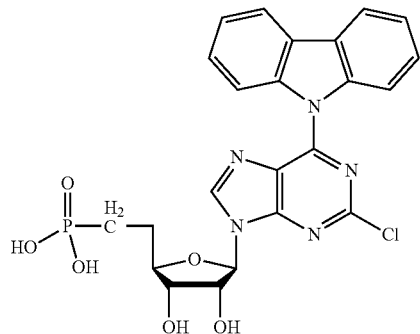 |
| c-15 | 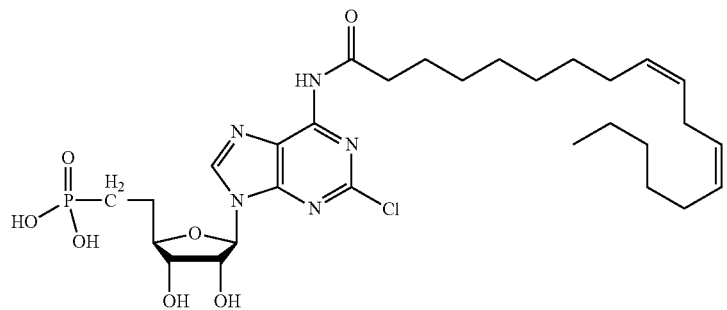 |

TABLE 1c-continued
Structures of example compounds.
| Compound Number | Structure |
| --- | --- |
| c-16 | 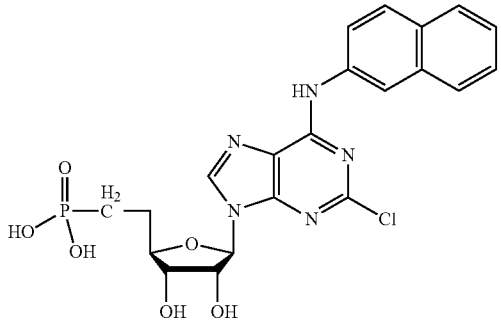 |
| c-17 | 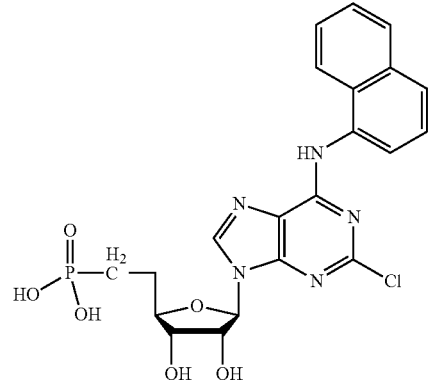 |
| c-18 | 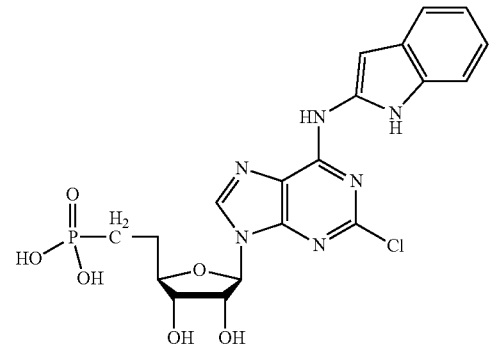 |
| c-19 | 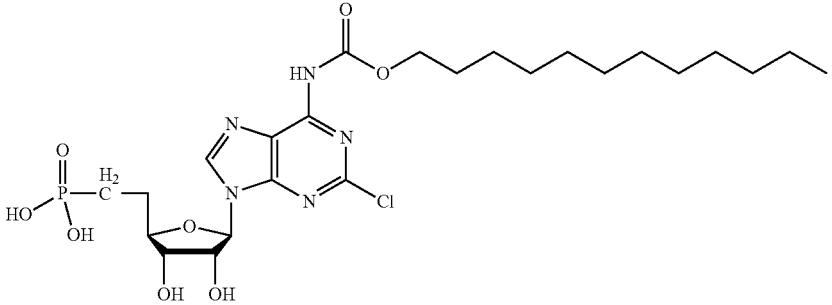 |

TABLE 1c-continued
Structures of example compounds.
| Compound Number | Structure |
|---|---|
| c-20 | 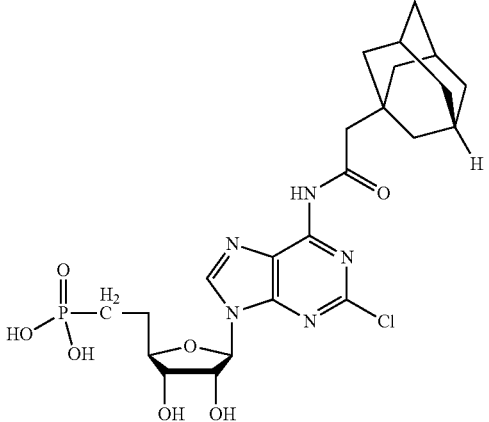 |
| c-21 | 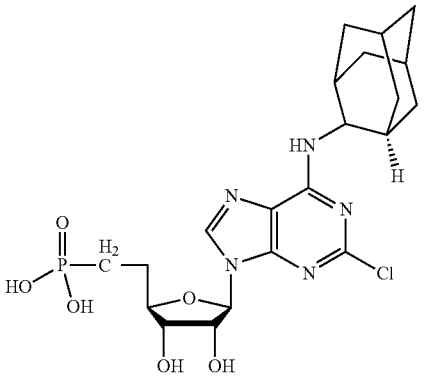 |
| c-22 | 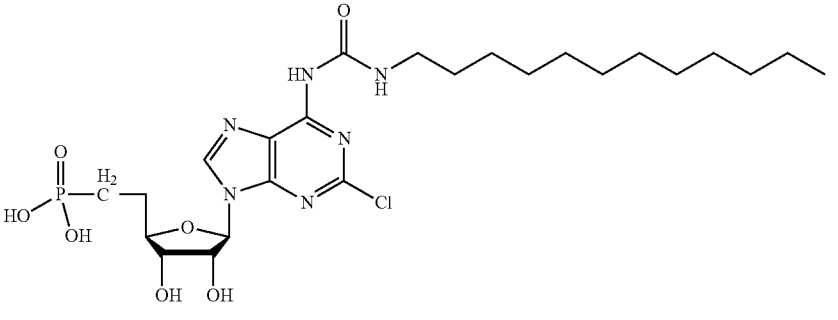 |
| c-23 | 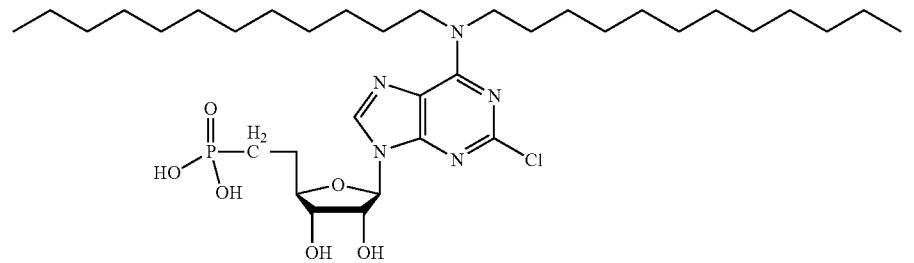 |

TABLE 1c-continued
Structures of example compounds.
| Compound Number | Structure |
|---|---|
| c-24 | 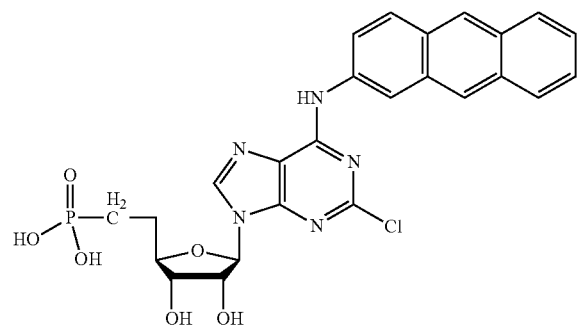 |
| c-25 | 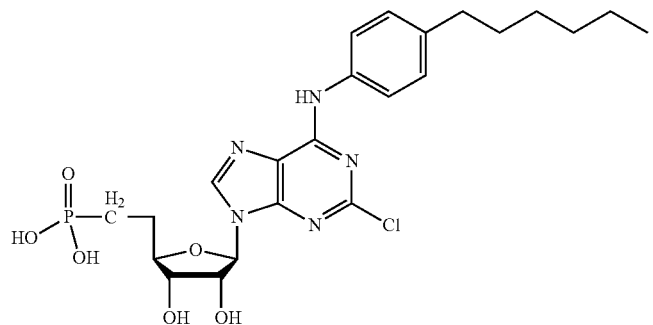 |
| c-26 | 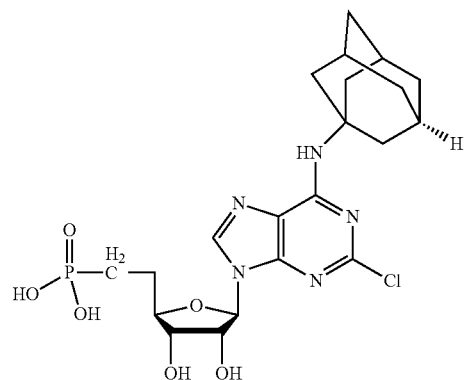 |
| c-27 | 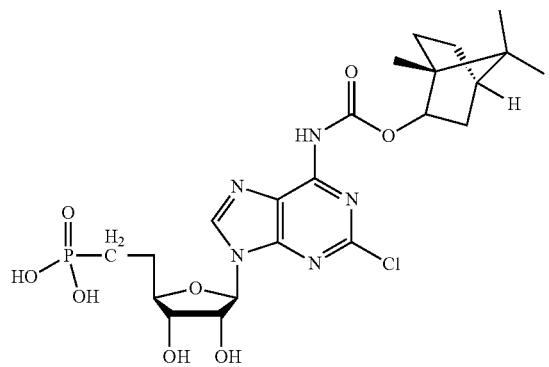 |

TABLE 1c-continued

Structures of example compounds.

| Compound Number | Structure |
|---|---|
| c-28 | 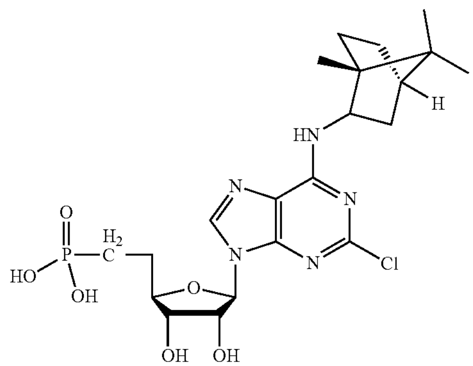 |
| c-29 | 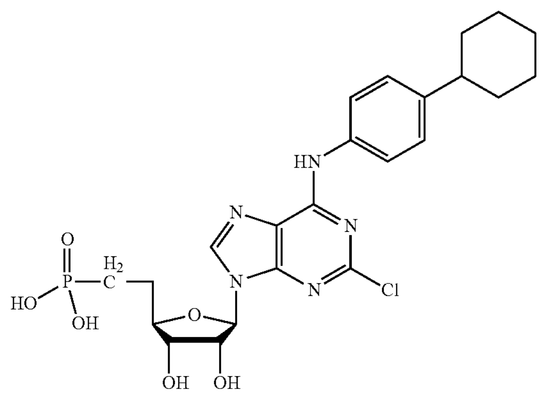 |
| c-30 | 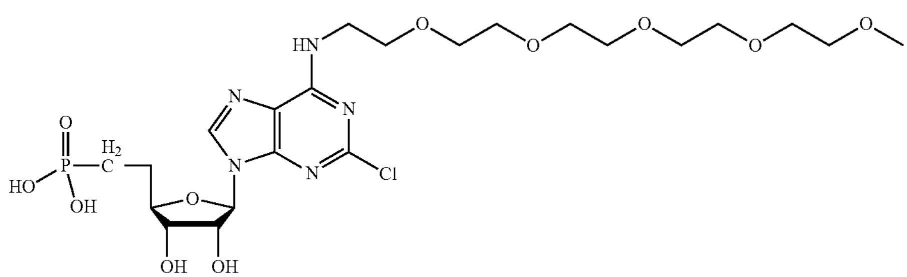 |
| c-31 | 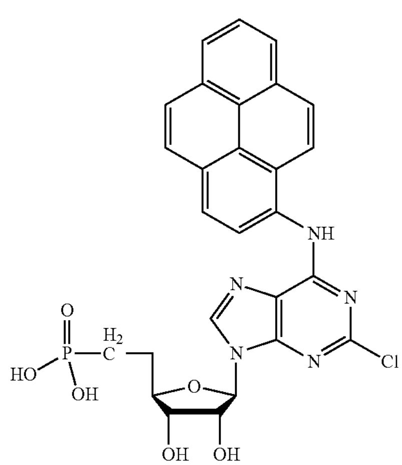 |

TABLE 1c-continued

Structures of example compounds.

| Compound Number | Structure |
|---|---|
| c-32 | 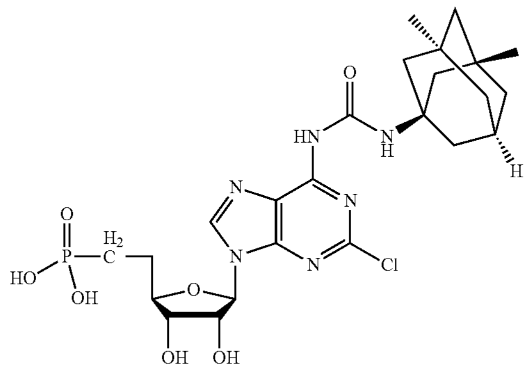 |
| c-33 | 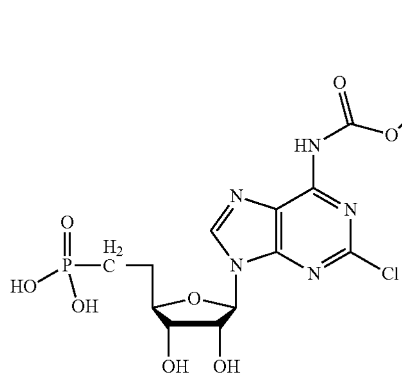 |
| c-34 | 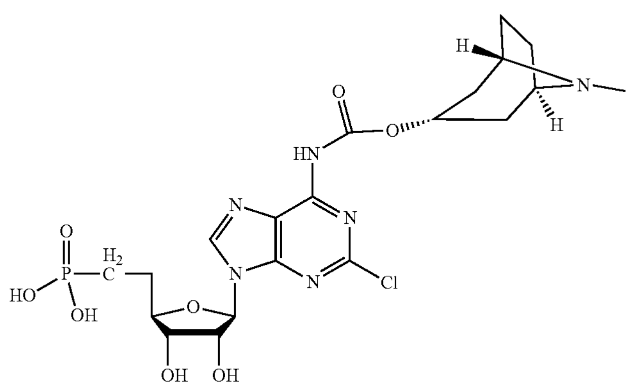 |
| c-35 | 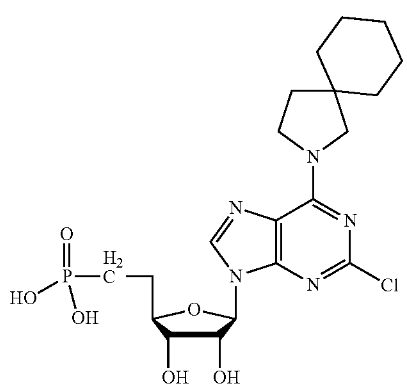 |

TABLE 1c-continued
Structures of example compounds.
| Compound Number | Structure |
|---|---|
| c-36 | 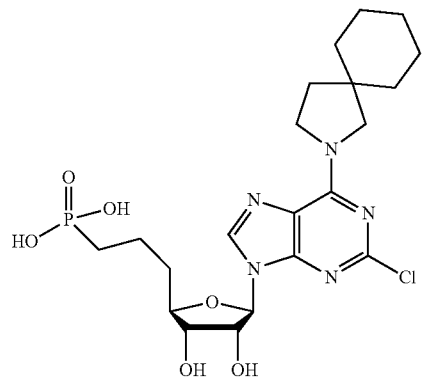 |
| c-37 | 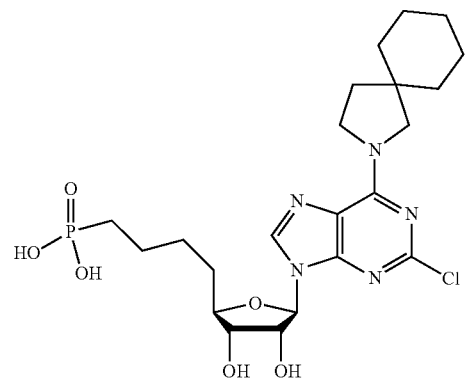 |
| c-38 | 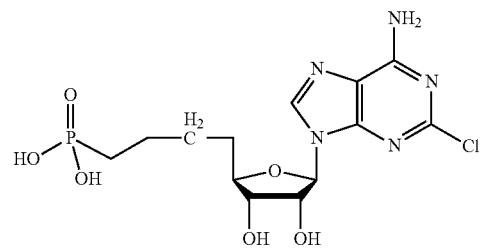 |
| c-39 | 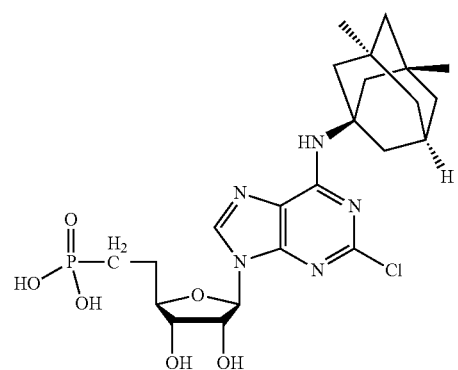 |

TABLE 1c-continued
Structures of example compounds.
| Compound Number | Structure |
|---|---|
| c-40 | 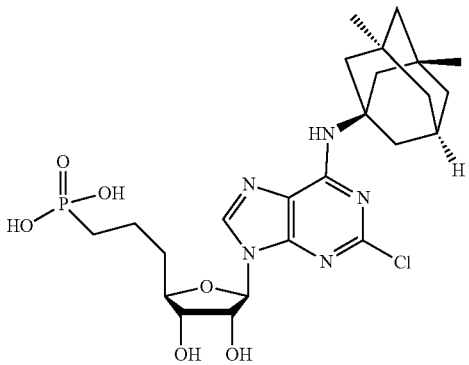 |
| c-41 | 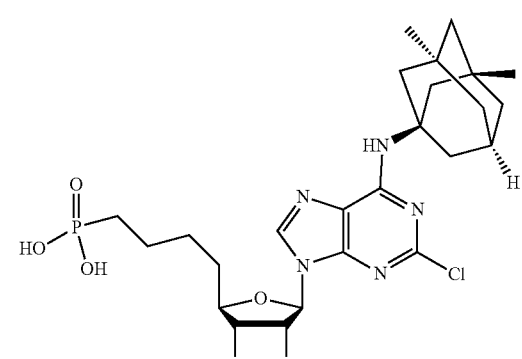 |
| c-42 | 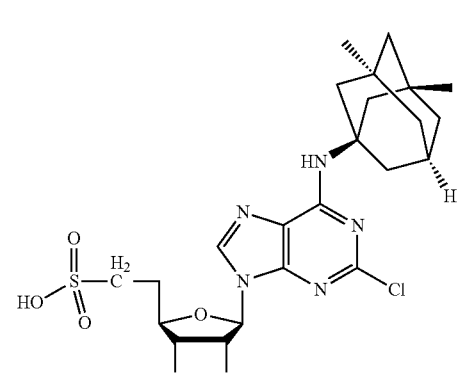 |
| c-43 | 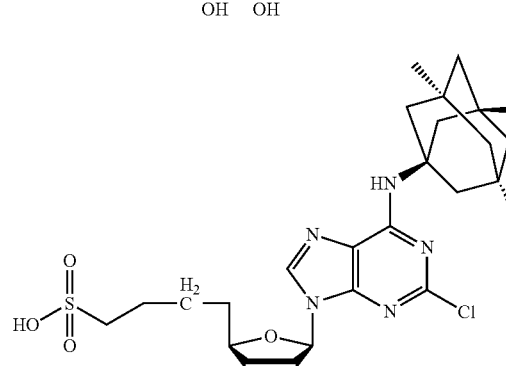 |

TABLE 1c-continued
Structures of example compounds.
| Compound Number | Structure |
|---|---|
| c-44 | 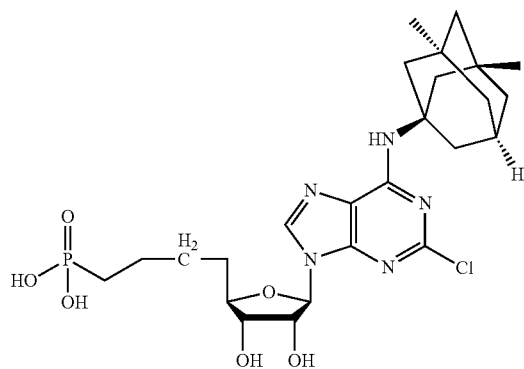 |
| c-45 | 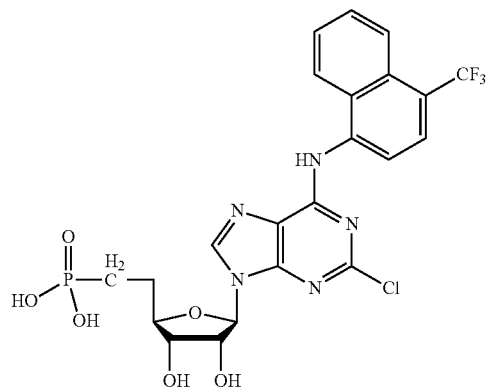 |
| c-46 | 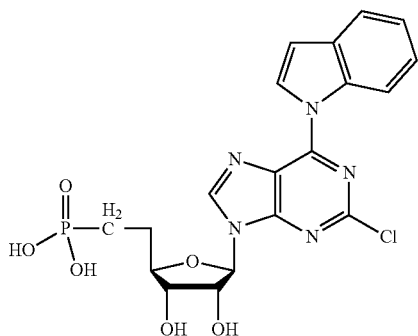 |
| c-47 | 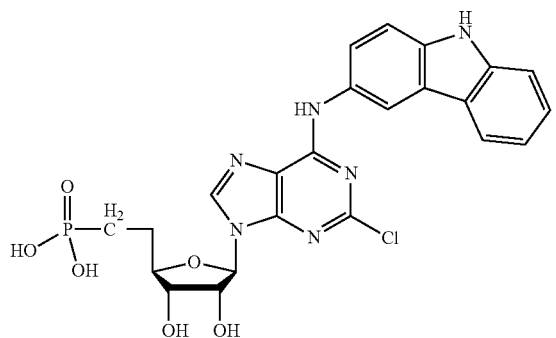 |

TABLE 1c-continued
Structures of example compounds.
| Compound Number | Structure |
|---|---|
| c-48 | 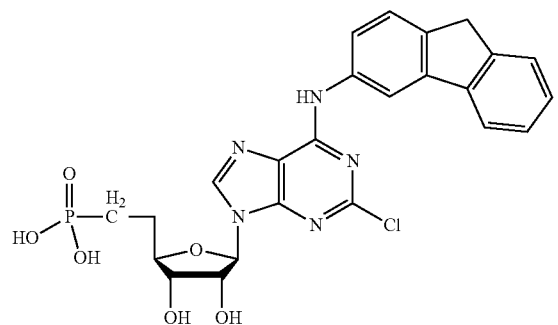 |
| c-49 | 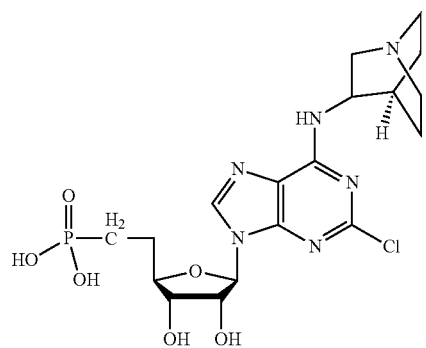 |
| c-50 | 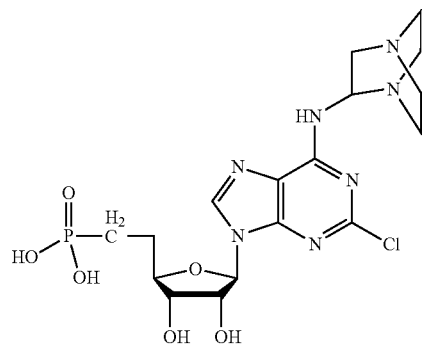 |
| c-51 | 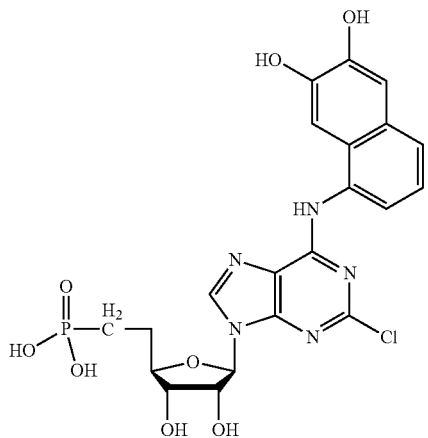 |

TABLE 1c-continued

Structures of example compounds.

| Compound Number | Structure |
|---|---|
| c-52 | 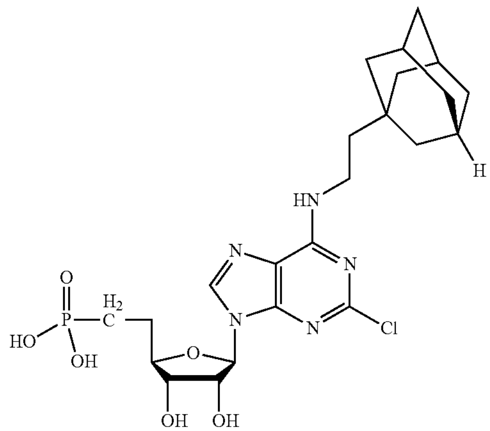 |
| c-53 | 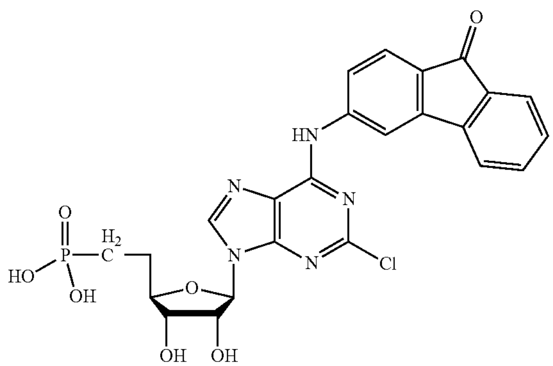 |
| c-54 | 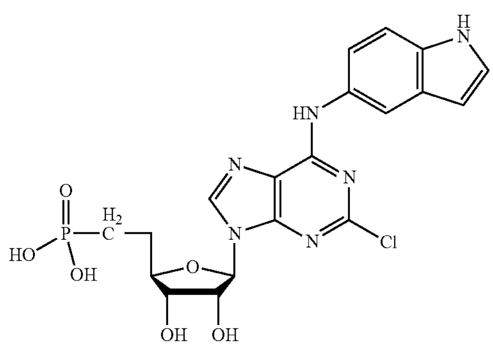 |
| c-55 | 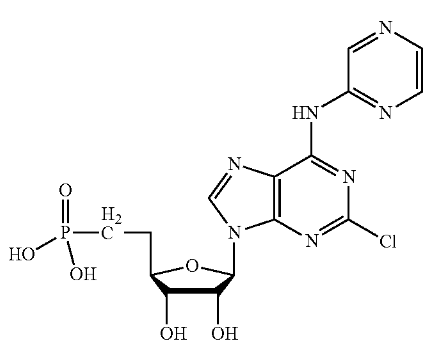 |

TABLE 1c-continued

Structures of example compounds.

| Compound Number | Structure |
|---|---|
| c-56 | 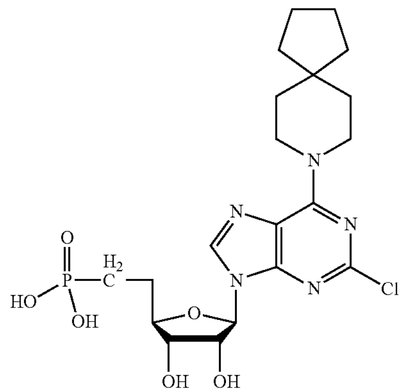 |
| c-57 | 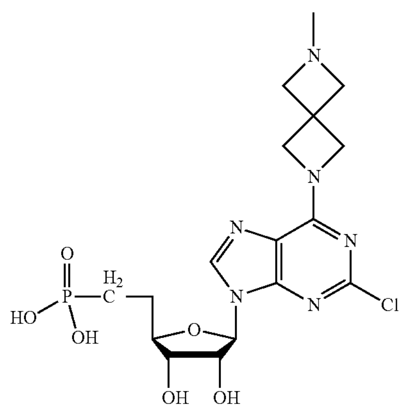 |
| c-58 | 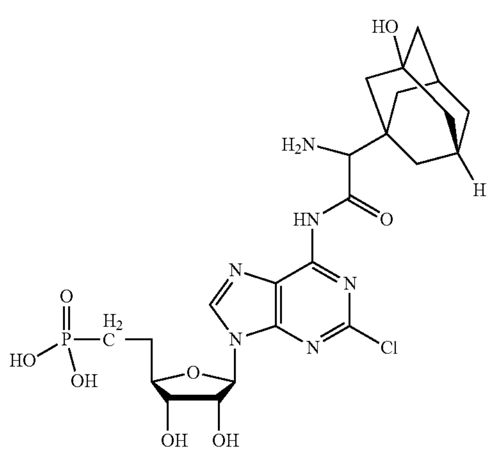 |

TABLE 1c-continued
Structures of example compounds.
| Compound Number | Structure |
|---|---|
| c-59 | 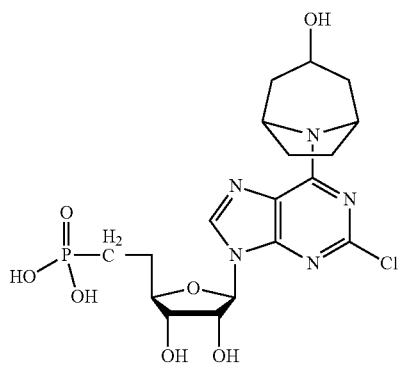 |
| c-60 | 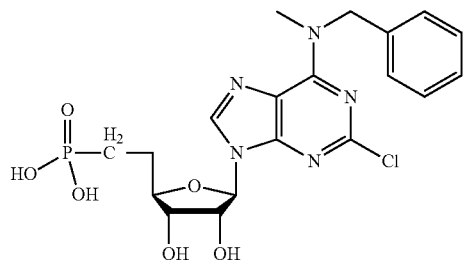 |
| c-61 | 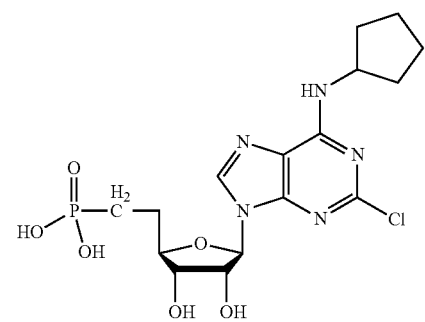 |
| c-62 | 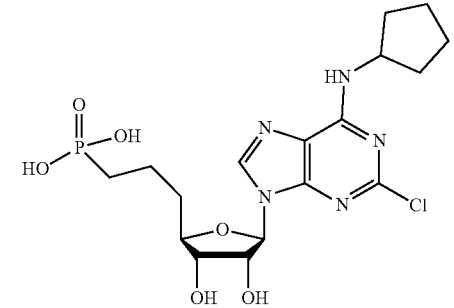 |

US 11,530,234 B2
TABLE 1c-continued
Structures of example compounds.
| Compound Number | Structure |
|---|---|
| c-63 | 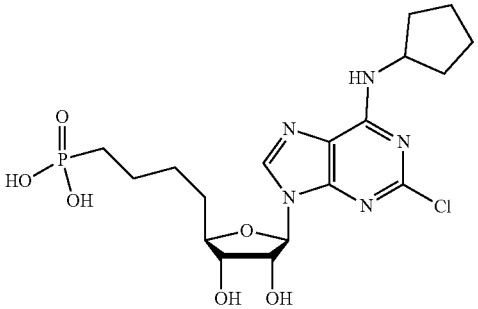 |
| c-64 | 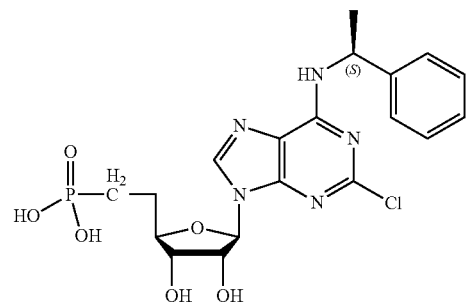 |
| c-65 | 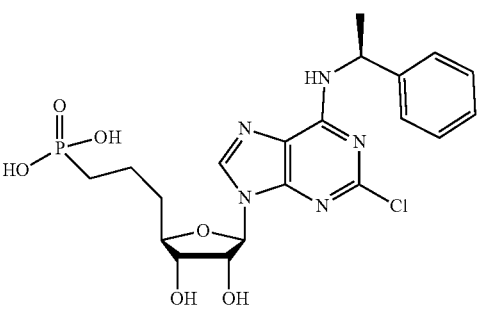 |
| c-66 | 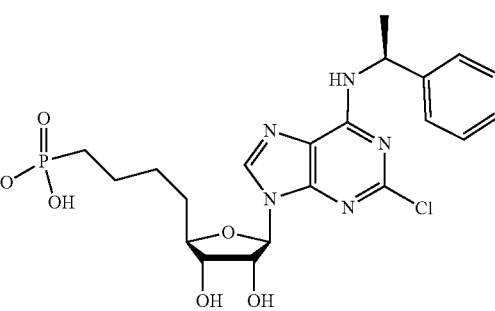 |
| c-67 | 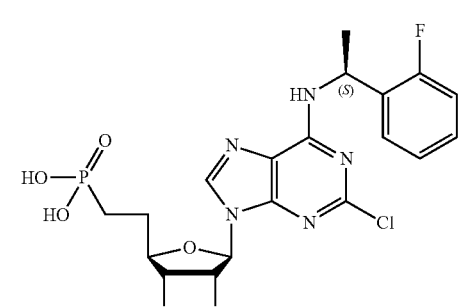 |

TABLE 1c-continued
Structures of example compounds.
| Compound Number | Structure |
|---|---|
| c-68 | 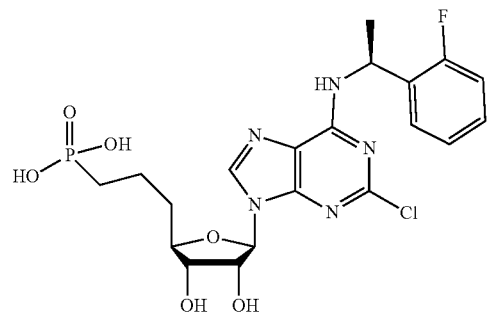 |
| c-69 | 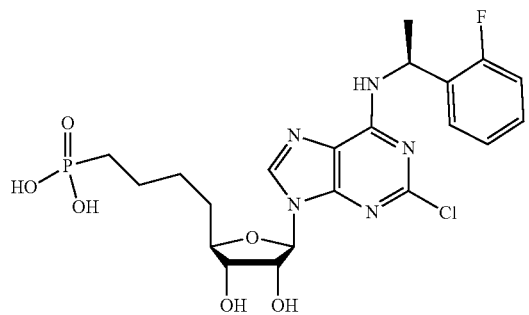 |
| c-70 | 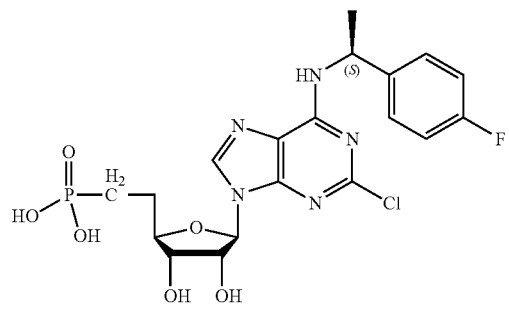 |
| c-71 | 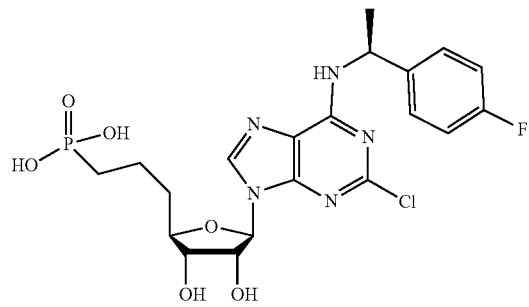 |

TABLE 1c-continued

Structures of example compounds.

| Compound Number | Structure |
|---|---|
| c-72 | 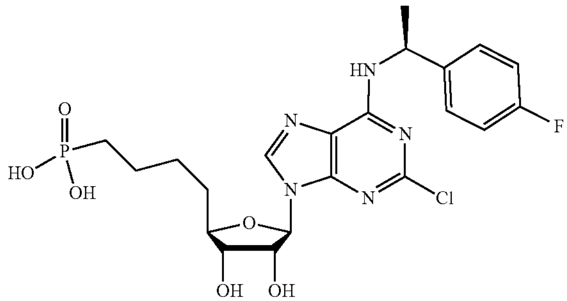 |
| c-73 | 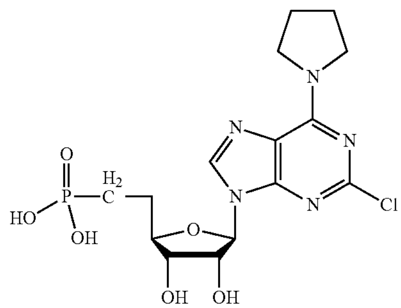 |
| c-74 | 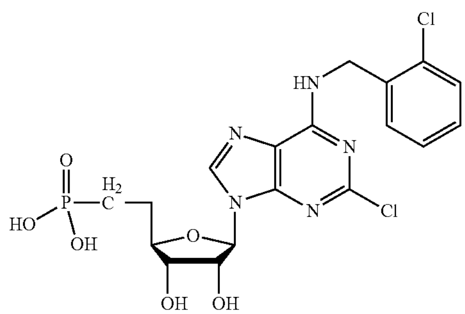 |
| c-75 | 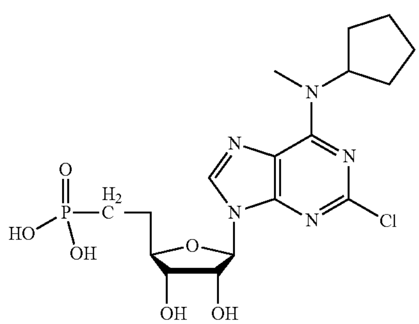 |
| c-76 | 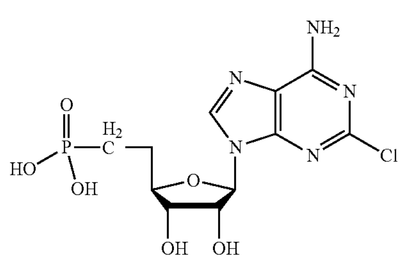 |

TABLE 1c-continued

Structures of example compounds.

| Compound Number | Structure |
| --- | --- |
| c-77 | 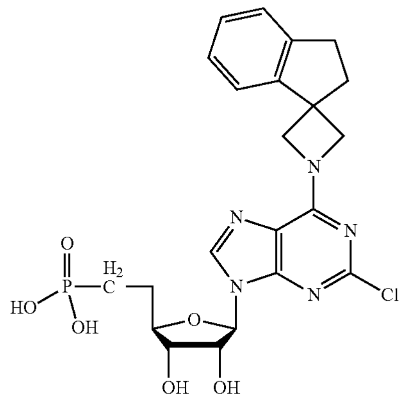 |
| c-78 | 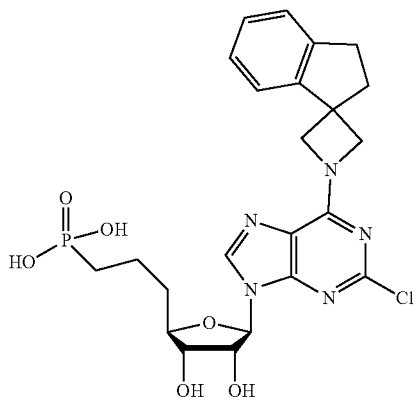 |
| c-79 | 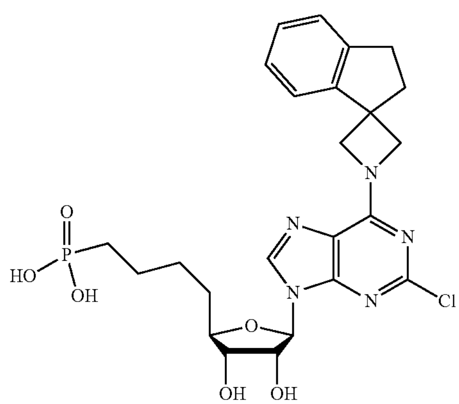 |

In some embodiments, there is provided a compound as described herein wherein the C, H, O, and N atoms in the compound are each independently selected from atoms of natural abundance and isotope-enriched atoms. Examples of isotope-enriched atoms include, without limitation, $^{12}C$, $^{13}C$, and $^{14}C$ for carbon; $^{1}H$, $^{2}H$, and $^{3}H$ for hydrogen; $^{16}O$, $^{17}O$, and $^{18}O$ for oxygen; and $^{14}N$ and $^{15}N$ for nitrogen.

In a second broad aspect, there are provided pharmaceutical compositions comprising a compound described herein, or a pharmaceutically acceptable salt or ester thereof, and a pharmaceutically acceptable carrier. In some embodiments, there are provided pharmaceutical compositions comprising a compound of any one of Formulae I to IX, or a pharmaceutically acceptable salt or ester thereof, and a pharmaceutically acceptable carrier. In some embodiments, there are provided pharmaceutical compositions comprising a compound of any one of Formulae I to IX, or a pharmaceutically acceptable salt or ester thereof, wherein, in the compound, one of $R^3$ and $R^4$ is not hydrogen or a $C_1$ to $C_{10}$ alkyl alkenyl, or alkynyl group when W is O or S. In some embodiments, there are provided pharmaceutical compositions comprising a compound shown in Tables 1, 1a, 1b, and 1c, or a pharmaceutically acceptable salt or ester, and a pharmaceutically acceptable carrier. In some embodiments, the pharmaceutically acceptable carrier comprises a cream, an emulsion, a gel, a liposome, or a nanoparticle.

In some embodiments, the pharmaceutically acceptable carrier further comprises at least one additional therapeutic agent, such as, without limitation, a chemotherapeutic agent, an immune- and/or inflammation-modulating agent, an anti-hypercholesterolemia agent, or an anti-infective agent. In an embodiment, the at least one additional therapeutic agent is an immune checkpoint inhibitor. Non-limiting examples of immune checkpoint inhibitors include ipulimumab, nivolumab and lambrolizumab.

In a third broad aspect, there are provided compounds, compositions, and methods of inhibiting CD73 activity in a subject in need thereof comprising administering to the subject an effective amount of a compound and/or a pharmaceutical composition described herein.

In particular embodiments, the compounds described herein act to inhibit the immunosuppressive activity and/or the anti-inflammatory activity of CD73, and are useful as therapeutic or prophylactic therapy when such inhibition is desired. Unless otherwise indicated, when uses of the compounds of the present invention are described herein, it is to be understood that such compounds may be in the form of a composition (e.g., a pharmaceutical composition). As used herein, the terms "CD73 inhibitor", "CD73 blocker", "adenosine by ecto-5'-nucleotidase inhibitor", "NT5E inhibitor", "5NT inhibitor" and all other related art-accepted terms are used interchangeably to refer to a compound capable of inhibiting, either directly or indirectly, the CD73 receptor in an in vitro assay, an in vivo model, and/or other assay means indicative of CD73 inhibition and potential therapeutic or prophylactic efficacy. The terms also refer to compounds that exhibit at least some therapeutic or prophylactic benefit in a human subject.

Although the compounds of the present invention are believed to have effect by inhibition of CD73, a precise understanding of the compounds' underlying mechanism of action is not required to practice the invention. For example, the compounds may also have effect, at least in part, through modulation (e.g., inhibition) of other components of the purinergic signaling pathway (e.g., CD39). The purinergic signaling system consists of transporters, enzymes and receptors responsible for the synthesis, release, action, and extracellular inactivation of (primarily) ATP and its extracellular breakdown product adenosine. Because inhibition of CD73 results in decreased adenosine production, CD73 inhibitors can be used for the treatment of diseases or disorders mediated by adenosine and its actions on adenosine receptors, including A1, A2A, A2B and A3.

For purposes of the present disclosure, the purinergic signaling process can be described as comprising the following components. The purinergic receptors (P1, P2X and P2Y), a first component, are membrane receptors that mediate various physiological functions (e.g., relaxation of gut smooth muscle) as a response to the release of ATP or adenosine; in general, all cells have the ability to release nucleotides into the extracellular environment, frequently through regulated exocytosis. The nucleoside transporters (NTs), a second component, are membrane transport proteins which transport nucleoside substrates (e.g., adenosine) across cell membranes; the extracellular concentration of adenosine can be regulated by NTs, possibly in the form of a feedback loop connecting receptor signaling with transporter function. As previously described, the ecto-nucleotidases (CD73 and CD39) hydrolyze nucleotides released into the extracellular environment and comprise a further component.

In some embodiments, there are provided methods for treating or preventing cancer in a subject (e.g., a human) comprising administering to the subject a therapeutically effective amount of at least one CD73 inhibitor compound or composition described herein. In some embodiments of such methods, the subject is administered at least one CD73 inhibitor compound or composition in an amount effective to reverse, slow or stop the progression of CD73-mediated immunosuppression. In some embodiments, the CD73-mediated immunosuppression is mediated by an antigen-presenting cell (APC).

The type of cancer or tumor that can be treated or prevented using the compounds and compositions described herein is not meant to be particularly limited. Examples of cancers and tumors that can be treated or prevented using the compounds and compositions described herein include, but are not limited to: cancers of the prostate, colorectum, pancreas, cervix, stomach, endometrium, brain, liver, bladder, ovary, testis, head, neck, skin (including melanoma and basal carcinoma), mesothelial lining, white blood cell (including lymphoma and leukemia), esophagus, breast, muscle, connective tissue, lung (including small-cell lung carcinoma and non-small-cell carcinoma), adrenal gland, thyroid, kidney, bone, glioblastoma, mesothelioma, renal cell carcinoma, gastric carcinoma, sarcoma, choriocarcinoma, cutaneous basocellular carcinoma, and testicular seminoma. In some embodiments of the present invention, the cancer is melanoma, colon cancer, pancreatic cancer, breast cancer, prostate cancer, lung cancer, leukemia, a brain tumor, lymphoma, sarcoma, ovarian cancer, or Kaposi's sarcoma.

In some embodiments, there are provided methods of treating a subject receiving a bone marrow transplant or peripheral blood stem cell transplant by administering a therapeutically effective amount of an CD73 inhibitor compound or composition sufficient to increase the delayed-type hypersensitivity reaction to tumor antigen, delay the time-to-relapse of post-transplant malignancy, increase relapse-free survival time post-transplant, and/or increase long-term post-transplant survival.

In certain embodiments, there are provided methods for treating or preventing an infective disorder (e.g., a viral infection) in a subject (e.g., a human) comprising administering to the subject a therapeutically effective amount of at least one CD73 inhibitor compound or composition provided herein. In some embodiments, the infective disorder is a viral infection (e.g., a chronic viral infection), a bacterial infection, a fungal infection, or a parasitic infection. In certain embodiments, the viral infection is human immunodeficiency virus or cytomegalovirus.

In still other embodiments, there are provided methods for treating and/or preventing immune-related diseases, disorders and conditions; diseases having an inflammatory component; as well as disorders associated with the foregoing; with at least one CD73 inhibitor compound or composition provided herein.

Other diseases, disorders and conditions that can be treated or prevented, in whole or in part, by inhibition of CD73 activity are candidate indications for the CD73 inhibitor compounds and compositions provided herein.

In some embodiments, there is further provided the use of the CD73 inhibitor compounds and compositions described herein in combination with one or more additional agents. The one or more additional agents may have some CD73-modulating activity and/or they may function through distinct mechanisms of action. In some embodiments, such agents comprise radiation (e.g., localized radiation therapy or total body radiation therapy) and/or other treatment modalities of a non-pharmacological nature. When combination therapy is utilized, the CD73 inhibitor(s) and one additional agent(s) may be in the form of a single composition or multiple compositions, and the treatment modalities can be administered concurrently, sequentially, or through some other regimen. By way of example, in some embodiments there is provided a treatment regimen wherein a radiation phase is followed by a chemotherapeutic phase. A combination therapy can have an additive or synergistic effect.

In some embodiments, there is provided the use of a CD73 inhibitor compound or composition described herein in combination with bone marrow transplantation, peripheral blood stem cell transplantation, or other types of transplantation therapy.

In particular embodiments, there is provided the use of the inhibitors of CD73 function described herein in combination with immune checkpoint inhibitors. The blockade of immune checkpoints, which results in the amplification of antigen-specific T cell responses, has been shown to be a promising approach in human cancer therapeutics. Non-limiting examples of immune checkpoints (ligands and receptors), some of which are selectively upregulated in various types of tumor cells, that are candidates for blockade include PD1 (programmed cell death protein 1); PDL1 (PD1 ligand); BTLA (B and T lymphocyte attenuator); CTLA4 (cytotoxic T-lymphocyte associated antigen 4); TIM3 (T-cell membrane protein 3); LAG3 (lymphocyte activation gene 3); A2aR (adenosine A2a receptor A2aR); and Killer Inhibitory Receptors. Non-limiting examples of immune checkpoint inhibitors include ipulimumab, nivolumab and lambrolizumab.

In other embodiments, there are provided methods for treating cancer in a subject, comprising administering to the subject a therapeutically effective amount of at least one CD73 inhibitor compound or composition thereof and at least one chemotherapeutic agent, such agents including, but not limited to alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nucleoside analogs (e.g., gemcitabine); nitroso ureas such as carmustine, lomustine, and streptozocin; topoisomerase 1 inhibitors (e.g., irinotecan); platinum complexes such as cisplatin and carboplatin; bioreductive alkylators such as mitomycin, procarbazine, dacarbazine and altretamine); DNA strand-breakage agents (e.g., bleomycin); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, estramustine, vinblastine, docetaxol, epothilone derivatives, and paclitaxel); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); and antihormonal antigens (e.g., tamoxifen, antiandrogen agents such as flutamide; and antiadrenal agents such as mitotane and aminoglutethimide). There is also provided the use of the CD73 inhibitors in combination with other agents known in the art (e.g., arsenic trioxide) and other chemotherapeutic agents that may be developed in the future.

In some embodiments drawn to methods of treating cancer, the administration of a therapeutically effective amount of a CD73 inhibitor in combination with at least one chemotherapeutic agent results in a cancer survival rate greater than the cancer survival rate observed by administering either agent alone. In further embodiments drawn to methods of treating cancer, the administration of a therapeutically effective amount of a CD73 inhibitor in combination with at least one chemotherapeutic agent results in a reduction of tumor size or a slowing of tumor growth greater than reduction of the tumor size or slowing of tumor growth observed by administration of either agent alone.

In further embodiments, there are provided methods for treating or preventing cancer in a subject, comprising administering to the subject a therapeutically effective amount of at least one CD73 inhibitor compound or composition and at least one signal transduction inhibitor (STI). In a particular embodiment, the at least one STI is selected from the group consisting of bcr/abl kinase inhibitors, epidermal growth factor (EGF) receptor inhibitors, her-2/neu receptor inhibitors, and farnesyl transferase inhibitors (FTIs).

In other embodiments, there are provided methods of augmenting the rejection of tumor cells in a subject comprising administering an CD73 inhibitor compound or composition in conjunction with at least one chemotherapeutic agent and/or radiation therapy, wherein the resulting rejection of tumor cells is greater than that obtained by administering either the CD73 inhibitor, the chemotherapeutic agent or the radiation therapy alone.

In further embodiments, there are provided methods for treating cancer in a subject, comprising administering to the subject a therapeutically effective amount of at least one CD73 inhibitor and at least one immunomodulator other than a CD73 inhibitor. It should be understood that, as used herein, a "CD73 inhibitor" refers to compounds provided herein, e.g., a compound of any one of Formulae I-IX, a compound of Table 1, or a pharmaceutically acceptable salt or ester thereof, and to pharmaceutical compositions thereof.

In some embodiments, there are provided methods of treating or preventing a CD73-associated disease, disorder or condition in a subject in need thereof, comprising administering a therapeutically effective amount of at least one CD73 inhibitor or a pharmaceutical composition thereof to the subject, such that the CD73-associated disease, disorder or condition is treated or prevented in the subject. In some embodiments, the compound is administered in an amount effective to reverse, slow or stop the progression of CD73-mediated immunosuppression in the subject.

In some embodiments, the CD73-associated disease, disorder or condition is cancer, such as, without limitation, a cancer of the prostate, colon, rectum, pancreas, cervix, stomach, endometrium, brain, liver, bladder, ovary, testis, head, neck, skin, mesothelial lining, white blood cell, esophagus, breast, muscle, connective tissue, lung, adrenal gland, thyroid, kidney, or bone. In some embodiments, the cancer is glioblastoma, mesothelioma, renal cell carcinoma, gastric carcinoma, sarcoma, choriocarcinoma, cutaneous basocellular carcinoma, or testicular seminoma. In some embodiments, the cancer is melanoma, colon cancer, pancreatic cancer, breast cancer, prostate cancer, lung cancer, leukemia, a brain tumor, lymphoma, ovarian cancer, or Kaposi's sarcoma.

In some embodiments, the CD73-associated disease, disorder or condition is an immune-related disease, disorder or condition selected from the group consisting of rheumatoid arthritis, kidney failure, lupus, asthma, psoriasis, colitis, pancreatitis, allergies, fibrosis, anemia fibromyalgia, Alzheimer's disease, congestive heart failure, stroke, aortic valve stenosis, arteriosclerosis, osteoporosis, Parkinson's disease, infections, Crohn's disease, ulcerative colitis, allergic contact dermatitis, eczema, systemic sclerosis and multiple sclerosis.

In some embodiments, methods provided herein further comprise administration of at least one additional therapeutic agent to the subject. The at least one additional therapeutic agent may be administered concomitantly or sequentially with the compound or composition described herein. In some embodiments, the at least one additional therapeutic agent is a chemotherapeutic agent, an immune- and/or inflammation-modulating agent, an anti-hypercholesterolemia agent, or an anti-infective agent. In an embodiment, the at least one additional therapeutic agent is an immune checkpoint inhibitor, such as, without limitation, ipulimumab, nivolumab or lambrolizumab.

In some embodiments, there are provided methods for treating or preventing an infective disorder (e.g., a viral infection) in a subject (e.g., a human) comprising administering to the subject a therapeutically effective amount of at least one CD73 inhibitor and a therapeutically effective amount of an anti-infective agent(s), such as one or more antimicrobial agents.

In additional embodiments, treatment of an infective disorder is effected through the co-administration of a vaccine in combination with administration of a therapeutically effective amount of a CD73 inhibitor provided herein. In some embodiments, the vaccine is an anti-viral vaccine, including, for example, an anti-HIV vaccine. In other embodiments, the vaccine is effective against tuberculosis or malaria. In still other embodiments, the vaccine is a tumor vaccine (e.g., a vaccine effective against melanoma); the tumor vaccine can comprise genetically modified tumor cells or a genetically modified cell line, including genetically modified tumor cells or a genetically modified cell line that has been transfected to express granulocyte-macrophage stimulating factor (GM-CSF). In particular embodiments, the vaccine includes one or more immunogenic peptides and/or dendritic cells.

In certain embodiments drawn to treatment of an infection by administering an CD73 inhibitor and at least one additional therapeutic agent, a symptom of infection observed after administering both the CD73 inhibitor and the additional therapeutic agent is improved over the same symptom of infection observed after administering either alone. In some embodiments, the symptom of infection observed can be reduction in viral load, increase in CD4+ T cell count, decrease in opportunistic infections, increased survival time, eradication of chronic infection, or a combination thereof.

In some embodiments, there are provided methods of treating cancer in a subject, comprising administering to the subject an effective amount of a compound or composition described herein and an immune checkpoint inhibitor, such that cancer is treated in the subject. The compound or composition described herein and the immune checkpoint inhibitor may be administered in combination or sequentially. The compound or composition may be administered after the immune checkpoint inhibitor or prior to administration of the immune checkpoint inhibitor. In some embodiments, the compound or composition and/or the immune checkpoint inhibitor are administered prior to, concurrent with, or subsequent to, other anti-cancer treatment such as, without limitation, radiation treatment. In some embodiments, the immune checkpoint inhibitor is selected from the group consisting of ipulimumab, nivolumab and lambrolizumab.

In a fourth broad aspect, there are provided kits comprising the compound or composition described herein. Kits may further comprise a buffer or excipient, and/or instructions for use. In some embodiments, kits further comprise at least one additional therapeutic agent, such as without limitation a chemotherapeutic agent, an immune- and/or inflammation-modulating agent, an anti-hypercholesterolemia agent, an anti-infective agent, or an immune checkpoint inhibitor.

BRIEF DESCRIPTION OF THE DRAWINGS

For a better understanding of the invention and to show more clearly how it may be carried into effect, reference will now be made by way of example to the accompanying drawings, which illustrate aspects and features according to embodiments of the present invention, and in which.

DETAILED DESCRIPTION

Figure 1:
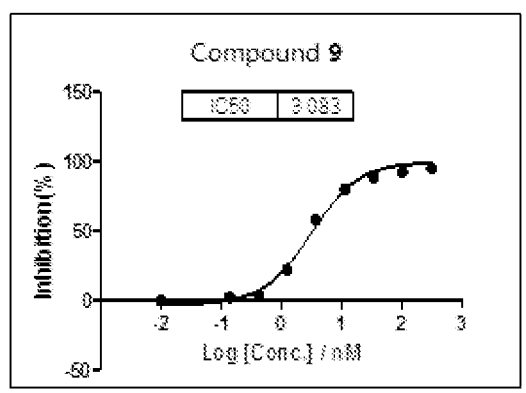
FIG. 1 is a graph showing the CD73 inhibition rate (% Inhibition vs. Log[Conc.]/nM) for compound 9.
Figure 2:
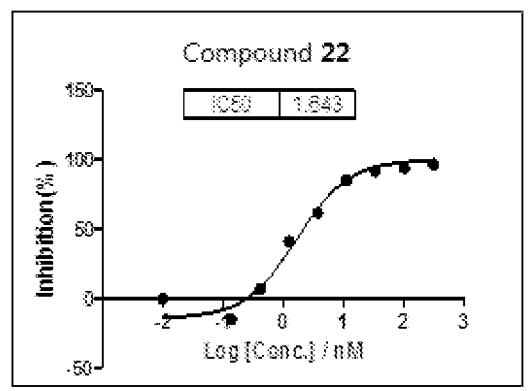
FIG. 2 is a graph showing the CD73 inhibition rate for compound 22.

The number of subjects diagnosed with cancer and the number of deaths attributable to cancer continue to rise. Traditional treatment approaches comprising chemotherapy and radiotherapy are generally difficult for the subject to tolerate and become less effective as cancers (e.g., tumors) evolve to circumvent such treatments. Recent experimental evidence indicates that CD73 inhibitors may represent an important new treatment modality for cancer (e.g., breast cancer) treatment.

Promising data also support the role of inhibitors of CD73 function to inhibit the anti-inflammatory activity of CD73 and/or the immunosuppressive activity of CD73, and thus CD73 inhibitors may be useful to treat, for example, immunosuppressive diseases (e.g., HIV and AIDs). Inhibition of CD73 may also be an important treatment strategy for subjects with neurological or neuropsychiatric diseases or disorders such as depression.

There are provided herein, inter alia, small molecule compounds having CD73 inhibitory activity, as well as compositions thereof, and methods of using the compounds and compositions for the treatment and prevention of the diseases, disorders and conditions described herein. Compounds provided herein are useful as inhibitors of CD73 and, therefore, useful in the treatment of diseases, disorders, and conditions in which CD73 activity plays a role. Additionally, the compounds provided herein may be useful as inhibitors of adenosine receptors such as, for example, the $A_2A$ receptor. Accordingly, the compounds provided herein are useful in the treatment of diseases, disorders, and conditions associated with activity of one or more adenosine receptors.

In an embodiment, there is provided herein a method of treating a subject (e.g., a human) with cancer or a disorder mediated by CD73 comprising the step of administering to the subject a therapeutically effective amount of an CD73 inhibitor provided herein, e.g., a compound provided herein or a pharmaceutically acceptable composition thereof.

It should be understood that a pharmaceutical composition comprises a compound disclosed herein (or a pharmaceutically acceptable salt or ester thereof) and a pharmaceutically acceptable carrier, adjuvant, or vehicle. In certain embodiments, the amount of a compound in a composition is such that it is effective as an inhibitor of CD73 in a biological sample (e.g., in an in vitro assay, in an in vivo model, etc.) or in a subject. In certain embodiments, the composition is formulated for administration to a subject in need of such composition. In some embodiments, the composition is an injectable formulation. In other embodiments, the composition is formulated for oral administration to a subject.

There is also provided a method of treating a subject (e.g., a human) with cancer or a disorder mediated by an adenosine receptor (e.g., $A_2AR$) comprising the step of administering to the subject a therapeutically effective amount of an CD73 inhibitor provided herein, e.g., a compound provided herein or a pharmaceutically acceptable composition thereof. In certain embodiments, the amount of a compound in a composition is such that it is effective as an inhibitor of an adenosine receptor (e.g., $A_2AR$) in a biological sample (e.g., in an in vitro assay, in an in vivo model, etc.) or in a subject. In certain embodiments, the composition is formulated for administration to a subject in need of such composition. In some embodiments, the composition is an injectable formulation. In other embodiments, the composition is formulated for oral administration to a subject. In some embodiments, the composition is in the form of a hard shell gelatin capsule, a soft shell gelatin capsule, a cachet, a pill, a tablet, a lozenge, a powder, a granule, a pellet, a pastille, or a dragee. In some embodiments, the composition is in the form of a solution, an aqueous liquid suspension, a non-aqueous liquid suspension, an oil-in-water liquid emulsion, a water-in-oil liquid emulsion, an elixir, or a syrup. In some embodiments, the composition is enteric coated. In some embodiments, the composition is formulated for controlled release.

In further embodiments, there are provided methods for treating or preventing cancer in a subject, comprising administering to the subject a therapeutically effective amount of at least one CD73 inhibitor and at least one signal transduction inhibitor (STI). In a particular embodiment, the at least one STI is selected from the group consisting of bcr/abl kinase inhibitors, epidermal growth factor (EGF) receptor inhibitors, her-2/neu receptor inhibitors, and farnesyl transferase inhibitors (FTIs). There are also provided methods of augmenting the rejection of tumor cells in a subject comprising administering an CD73 inhibitor in conjunction with at least one chemotherapeutic agent and/or radiation therapy, wherein the resulting rejection of tumor cells is greater than that obtained by administering either the CD73 inhibitor, the chemotherapeutic agent or the radiation therapy alone. In further embodiments, there are provided methods for treating cancer in a subject, comprising administering to the subject a therapeutically effective amount of at least one CD73 inhibitor and at least one immunomodulator other than a CD73 inhibitor.

In other embodiments, there are provided methods for treating or preventing an infective disorder (e.g., a viral infection) in a subject (e.g., a human) comprising administering to the subject a therapeutically effective amount of at least one CD73 inhibitor and a therapeutically effective amount of an anti-infective agent(s), such as one or more antimicrobial agents.

In additional embodiments, treatment of an infective disorder is effected through the co-administration of a vaccine in combination with administration of a therapeutically effective amount of an CD73 inhibitor provided herein. In some embodiments, the vaccine is an anti-viral vaccine, including, for example, an anti-HIV vaccine. In other embodiments, the vaccine is effective against tuberculosis or malaria. In still other embodiments, the vaccine is a tumor vaccine (e.g., a vaccine effective against melanoma); the tumor vaccine can comprise genetically modified tumor cells or a genetically modified cell line, including genetically modified tumor cells or a genetically modified cell line that has been transfected to express granulocyte-macrophage stimulating factor (GM-CSF). In particular embodiments, the vaccine includes one or more immunogenic peptides and/or dendritic cells.

In certain embodiments drawn to treatment of an infection by administering an CD73 inhibitor and at least one additional therapeutic agent, a symptom of infection observed after administering both the CD73 inhibitor and the additional therapeutic agent is improved over the same symptom of infection observed after administering either alone. In some embodiments, the symptom of infection observed can be reduction in viral load, increase in CD4+ T cell count, decrease in opportunistic infections, increased survival time, eradication of chronic infection, or a combination thereof.

Definitions

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "about" is used to indicate that a value includes an inherent variation of error for the device or the method being employed to determine the value.

The term "derivative" as used herein, is understood as being a substance similar in structure to another compound but differing in some slight structural detail.

The present description refers to a number of chemical terms and abbreviations used by those skilled in the art. Nevertheless, definitions of selected terms are provided for clarity and consistency.

As used herein, the term "alkyl" refers to saturated hydrocarbons having from one to thirty carbon atoms, including linear, branched, and cyclic alkyl groups. Examples of alkyl groups include, without limitation, methyl, ethyl, propyl, butyl, pentyl, hexyl, heptyl, octyl, nonyl, decyl, isopropyl, tert-butyl, sec-butyl, isobutyl, cyclopropyl, cyclopentyl, cyclohexyl, cycloheptyl, cyclooctyl, and the like. The term alkyl includes both unsubstituted alkyl groups and substituted alkyl groups. The terms "$C_1$-$C_n$alkyl" and "$C_{1-n}$ alkyl", wherein n is an integer from 2 to 30, are used interchangeably to refer to an alkyl group having from 1 to the indicated "n" number of carbon atoms. Alkyl residues may be substituted or unsubstituted. In some embodiments, for example, alkyl may be substituted by hydroxyl, amino, carboxyl, carboxylic ester, amide, carbamate, or aminoalkyl. In some particular embodiments, "alkyl" is modified by a range of the number of carbon atoms and thus the size of the alkyl group is defined specifically. For example, a $C_{11}$-$C_{30}$ alkyl specifies an alkyl group containing at least 11 carbon atoms and not more than 30 carbon atoms.

As used herein, the term "acyclic" refers to an organic moiety without a ring system. The term "aliphatic group" includes organic moieties characterized by straight or branched-chains, typically having between 1 and 15 carbon atoms. Aliphatic groups include non-cyclic alkyl groups, alkenyl groups, and alkynyl groups.

As used herein, the term "alkenyl" refers to unsaturated hydrocarbons having from two to thirty carbon atoms, including linear, branched, and cyclic non aromatic alkenyl groups, and comprising between one to six carbon-carbon double bonds. Examples of alkenyl groups include, without limitation, vinyl, allyl, 1-propen-2-yl, 1-buten-3-yl, 1-buten-4-yl, 2-buten-4-yl, 1-penten-5-yl, 1,3-pentadien-5-yl, cyclopentenyl, cyclohexenyl, ethylcyclopentenyl, ethylcylohexenyl, and the like. The term alkenyl includes both unsubstituted alkenyl groups and substituted alkenyl groups. The terms "$C_2$-$C_n$alkenyl" and "$C_{2-n}$ alkenyl", wherein n is an integer from 3 to 30, are used interchangeably to refer to an alkenyl group having from 2 to the indicated "n" number of carbon atoms. In some particular embodiments, "alkenyl" is modified by a range of the number of carbon atoms and thus the size of the alkenyl group is defined specifically. For example, a $C_{11}$-$C_{30}$ alkenyl specifies an alkenyl group containing at least 11 carbon atoms and not more than 30 carbon atoms.

As used herein, the term "alkynyl" refers to unsaturated hydrocarbons having from two to thirty carbon atoms, including linear, branched, and cyclic non aromatic alkynyl groups, and comprising between one to six carbon-carbon triple bonds. Examples of alkynyl groups include, without limitation, ethynyl, 1-propyn-3-yl, 1-butyn-4-yl, 2-butyn-4-yl, 1-pentyn-5-yl, 1,3-pentadiyn-5-yl, and the like. The term alkynyl includes both unsubstituted alkynyl groups and substituted alkynyl groups. The terms "$C_2$-$C_n$alkynyl" and "$C_{2-n}$ alkynyl", wherein n is an integer from 3 to 30, are used interchangeably to refer to an alkynyl group having from 2 to the indicated "n" number of carbon atoms. In some particular embodiments, "alkynyl" is modified by a range of the number of carbon atoms and thus the size of the alkynyl group is defined specifically. For example, a $C_{11}$-$C_{30}$ alkynyl specifies an alkynyl group containing at least 11 carbon atoms and not more than 30 carbon atoms.

Unless the number of carbons is otherwise specified, "lower" as in "lower aliphatic," "lower alkyl," "lower alkenyl," and "lower alkylnyl", as used herein means that the moiety has at least one (two for alkenyl and alkynyl) and equal to or less than 6 carbon atoms.

The terms "cycloalkyl", "alicyclic", "carbocyclic" and equivalent expressions refer to a group comprising a saturated or partially unsaturated carbocyclic ring in a single, spiro (sharing one atom), or fused (sharing at least one bond) carbocyclic ring system having from three to fifteen ring members. Examples of cycloalkyl groups include, without limitation, cyclopropyl, cyclobutyl, cyclopentyl, cyclopenten-1-yl, cyclopenten-2-yl, cyclopenten-3-yl, cyclohexyl, cyclohexen-1-yl, cyclohexen-2-yl, cyclohexen-3-yl, cycloheptyl, bicyclo[4,3,0]nonanyl, norbornyl, and the like. The term cycloalkyl includes both unsubstituted cycloalkyl groups and substituted cycloalkyl groups. The terms "$C_3$-$C_n$cycloalkyl" and "$C_{3-n}$ cycloalkyl", wherein n is an integer from 4 to 15, are used interchangeably to refer to a cycloalkyl group having from 3 to the indicated "n" number of carbon atoms in the ring structure. Unless the number of carbons is otherwise specified, "lower cycloalkyl" groups as herein used, have at least 3 and equal to or less than 8 carbon atoms in their ring structure.

Cycloalkyl residues can be saturated or contain one or more double bonds within the ring system. In particular they can be saturated or contain one double bond within the ring system. In unsaturated cycloalkyl residues the double bonds can be present in any suitable positions. Monocycloalkyl residues are, for example, cyclopropyl, cyclobutyl, cyclopentyl, cyclopentenyl, cyclohexyl, cyclohexenyl, cycloheptyl, cycloheptenyl, cyclooctyl, cyclononyl, cyclodecyl, cycloundecyl, cyclododecyl or cyclotetradecyl, which can also be substituted, for example by $C_{1-4}$ alkyl. Examples of substituted cycloalkyl residues are 4-methylcyclohexyl and 2,3-dimethylcyclopentyl. Examples of parent structures of bicyclic ring systems are norbornane, bicyclo[2.2.1]heptane, bicyclo[2.2.2]octane and bicyclo[3.2.1]octane.

The term "heterocycloalkyl" and equivalent expressions refers to a group comprising a saturated or partially unsaturated carbocyclic ring in a single, spiro (sharing one atom), or fused (sharing at least one bond) carbocyclic ring system having from three to fifteen ring members, including one to six heteroatoms (e.g., N, O, S, P) or groups containing such heteroatoms (e.g., NH, NRx (Rx is alkyl, acyl, aryl, heteroaryl or cycloalkyl), $PO_2$, SO, $SO_2$, and the like). Heterocycloalkyl groups may be C-attached or heteroatom-attached (e.g., via a nitrogen atom) where such is possible. Examples of heterocycloalkyl groups include, without limitation, pyrrolidino, tetrahydrofuranyl, tetrahydrodithienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3,1,0]hexanyl, 3-azabicyclo[4,1,0]heptanyl, 3H-indolyl, quinolizinyl, and sugars, and the like. The term heterocycloalkyl includes both unsubstituted heterocycloalkyl groups and substituted heterocycloalkyl groups. The terms "$C_3$-$C_n$heterocycloalkyl" and "$C_{3-n}$ heterocycloalkyl", wherein n is an integer from 4 to 15, are used interchangeably to refer to a heterocycloalkyl group having from 3 to the indicated "n" number of atoms in the ring structure, including at least one hetero group or atom as defined above. Unless the number of carbons is otherwise specified, "lower heterocycloalkyl" groups as herein used, have at least 3 and equal to or less than 8 carbon atoms in their ring structure.

The terms "aryl" and "aryl ring" refer to aromatic groups having "4n+2" (pi) electrons, wherein n is an integer from 1 to 7, in a conjugated monocyclic or polycyclic system (fused or not) and having six to fourteen ring atoms. A polycyclic ring system includes at least one aromatic ring. Aryl may be directly attached, or connected via a $C_1$-$C_6$ alkyl group (also referred to as arylalkyl or aralkyl). Examples of aryl groups include, without limitation, phenyl, benzyl, phenetyl, 1-phenylethyl, tolyl, naphthyl, biphenyl, terphenyl, indenyl, benzocyclooctenyl, benzocycloheptenyl, azulenyl, acenaphthylenyl, fluorenyl, phenanthernyl, anthracenyl, and the like. The term aryl includes both unsubstituted aryl groups and substituted aryl groups. The terms "$C_6$-$C_n$aryl" and "$C_{6-n}$ aryl", wherein n is an integer from 6 to 30, are used interchangeably to refer to an aryl group having from 6 to the indicated "n" number of atoms in the ring structure, including at least one hetero group or atom as defined above.

The terms "heteroaryl" and "heteroaryl ring" refer to an aromatic group having "4n+2" (pi) electrons, wherein n is an integer from 1 to 7, in a conjugated monocyclic or polycyclic system (fused or not) and having five to fourteen ring members, including one to six heteroatoms (e.g. N, O, S) or groups containing such heteroatoms (e.g. NH, NRx (Rx is alkyl, acyl, aryl, heteroaryl or cycloalkyl), SO, and the like). A polycyclic ring system includes at least one heteroaromatic ring. Heteroaryls may be directly attached, or connected via a $C_1$-$C_3$alkyl group (also referred to as heteroarylalkyl or heteroaralkyl). Heteroaryl groups may be C-attached or heteroatom-attached (e.g., via a nitrogen atom), where such is possible. Examples of heteroaryl groups include, without limitation, pyridyl, imidazolyl, pyrimidinyl, pyrazolyl, triazolyl, tetrazolyl, furyl, thienyl; isooxazolyl, thiazolyl, oxazolyl, isothiazolyl, pyrrollyl, quinolinyl, isoquinolinyl, indolyl, isoindolyl, chromenyl, isochromenyl, benzimidazolyl, benzofuranyl, cinnolinyl, indazolyl, indolizinyl, phthalazinyl, pyridazinyl, pyrazinyl, triazinyl, isoindolyl, pteridinyl, purinyl, oxadiazolyl, thiadiazolyl, furazanyl, benzofurazanyl, benzothiophenyl, benzothienyl, benzothiazolyl, benzoxazolyl, quinazolinyl, quinolizinyl, quinolonyl, isoquinolonyl, quinoxalinyl, naphthyridinyl, furopyridinyl, carbazolyl, phenanthridinyl, acridinyl, perimidinyl, phenanthrolinyl, phenazinyl, phenothiazinyl, phenoxazinyl, dibenzofuranyl, and the like. The term heteroaryl includes both unsubstituted heteroaryl groups and substituted heteroaryl groups. The terms "$C_5$-$C_n$heteroaryl" and "$C_{5-n}$ heteroaryl", wherein n is an integer from 6 to 29, are used interchangeably to refer to a heteroaryl group having from 5 to the indicated "n" number of atoms in the ring structure, including at least one hetero group or atom as defined above.

The terms "heterocycle" or "heterocyclic" include heterocycloalkyl and heteroaryl groups. Examples of heterocycles include, without limitation, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4αH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl, and the like. The term heterocycle includes both unsubstituted heterocyclic groups and substituted heterocyclic groups.

The term "amine" or "amino," as used herein, refers to an unsubstituted or substituted moiety of the formula —NRaRb, in which Ra and Rb are each independently hydrogen, alkyl, aryl, or heterocyclyl, or Ra and Rb, taken together with the nitrogen atom to which they are attached, form a heterocyclic ring. The term amino includes compounds or moieties in which a nitrogen atom is covalently bonded to at least one carbon or heteroatom. Thus, the terms "alkylamino" and "dialkylamino" as used herein mean an amine group having respectively one and at least two $C_1$-$C_6$alkyl groups attached thereto. The terms "arylamino" and "diarylamino" include groups wherein the nitrogen is bound to at least one or two aryl groups, respectively. The terms "amide" or "aminocarbonyl" include compounds or moieties which contain a nitrogen atom which is bound to the carbon of a carbonyl or a thiocarbonyl group. The term "acylamino" refers to an amino group directly attached to an acyl group as defined herein.

The term "bicycle" or "bicyclic" refers to a ring system with two rings that has two ring carbon atoms in common, and which can be located at any position along either ring, generally referring to bicyclic hydrocarbon radical, bicyclic aromatic carbon atom ring structure radical, and a saturated or partially unsaturated bicyclic carbon atom ring structure radical in which one or more carbon atom ring members have been replaced, where allowed by structural stability, with a heteroatom, such as an O, S or N atom. The bicyclic system can be a fused-ring system, such as bicyclo[4.4.0]decane or naphthalene, or a bridged-ring system, such as bicyclo[2.2.2]octane.

The term "tricycle" or "tricyclic" refers to a ring system with three rings that has three ring carbon atoms in common, and which can be located at any position along each ring; generally referring to tricyclic hydrocarbon radical, tricyclic aromatic carbon atom ring structure radical, and a saturated or partially unsaturated tricyclic carbon atom ring structure radical in which one or more carbon atom ring members have been replaced, where allowed by structural stability, with a heteroatom, such as an O, S or N atom. A tricyclic system can have three rings arranged as a fused ring, such as anthracene or tetradecahydroanthracene, or a bridged ring, such as in adamantine or tricycle[3.3.1.1]decane.

The term "multi-cycle", "multicycle", "multi-cyclic", or "multi-cyclic" means a ring system with more than three rings having more than three ring carbon atoms in common, and which can be located at any position along either ring. The term generally refers to a multicyclic hydrocarbon radical, a multicyclic aromatic carbon atom ring structure radical, and a saturated or partially unsaturated multicyclic carbon atom ring structure radical in which one or more carbon atom ring members have been replaced, where allowed by structural stability, with a heteroatom, such as an O, S or N atom.

The term "fused ring" or "fused" refers to a polycyclic ring system that contains fused rings. Typically, a fused ring system contains 2 or 3 rings and/or up to 18 ring atoms. As defined above, cycloalkyl radicals, aryl radicals and heterocyclyl radicals may form fused ring systems. Thus, a fused ring system may be aromatic, partially aromatic or not aromatic and may contain heteroatoms. A spiro ring system is not a fused-polycyclic by this definition, but fused polycyclic ring systems of the invention may themselves have spiro rings attached thereto via a single ring atom of the system. Examples of fused ring systems include, but are not limited to, naphthyl (e.g. 2-naphthyl), indenyl, fenanthryl, anthracyl, pyrenyl, benzimidazole, benzothiazole, etc.

The term "spiral ring" or "spiral" refers to an organic compound, that presents a twisted structure of two or more rings (a ring system), in which 2 or 3 rings are linked together by one common atom. Spiro compounds may be fully carbocyclic (all carbon), such as without limitation spiro[5.5]undecane or heterocyclic (having one or more non-carbon atom), including but not limited to carbocyclic spiro compounds, heterocyclic spiro compounds and polyspiro compounds.

The term "bridged ring" or "bridged" refers to a carbocyclic or heterocyclic moiety where two or more atoms are shared between two or more ring structures, where any such shared atom is C, N, S, or other heteroatom arranged in a chemically reasonable substitution pattern. Alternatively, a "bridged" compound also refers to a carbocyclic or heterocyclic ring structure where one atom at any position of a primary ring is bonded to a second atom on the primary ring through either a chemical bond or atom (s) other than a bond which does (do) not comprise a part of the primary ring structure. The first and second atom may or may not be adjacent to one another in the primary ring. Illustrated below are specific non-limiting examples of bridged ring structures contemplated herein. Other carbocyclic or heterocyclic bridged ring structures are also contemplated, including bridged rings wherein the bridging atoms are C or heteroatom (s) arranged in chemically reasonable substitution patterns, as are known in the art.

The term "nitro" means —$NO_2$; the terms "halo" and "halogen" refer to bromine, chlorine, fluorine or iodine substituents; the terms "thiol", "thio", and "mercapto" mean —SH; and the terms "hydroxyl" and "hydroxy" mean —OH. The term "alkylthio" refers to an alkyl group, having a sulfhydryl group attached thereto. Suitable alkylthio groups include groups having 1 to about 12 carbon atoms, preferably from 1 to about 6 carbon atoms. The term "alkylcarboxyl" as used herein means an alkyl group having a carboxyl group attached thereto.

The terms "alkoxy" and "lower alkoxy" as used herein mean an alkyl group having an oxygen atom attached thereto. Representative alkoxy groups include groups having 1 to about 6 carbon atoms, e.g., methoxy, ethoxy, propoxy, tert-butoxy and the like. Examples of alkoxy groups include methoxy, ethoxy, isopropyloxy, propoxy, butoxy, pentoxy, fluoromethoxy, difluoromethoxy, trifluoromethoxy, chloromethoxy, dichloromethoxy, trichloromethoxy groups, and the like. The term "alkoxy" includes both unsubstituted or substituted alkoxy groups, etc., as well as perhalogenated alkyloxy groups.

The terms "carbonyl" and "carboxy" include compounds and moieties which contain a carbon connected with a double bond to an oxygen atom. Examples of moieties which contain a carbonyl include aldehydes, ketones, carboxylic acids, amides, esters, anhydrides, etc.

The term "acyl" refers to a carbonyl group that is attached through its carbon atom to a hydrogen (i.e., formyl), an aliphatic group (e.g., $C_1$-$C_{29}$ alkyl, $C_1$-$C_{29}$ alkenyl, $C_1$-$C_{29}$ alkynyl, e.g., acetyl), a cycloalkyl group ($C_3$-$C_8$cycloalkyl), a heterocyclic group ($C_3$-$C_8$heterocycloalkyl and $C_5$-$C_6$heteroaryl), an aromatic group ($C_6$aryl, e.g., benzoyl), and the like. Acyl groups may be unsubstituted or substituted acyl groups (e.g., salicyloyl).

It should be understood that "substitution" or "substituted with" includes the implicit proviso that such substitution is in accordance with the permitted valence of the substituted atom and the substituent, and that the substitution results in a stable compound, i.e., a compound which does not spontaneously undergo transformation such as by rearrangement, cyclization, elimination, etc. As used herein, the term "substituted" is meant to include all permissible substituents of organic compounds. In a broad aspect, the permissible substituents include acyclic and cyclic, branched and unbranched, carbocyclic and heterocyclic, aromatic and nonaromatic substituents of organic compounds. The permissible substituents can be one or more. The term "substituted", when used in association with any of the foregoing groups refers to a group substituted at one or more position with substituents such as acyl, amino (including simple amino, mono and dialkylamino, mono and diarylamino, and alkylarylamino), acylamino (including carbamoyl, and ureido), alkylcarbonyloxy, arylcarbonyloxy, alkoxycarbonyloxy, alkoxycarbonyl, carboxy, carboxylate, aminocarbonyl, mono and dialkylaminocarbonyl, cyano, azido, halogen, hydroxyl, nitro, trifluoromethyl, thio, alkylthio, arylthio, alkylthiocarbonyl, thiocarboxylate, lower alkyl, lower alkenyl, lower alkynyl, cycloalkyl, heterocycloalkyl, aryl, heteroaryl, lower alkoxy, aryloxy, aryloxycarbonyloxy, benzyloxy, benzyl, sulfinyl, alkylsulfinyl, sulfonyl, sulfate, sulfonate, sulfonamide, phosphate, phosphonato, phosphinato, oxo, guanidine, imino, formyl and the like. Any of the above substituents can be further substituted if permissible, e.g., if the group contains an alkyl group, an aryl group, or other.

The term "solvate" refers to a physical association of a compound with one or more solvent molecules, whether organic or inorganic. This physical association includes hydrogen bonding. In certain instances, a solvate will be capable of isolation, for example when one or more solvent molecules are incorporated in the crystal lattice of a crystalline solid. "Solvate" encompasses both solution-phase and isolable solvates. Exemplary solvates include, without limitation, hydrates, ethanolates, methanolates, hemiethanolates, and the like.

A "pharmaceutically acceptable salt" of a compound means a salt of a compound that is pharmaceutically acceptable. Desirable are salts of a compound that retain or improve the biological effectiveness and properties of the free acids and bases of the parent compound as defined herein or that take advantage of an intrinsically basic, acidic or charged functionality on the molecule and that are not biologically or otherwise undesirable. Examples of pharmaceutically acceptable salts are also described, for example, in Berge et al., "Pharmaceutical Salts", J. Pharm. Sci. 66, 1-19 (1977). Non-limiting examples of such salts include:

(1) acid addition salts, formed on a basic or positively charged functionality, by the addition of inorganic acids such as hydrochloric acid, hydrobromic acid, hydroiodic acid, sulfuric acid, sulfamic acid, nitric acid, phosphoric acid, carbonate forming agents, and the like; or formed with organic acids such as acetic acid, propionic acid, lactic acid, oxalic, glycolic acid, pivalic acid, t-butylacetic acid, β-hydroxybutyric acid, valeric acid, hexanoic acid, cyclopentanepropionic acid, pyruvic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, cyclohexylaminosulfonic acid, benzenesulfonic acid, sulfanilic acid, 4-chlorobenzenesulfonic acid, 2-naphthalenesulfonic acid, 4-toluenesulfonic acid, camphorsulfonic acid, 3-phenyl propionic acid, lauryl sulphonic acid, lauryl sulfuric acid, oleic acid, palmitic acid, stearic acid, lauric acid, embonic (pamoic) acid, palmoic acid, pantothenic acid, lactobionic acid, alginic acid, galactaric acid, galacturonic acid, gluconic acid, glucoheptonic acid, glutamic acid, naphthoic acid, hydroxynapthoic acid, salicylic acid, ascorbic acid, stearic acid, muconic acid, and the like;

(2) base addition salts, formed when an acidic proton present in the parent compound either is replaced by a metal ion, including, an alkali metal ion (e.g., lithium, sodium, potassium), an alkaline earth ion (e.g., magnesium, calcium, barium), or other metal ions such as aluminum, zinc, iron and the like; or coordinates with an organic base such as ammonia, ethylamine, diethylamine, ethylenediamine, N,N'-dibenzylethylenediamine, ethanolamine, diethanolamine, triethanolamine, tromethamine, N-methylglucamine, piperazine, chloroprocain, procain, choline, lysine and the like.

Pharmaceutically acceptable salts may be synthesized from a parent compound that contains a basic or acidic moiety, by conventional chemical methods. Generally, such salts are prepared by reacting the free acid or base forms of compounds with a stoichiometric amount of the appropriate base or acid in water or in an organic solvent, or in a mixture of the two. Salts may be prepared in situ, during the final isolation or purification of a compound or by separately reacting a compound in its free acid or base form with the desired corresponding base or acid, and isolating the salt thus formed. The term "pharmaceutically acceptable salts" also include zwitterionic compounds containing a cationic group covalently bonded to an anionic group, as they are "internal salts". It should be understood that all acid, salt, base, and other ionic and non-ionic forms of compounds described herein are intended to be encompassed. For example, if a compound is shown as an acid herein, the salt forms of the compound are also encompassed. Likewise, if a compound is shown as a salt, the acid and/or basic forms are also encompassed.

Compounds provided herein may contain unnatural proportions of atomic isotopes at one or more of the atoms that constitute such compounds. Unnatural proportions of an isotope may be defined as ranging from the amount found in nature to an amount consisting of 100% of the atom in question. For example, compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere within this application. For instance, isotopic variants of the compounds of the invention may find additional utility, including but not limited to, as diagnostic and/or imaging reagents, or as cytotoxic/radiotoxic therapeutic agents. Additionally, isotopic variants can have altered pharmacokinetic and pharmacodynamic characteristics which can contribute to enhanced safety, tolerability or efficacy during treatment. All isotopic variations of compounds provided herein, whether radioactive or not, are intended to be encompassed herein.

Isotopic enrichment is a process by which the relative abundance of the isotopes of a given element are altered, thus producing a form of the element that has been enriched (i.e., increased) in one particular isotope and reduced or depleted in its other isotopic forms. As used herein, an "isotope-enriched" compound or derivative refers to a compound in which one or more specific isotopic form has been increased, i.e., one or more of the elements has been enriched (i.e., increased) in one or more particular isotope. Generally, in an isotope-enriched compound or derivative, a specific isotopic form of an element at a specific position of the compound is increased. It should be understood however that isotopic forms of two or more elements in the compound may be increased. Further, an isotope-enriched compound may be a mixture of isotope-enriched forms that are enriched for more than one particular isotope, more than one element, or both. As used herein, an "isotope-enriched" compound or derivative possesses a level of an isotopic form that is higher than the natural abundance of that form. The level of isotope-enrichment will vary depending on the natural abundance of a specific isotopic form. In some embodiments, the level of isotope-enrichment for a compound, or for an element in a compound, may be from about 2 to about 100 molar percent (%), e.g., about 2%, about 5%, about 17%, about 30%, about 51%, about 83%, about 90%, about 95%, about 96%, about 97%, about 98%, greater than about 98%, about 99%, or 100%.

As used herein, an "element of natural abundance" and an "atom of natural abundance" refers to the element or atom respectively having the atomic mass most abundantly found in nature. For example, hydrogen of natural abundance is $^1$H (protium); nitrogen of natural abundance is $^{14}$N; oxygen of natural abundance is $^{16}$O; carbon of natural abundance is $^{12}$C; and so on. A "non-isotope enriched" compound is a compound in which all the atoms or elements in the compound are isotopes of natural abundance, i.e., all the atoms or elements have the atomic mass most abundantly found in nature.

The terms "patient" and "subject" are used interchangeably herein to refer to a human or a non-human animal (e.g., a mammal).

The terms "administration", "administer" and the like, as they apply to, for example, a subject, cell, tissue, organ, or biological fluid, refer to contact of, for example, an inhibitor of CD73, a pharmaceutical composition comprising same, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", treatment" and the like refer to a course of action (such as administering an inhibitor of CD73 or a pharmaceutical composition comprising same) initiated after a disease, disorder or condition, or a symptom thereof, has been diagnosed, observed, and the like, so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering a CD73 inhibitor or a pharmaceutical composition comprising same) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof: generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The terms "therapeutically effective amount" and "effective amount" are used interchangeably herein to refer to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the serum level of a CD73 inhibitor (or, e.g., a metabolite thereof) at a particular time post-administration may be indicative of whether a therapeutically effective amount has been used. In some embodiments, the terms "therapeutically effective amount" and "effective amount" refer to the amount or dose of a therapeutic agent, such as a compound, upon single or multiple dose administration to a subject, which provides the desired therapeutic, diagnostic, or prognostic effect in the subject. An effective amount can be readily determined by an attending physician or diagnostician using known techniques and by observing results obtained under analogous circumstances. In determining the effective amount or dose of compound administered, a number of factors are considered including, but not limited to: the size, age, and general health of the subject; the specific disease involved; the degree of or involvement or the severity of the disease or condition to be treated; the response of the individual subject; the particular compound administered; the mode of administration; the bioavailability characteristics of the preparation administered; the dose regimen selected; the use of concomitant medication(s); and other relevant considerations.

The term "substantially pure" is used herein to indicate that a component makes up greater than about 50% of the total content of the composition, and typically greater than about 60% of the total content. More typically, "substantially pure" refers to compositions in which at least 75'%, at least 85%), at least 90% or more of the total composition is the component of interest. In some cases, the component of interest will make up greater than about 90%), or greater than about 95%) of the total content of the composition.

As used herein, the terms "CD73-associated disease, disorder or condition" and "disease, disorder or condition mediated by CD73" are used interchangeably to refer to any disease, disorder or condition for which treatment with a CD73 inhibitor may be beneficial. In general, CD73-associated or mediated diseases, disorders and conditions are those in which CD73 activity plays a biological, mechanistic, or pathological role. Such diseases, disorders and conditions may also be associated with activity of one or more adenosine receptors. Non-limiting examples of CD73-associated diseases, disorders and conditions include oncology-related disorders (cancers, tumors, etc.), immune-related disorders, disorders with an inflammatory component, microbial-related disorders, CNS-related and neurological disorders, and other disorders (such as, without limitation, cardiovascular, gastrointestinal, metabolic, hepatic, pulmonary, ophthalmologic, and renal disorders).

For example, a CD73 inhibitor may be used to prevent or treat a proliferative condition, cancer or tumor; to increase or enhance an immune response; to improve immunization, including increasing vaccine efficacy; and to increase inflammation. Immune deficiencies associated with immune deficiency diseases, immunosuppressive medical treatment, acute and/or chronic infection, and aging can be treated using CD73 inhibitors disclosed herein. CD73 inhibitors can also be used to stimulate the immune system of patients suffering from iatrogenically-induced immune suppression, including those who have undergone bone marrow transplants, chemotherapy, or radiotherapy. In other embodiments, a CD73 inhibitor may be used to treat or prevent any viral, bacterial, fungal, parasitic or other infective disease, disorder or condition, including without limitation HIV and AIDS.

In some embodiments, a CD73 inhibitor may be used to prevent or treat an immune-related disease, disorder or condition selected from the group consisting of rheumatoid arthritis, kidney failure, lupus, asthma, psoriasis, colitis, pancreatitis, allergies, fibrosis, anemia fibromyalgia, Alzheimer's disease, congestive heart failure, stroke, aortic valve stenosis, arteriosclerosis, osteoporosis, Parkinson's disease, infections, Crohn's disease, ulcerative colitis, allergic contact dermatitis, eczema, systemic sclerosis and multiple sclerosis.

Pharmaceutical compositions provided herein can be formulated to be compatible with the intended method or route of administration; exemplary routes of administration are set forth herein. Furthermore, the pharmaceutical compositions may be used in combination with other therapeutically active agents or compounds as described herein in order to treat or prevent the CD73-associated diseases, disorders and conditions as contemplated herein.

Pharmaceutical compositions containing the active ingredient (e.g., a CD73 inhibitor) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known in the art for the manufacture of pharmaceutical compositions, and such compositions may contain one or more agents such as, for example, sweetening agents, flavoring agents, coloring agents and preserving agents in order to provide pharmaceutically acceptable preparations. Tablets, capsules and the like generally contain the active ingredient in admixture with non-toxic pharmaceutically acceptable carriers or excipients which are suitable for the manufacture of tablets. These carriers or excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

Tablets, capsules and the like suitable for oral administration may be uncoated or coated using known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylenevinylacetate, methycellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil. Aqueous suspensions contain the active materials in admixture with excipients suitable for the manufacture thereof. Such excipients can be suspending agents, for example sodium carboxymethylcellulose, methykellulose, hydroxy-propylmethylcellulose, sodium alginate, polyvinyl-pyrrolidone, gum tragacanth and gum acacia; dispersing or wetting agents, for example a naturally-occurring phosphatide (e.g., lecithin), or condensation products of an alkylene oxide with fatty acids (e.g., polyoxyethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are known in the art.

Pharmaceutical compositions of the present invention may also be in the form of oil-in-water emulsions. The oily phase may be a vegetable oil, for example olive oil or *arachis* oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

Pharmaceutical compositions typically comprise a therapeutically effective amount of a CD84 inhibitor compound provided herein and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bi sulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-MoqJholino)ethanesulfonic acid (MES), 2-(N-Morpholino)ethanesulfonic acid sodium salt (MES), 3-(N-Morpholino)propanesulfonic acid (MOPS), and Ntris[Hydroxymethyl]methyl-3-aminopropanesulfonic acid (TAPS). After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form.

In some embodiments, the pharmaceutical composition is provided in a single-use container (e.g., a single-use vial, ampoule, syringe, or autoinjector, whereas a multi-use container (e.g., a multi-use vial) is provided in other embodiments.

Formulations can also include carriers to protect the composition against rapid degradation or elimination from the body, such as a controlled release formulation, including liposomes, hydrogels, and microencapsulated delivery systems. For example, a time delay material such as glyceryl monostearate or glyceryl stearate alone, or in combination with a wax, may be employed. Any drug delivery apparatus may be used to deliver a CD73 inhibitor, including implants (e.g., implantable pumps) and catheter systems, slow injection pumps and devices, all of which are well known to the skilled artisan.

Pharmaceutical compositions may also be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

CD73 inhibitor compounds and compositions provided herein may be administered to a subject in any appropriate manner known in the art. Suitable routes of administration include, without limitation: oral, parenteral (e.g., intramuscular, intravenous, subcutaneous (e.g., injection or implant), intraperitoneal, intracisternal, intraarticular, intraperitoneal, intracerebral (intraparenchymal) and intracerebroventricular), nasal, vaginal, sublingual, intraocular, rectal, topical (e.g., transdermal), buccal and inhalation. Depot injections, which are generally administered subcutaneously or intramuscularly, may also be utilized to release the CD73 inhibitors disclosed herein over a defined period of time. In certain embodiments, CD73 inhibitor compounds and compositions are administered orally to a subject in need thereof.

CD73 inhibitor compounds and compositions provided herein may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan. In general, dosing parameters dictate that the dosage amount be less than an amount that could be irreversibly toxic to the subject (the maximum tolerated dose (MID)) and not less than an amount required to produce a measurable effect on the subject. Such amounts are determined by, for example, the pharmacokinetic and pharmacodynamic parameters associated with ADME, taking into consideration the route of administration and other factors.

In some embodiments, an CD73 inhibitor may be administered (e.g., orally) at dosage levels of about 0.01 mg/kg to about 50 mg/kg, or about 1 mg/kg to about 25 mg/kg, of subject body weight per day, one or more times a day, to obtain the desired therapeutic effect. For administration of an oral agent, the compositions can be provided in the form of tablets, capsules and the like containing from 1.0 to 1000 milligrams of the active ingredient, particularly 1, 3, 5, 10, 15, 20, 25, 50, 75, 100, 150, 200, 250, 300, 400, 500, 600, 750, 800, 900, or 1000 milligrams of the active ingredient.

In some embodiments, the dosage of the desired CD73 inhibitor is contained in a "unit dosage form". The phrase "unit dosage form" refers to physically discrete units, each unit containing a predetermined amount of the CD73 inhibitor, either alone or in combination with one or more additional agents, sufficient to produce the desired effect. It will be appreciated that the parameters of a unit dosage form will depend on the particular agent(s) and the effect to be achieved.

There are also provided herein kits comprising a CD73 inhibitor compound or composition. Kits are generally in the form of a physical structure housing various components and may be used, for example, in practicing the methods provided herein. For example, a kit may include one or more CD73 inhibitor disclosed herein (provided in, e.g., a sterile container), which may be in the form of a pharmaceutical composition suitable for administration to a subject. The CD73 inhibitor can be provided in a form that is ready for use (e.g., a tablet or capsule) or in a form requiring, for example, reconstitution or dilution (e.g., a powder) prior to administration. When the CD73 inhibitors are in a form that needs to be reconstituted or diluted by a user, the kit may also include diluents (e.g., sterile water), buffers, pharmaceutically acceptable excipients, and the like, packaged with or separately from the CD73 inhibitors. When combination therapy is contemplated, the kit may contain several therapeutic agents separately or they may already be combined in the kit. Each component of the kit may be enclosed within an individual container, and all of the various containers may be within a single package. A kit of the present invention may be designed for conditions necessary to properly maintain the components housed therein (e.g., refrigeration or freezing).

A kit may also contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Examples

The present invention will be more readily understood by referring to the following examples, which are provided to illustrate the invention and are not to be construed as limiting the scope thereof in any manner.

Unless defined otherwise or the context clearly dictates otherwise, all technical and scientific terms used herein have the same meaning as commonly understood by one of ordinary skill in the art to which this invention belongs. It should be understood that any methods and materials similar or equivalent to those described herein can be used in the practice or testing of the invention.

Compound Synthesis

Compounds provided herein can be prepared using conventional methods and as described in the Examples below.

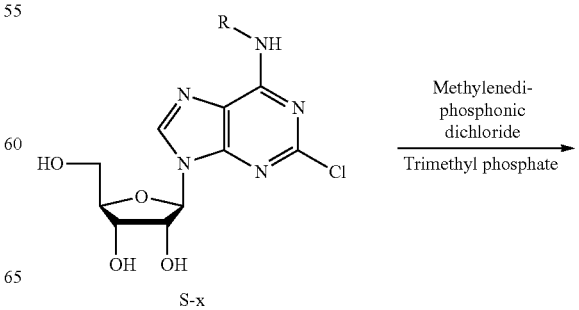

-continued

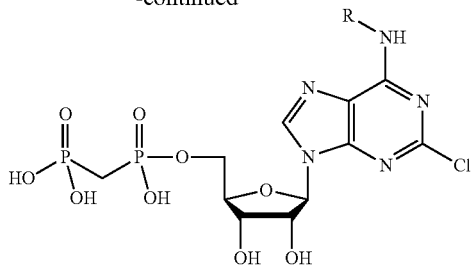

The amine compound RNH$_2$ was obtained either from a commercial source, or prepared according to methods described in the literature.

Preparation of Triethylammonium Hydrogen Carbonate Buffer (TEAC).

A 1 M solution of TEAC was prepared by adding dry ice slowly to a 1 M triethylamine solution in water for several hours until the pH of the solution reached approximately 7.4-7.6 (as measured using a pH meter).

The 2-chloropurine nucleoside derivative S-x (1 mmol, 1 eq.) was dissolved in trimethyl phosphate (10 mL). The solution was cooled with an ice-bath. To the cold solution was added a solution of bis(dichlorophosphoryl)methane (4.0 eq.) in trimethyl phosphate (5 mL). The resulting mixture was stirred at 0° C. for 2-4 h, and the reaction was monitored by thin-layer chromatography (TLC). The reaction was quenched by TEAC solution, and the pH of the reaction solution was adjusted to 7-8. The mixture was extracted with dichloromethane (DCM) and the aqueous phase was isolated and concentrated. The residual material was purified by reversed-phase chromatography with a C18-column, giving the product as colorless solid.

Example 1. Synthesis of Compound 1

DIEA (diisopropylethylamine; 7.5 mmol, 969 mg, 1.5 eq.) was added dropwise to a solution of 2,6-dichloro-9-(2',3', 5'-tri-O-acetyl-β-D-ribofuranosyl)purine (5.0 mmol, 2236 mg, 1.0 eq.) and benzylamine (5.0 mmol, 536 mg, 1.0 eq.) in dioxane (25 mL). The reaction mixture was stirred at room temperature overnight. The solvent was evaporated in vacuo and the residue was dissolved in DCM (100 mL), washed with water (2×30 mL). The crude product was purified by column chromatography. The intermediate was dissolved in 50 mL NH$_3$/CH$_3$OH solution and stirred at 35° C. overnight. The solvent was evaporated in vacuo; and the residual material was purified by column chromatography, giving 2-chloropurine nucleoside derivative S-1 (1818 mg).

S-1 (1.0 mmol, 392 mg, 1.0 eq.) was dissolved in trimethyl phosphate (10 mL), cooled in an ice bath. To the cold solution was added a solution of bis(dichlorophosphoryl) methane (4.0 eq.) in trimethyl phosphate (5 mL). The reaction mixture was stirred at 0° C. for 2-4 h; and the reaction was monitored by TLC. The reaction was quenched by TEAC solution, and the pH of the reaction solution was adjusted to 7-8. The mixture was extracted with DCM and the aqueous phase was isolated, and concentrated. The residual material was purified by reversed-phase column chromatography (C18-column), providing compound 1 as colorless solid (369 mg): $^1$H NMR (500 MHz, CD$_3$OD-d$_4$) δ ppm 2.46 (t, 2H), 4.23-4.74 (m, 7H), 6.01 (d, 1H), 7.19-7.38 (m, 5H), 8.59 (s, 1H); $^{13}$C NMR (125 MHz, CD$_3$Cl-d$_3$) δ ppm 40.12, 43.84, 63.92, 69.87, 74.64, 83.71, 88.50, 115.22, 126.92, 127.47, 128.13, 149.27, 154.08, 154.96, 160.55; $^{31}$P NMR (200 MHz, CD$_3$Cl-d$_3$) δ ppm 12.94, 18.11; m/z (ESI$^+$) 550.1.

Example 2. Synthesis of Compound 6

DIEA (7.5 mmol, 969 mg, 1.5 eq.) was added dropwise to a solution of 2,6-dichloro-9-(2',3',5'-tri-O-acetyl-β-D-ribofuranosyl)purine (5.0 mmol, 2.2 g, 1.0 eq.) and 1-naphthalenemethanamine (5.0 mmol, 786 mg, 1.0 eq.) in dioxane (25 mL). The reaction mixture was stirred at room temperature overnight. The solvent was evaporated in vacuo and the residue was dissolved in DCM (100 mL), washed with water (2×30 mL). Solvent was removed (using a rotary evaporator), and the residual material was purified by column chromatography. The intermediate was dissolved in 50-mL NH$_3$/CH$_3$OH solution and stirred at 35° C. overnight. Solvent was evaporated in vacuo and the residual material was purified by column chromatography, giving S-6 (1.3 g).

S-6 (1.0 mmol, 442 mg, 1.0 eq.) was dissolved in trimethyl phosphate (10 mL), cooled in an ice bath. To the cold solution was added a solution of bis(dichlorophosphoryl) methane (4.0 eq.) in trimethyl phosphate (5 mL). The resulting mixture was stirred at 0° C. for 2-4 h; and the reaction was monitored by TLC. The reaction was quenched by TEAC solution, and the pH of the reaction mixture was adjusted to 7-8. The mixture was extracted with DCM. The aqueous phase was isolated, concentrated; and the residual material was purified by reversed-phase chromatography (C18-column), giving compound 6 as a colorless solid (110 mg): $^1$H NMR (500 MHz, D$_2$O) δ ppm 0.88-0.91 (m, 3H), 1.34-1.43 (m, 4H), 1.67-1.68 (m, 2H), 2.15-2.26 (m, 2H), 4.16-4.22 (m, 2H), 4.25-4.31 (m, 2H), 4.38-4.41 (m, 1H), 4.53-4.57 (m, 1H), 4.74-4.76 (m, H), 6.13-1.15 (m, 1H), 8.70-8.75 (m, 1H); $^{13}$C NMR (125 MHz, D$_2$O) δ ppm 13.20, 21.60, 27.24, 27.55, 63.46, 67.12, 70.15, 74.34, 84.08, 84.14, 87.38, 120.98, 142.83, 150.24, 152.49, 153.22; $^{31}$P NMR (200 MHz, D$_2$O) δ ppm 16.15, 18.97; m/z (ES$^-$) 571.8.

Example 3. Synthesis of Compound 7

DIEA (7.5 mmol, 969 mg, 1.5 eq.) was added dropwise to a solution of 2,6-dichloro-9-(2',3',5'-tri-O-acetyl-β-D-ribofuranosyl)purine (5.0 mmol, 2.2 g, 1.0 eq.) and 2-naphthalenemethanamine (5.0 mmol, 786 mg, 1.0 eq.) in dioxane (25 mL). The reaction was stirred at room temperature overnight. The solvent was evaporated in vacuo and the residue was dissolved in DCM (100 mL), washed with water (2×30 mL). The crude product was purified by column chromatography. The intermediate was dissolved in 50 mL NH$_3$/CH$_3$OH solution and stirred at 35° C. overnight. The solvent was evaporated in vacuo and the residual material was purified by column chromatography, giving 2-chloropurine nucleoside derivative S-7 (1.15 g).

S-7 (1.0 mmol, 442 mg, 1.0 eq.) was dissolved in trimethyl phosphate (10 mL), and the solution was cooled with an ice-bath. To the cold solution was added a solution of bis(dichlorophosphoryl)methane (4.0 eq.) in trimethyl phosphate (5 mL). The reaction mixture was stirred at 0° C. for 2-4 h; and the reaction was monitored by TLC. The reaction was quenched by TEAC solution, and the pH of the reaction mixture was adjusted to 7-8. The mixture was extracted with DCM; and the aqueous phase was isolated and concentrated. The residual material was purified by reversed-phase chromatography (C18-column), providing compound 7 as a colorless solid (105 mg): $^1$H NMR (500 MHz, D$_2$O) δ ppm 2.11 (t, J=19.7 Hz, 2H), 4.10 (s, 2H), 4.29 (s, 1H), 4.42 (s, 1H), 4.55 (s, 1H), 4.88 (s, 2H), 5.79 (s, 1H), 7.36-7.44 (m, 4H), 7.71 (d, J=7.9 Hz, 1H), 7.76 (d, J=7.2 Hz, 1H), 7.87 (d, J=7.8 Hz, 1H), 8.13 (s, 1H); $^{13}$C NMR (125 MHz, D$_2$O) δ ppm 27.57, 42.23, 63.39, 70.05, 74.16, 83.59, 86.92, 117.78, 122.74, 125.48, 125.88, 126.05, 126.26, 128.24, 128.43, 130.48, 132.19, 133.08, 139.02, 148.62, 153.86, 154.44. $^{31}$P NMR (202 MHz, D$_2$O) δ ppm 15.17, 19.58; m/z (ES$^-$) 598.2.

Example 4. Synthesis of Compound 8

The 2-chloropurine nucleoside derivative S-8 (1.0 mmol, 415 mg, 1.0 eq.) was dissolved in trimethyl phosphate (10 mL); and the solution was cooled with an ice-bath. To the cold solution was added a solution of bis(dichlorophosphoryl)methane (4.0 eq.) in trimethyl phosphate (5 mL), while the ice bath was applied. The resulting mixture was stirred at 0° C. for 2-4 h; and the reaction was monitored by TCL. The reaction was quenched by TEAC solution; and the pH of the reaction mixture was adjusted to 7-8. The mixture was extracted with DCM; and the aqueous phase was isolated and concentrated. The residual material was purified (reversed-phase column chromatography, C18-column), to obtain the product as colorless solid (58 mg). $^1$H NMR (500 MHz, D$_2$O) δ ppm 2.12 (t, J=19.7 Hz, 2H), 4.08 (s, 2H), 4.27 (s, 1H), 4.40 (s, 1H), 4.53 (s, 1H), 4.65 (s, 2H), 5.75 (s, 1H), 7.36 (s, 3H), 7.65 (s, 2H), 7.69 (d, J=8.0 Hz, 2H), 8.28 (s, 1H); $^{13}$C NMR (125 MHz, D$_2$O) δ ppm 44.04, 63.41, 70.06, 74.19, 83.73, 86.90, 125.50, 125.60, 126.00, 126.34, 127.38, 128.15, 132.13, 132.71, 135.18, 139.21, 153.96, 154.73; $^{31}$P NMR (202 MHz, D$_2$O) δ ppm 15.86, 19.01; m/z (ES$^-$) 598.4.

Example 5. Synthesis of Compound 9

DIEA (12.5 mmol, 1.6 g, 2.5 eq.) was added dropwise to a solution of 2,6-dichloro-9-(2',3',5'-tri-O-acetyl-β-D-ribofuranosyl)purine (5.0 mmol, 2.2 g, 1.0 eq.) and memantine hydrochloride (5.0 mmol, 1.0 g, 1.0 eq.) in 25-mL dioxane. The reaction mixture was stirred at room temperature overnight. The solvent was evaporated in vacuo and the residue was dissolved in DCM (100 mL), washed with water (2×30 mL), and concentrated. The residual material was purified by column chromatography, to give the intermediate. The intermediate was dissolved in 50 mL NH$_3$/CH$_3$OH solution and the mixture was stirred at 35° C. overnight. The solvent was evaporated in vacuo and the residual material was purified by column chromatography, giving 2-chloropurine nucleoside derivative S-9 (1.1 g).

S-9 (1.0 mmol, 463 mg, 1.0 eq.) was dissolved in trimethyl phosphate (10 mL); and the mixture was cooled with an ice-bath. To the cold mixture was added a solution of bis(dichlorophosphoryl)methane (4 eq.) in trimethyl phosphate (5 mL). The resulting mixture was stirred at 0° C. for 2-4 h; and the reaction was monitored by TLC. After the reaction finished, the reaction was quenched by TEAC solution. The pH of the mixture was adjusted to 7-8. The mixture was extracted with DCM and the aqueous phase was isolated. The aqueous solution was concentrated; and the residue was purified by reversed-phase column chromatography (C18 column), providing compound 9 as a colorless solid (200 mg): $^1$H NMR (500 MHz, D$_2$O) δ ppm 0.76 (s, 6H), 0.98-1.12 (m, 2H), 1.22 (s, 2H), 1.31 (d, J=11.3 Hz, 2H), 1.70 (dd, J=29.4, 11.9 Hz, 4H), 1.90 (s, 2H), 2.11 (t, J=19.9 Hz, 3H), 4.07 (s, 2H), 4.28 (s, 1H), 4.44 (dd, J=6.5, 2.4 Hz, 1H), 4.67-4.63 (m, 1H), 5.91 (d, J=5.7 Hz, 1H), 8.33 (s, 1H); $^{13}$C NMR (125 MHz, D$_2$O) δ ppm 25.96, 26.95, 29.97, 32.08, 39.23, 42.32, 50.32, 55.08, 63.73, 70.04, 74.33, 83.78, 87.45, 116.10, 138.34, 148.62, 153.57, 154.16; $^{31}$P NMR (200 MHz, D$_2$O) δ ppm 18.12; m/z (ES$^-$) 620.2.

Example 6. Synthesis of Compound 10

The 2-chloropurine nucleoside derivative S-10 (1.0 mmol, 451 mg, 1.0 eq.) was dissolved in trimethyl phosphate (10 mL), and the solution was cooled in an ice-bath. To the cold solution was added a solution of bis(dichlorophosphoryl)methane (4 eq.) in trimethyl phosphate (5 mL). The resulting mixture was stirred at 0° C. for 2-4 h, and the reaction was monitored by TLC. The reaction was quenched by TEAC solution; and the pH of the reaction solution was adjusted to 7-8. The mixture was extracted with DCM and the aqueous phase was isolated and concentrated. The residual material was purified by reversed-phase column chromatography (C18-column), giving compound 10 as a colorless solid (60 mg): $^1$H NMR (500 MHz, D$_2$O) δ ppm 2.27 (t, J=19.4 Hz, 2H), 4.17 (s, 2H), 4.35 (s, 1H), 4.46 (s, 1H), 6.02 (s, 1H), 7.27 (s, 4H), 7.54 (s, 2H), 7.97 (s, 2H), 8.33 (s, 1H); $^{13}$C NMR (125 MHz, D$_2$O) δ ppm 16.73, 25.47, 26.48, 27.50, 57.39, 63.69, 70.09, 74.31, 83.84, 87.70, 113.16, 120.00, 122.84, 124.66, 126.42, 138.03, 143.08, 148.86, 152.70, 154.12; $^{31}$P NMR (200 MHz, D$_2$O) δ ppm 17.43, 19.35-19.97; m/z (ES$^-$) 608.0.

Example 7. Synthesis of Compound 11

The 2-Chloropurine nucleoside derivative S-11 (1.0 mmol, 564 mg, 1.0 eq.) was dissolved in trimethyl phosphate (10 mL). The solution was cooled in an ice-bath; and to the cold solution was added a solution of bis(dichlorophosphoryl)methane (4 eq.) in trimethyl phosphate (5 mL). The resulting mixture was stirred at 0° C. for 2-4 h; and the reaction was monitored by TLC. After being quenched by TEAC solution, the pH of the reaction mixture was adjusted to 7-8. This mixture was extracted with DCM and the aqueous phase was isolated and concentrated. The residual material was purified by reversed-phase column chromatography (C18-column), providing compound 11 as a colorless solid (100 mg): $^1$H NMR (500 MHz, D$_2$O) δ ppm 0.77 (d, J=6.5 Hz, 3H), 1.22 (s, 14H), 1.55 (s, 2H), 1.92 (s, 4H), 2.12 (t, J=19.8 Hz, 2H), 2.67 (d, J=38.2 Hz, 4H), 4.03 (s, 2H), 4.19 (s, 1H), 4.40 (s, 1H), 4.60 (s, 1H), 5.20 (d, J=5.6 Hz, 4H), 5.88 (d, J=4.4 Hz, 1H), 8.51 (s, 1H); $^{13}$C NMR (125 MHz, D$_2$O) δ ppm 13.90, 22.48, 24.71, 25.52, 27.10, 29.26, 29.64, 31.41, 36.86, 37.49, 63.89, 70.44, 74.37, 84.15, 86.83, 119.95, 127.82, 129.70, 149.34, 152.45, 152.86, 164.88, 174.66; $^{31}$P NMR (200 MHz, D$_2$O) δ ppm 16.04, 18.65; m/z (ES$^-$) 720.4.

Example 8. Synthesis of Compound 12

DIEA (7.5 mmol, 969 mg, 1.5 eq.) was added dropwise to a solution of 2,6-dichloro-9-(2',3',5'-tri-O-acetyl-β-D-ribofuranosyl)purine (5.0 mmol, 2.23 g, 1.0 eq.) and 2-aminonaphthalene (5.0 mmol, 715 mg, 1.0 eq.) in 25-mL dioxane. The reaction mixture was stirred at room temperature overnight. The solvent was evaporated in vacuo; and the residue was dissolved in DCM (100 mL), washed with water (2×30 mL). The DCM solution was concentrated to dryness; and the residual material was purified by column chromatography, giving an intermediate. The intermediate was dissolved in 50 mL NH$_3$/CH$_3$OH solution and the mixture was stirred at 35° C. overnight. The solvent was evaporated in vacuo and the residual material was purified by column chromatography, providing compound S-12 (670 mg).

S-12 (1.0 mmol, 427 mg, 1.0 eq.) was dissolved in trimethyl phosphate (10 mL), and the solution was cooled in an ice-bath. To the cold solution was added a solution of bis(dichlorophosphoryl)methane (4 eq.) in trimethyl phosphate (5 mL). The resulting mixture was stirred at 0° C. for 2-4 h; and the reaction was monitored by TLC. The reaction was quenched by TEAC solution, and the pH of the quenched reaction mixture was adjusted to 7-8. The mixture was extracted with DCM; and the aqueous phase was isolated and concentrated. The residual material was purified by reversed-phase column chromatography (C18-column), giving compound 12 as a colorless solid (100 mg): $^1$H NMR (D$_2$O, 500 MHz) δ ppm 2.21-2.29 (m, 2H), 4.20-4.22 (m, 2H), 4.40-4.44 (m, 1H), 4.56-4.60 (m, 1H), 4.78-4.80 (m, 1H), 6.09-6.10 (m, 1H), 7.58-7.64 (m, 3H), 7.71-7.73 (m, 1H), 7.97-7.99 (m, 1H) 8.02-8.04 (m, 2H), 8.55 (s, 1H); $^{13}$C NMR (D$_2$O, 125 MHz) δ ppm 26.38, 27.37, 28.36, 63.61, 70.33, 84.01, 86.76, 118.06, 121.57, 122.25, 125.52, 126.23, 126.41, 139.82, 149.74, 153.39, 153.47; $^{31}$P NMR (D$_2$O, 200 MHz) δ ppm 16.14, 18.96; m/z (ES$^-$) 583.9.

Example 9. Synthesis of Compound 15

The 2-Chloropurine nucleoside derivative S-15 (1.0 mmol, 513 mg, 1.0 eq.) was dissolved in trimethyl phosphate (10 mL). The mixture was cooled in an ice-bath, followed by addition of a solution of bis(dichlorophosphoryl)methane (4 eq.) in trimethyl phosphate (5 mL). The resulting mixture was stirred at 0° C. for 2-4 h, and the reaction was monitored by TLC. The reaction was quenched by TEAC solution; and the pH of the reaction mixture was adjusted to 7-8. The mixture was extracted with DCM; and the aqueous phase was isolated and concentrated. The residual material was purified by reversed-phase column chromatography (C18-column), giving compound 15 as a colorless solid (30 mg): $^1$H NMR (500 MHz, D$_2$O) δ ppm 0.70 (t, J=6.3 Hz, 3H), 1.06 (s, 16H), 1.27 (s, 2H), 1.58 (s, 2H), 2.10 (t, J=19.7 Hz, 2H), 4.12 (d, J=32.1 Hz, 4H), 4.27 (s, 1H), 4.46 (s, 1H), 4.66 (s, 1H), 6.00 (d, J=4.7 Hz, 1H), 8.60 (s, 1H); $^{13}$C NMR (125 MHz, D$_2$O) δ ppm 13.73, 22.40, 25.51, 27.55, 28.40, 29.07, 29.36, 31.66, 63.64, 66.70, 70.27, 74.36, 83.95, 87.18, 120.57, 142.65, 150.05, 152.38, 153.21; $^{31}$P NMR (200 MHz, D$_2$O) δ ppm 15.64, 18.89; m/z (ES$^-$) 670.1.

Example 10. Synthesis of Compound 16

The 2-Chloropurine nucleoside derivative S-16 (1.0 mmol, 478 mg, 1.0 eq.) was dissolved in trimethyl phosphate (10 mL); and the mixture was cooled in an ice-bath, followed by addition of a solution of bis(dichlorophosphoryl)methane (4 eq.) in trimethyl phosphate (5 mL). The resulting mixture was stirred at 0° C. for 2-4 h; and the reaction was monitored by TLC. The reaction was quenched by TEAC solution; and the pH of the mixture was adjusted to 7-8. The mixture was extracted with DCM; and the aqueous phase was isolated and concentrated. The residual material was purified by reversed-phase column chromatography (C18-column), providing compound 16 as a colorless solid (250 mg): $^1$H NMR (500 MHz, D$_2$O) δ ppm 1.64 (s, 11H), 1.91 (s, 4H), 2.16 (t, J=19.8 Hz, 2H), 2.29 (s, 2H), 4.14 (dddd, J=6.8, 5.9, 4.1, 1.6 Hz, 3H), 4.30-4.37 (m, 1H), 4.56-4.46 (m, 1H), 6.11 (d, J=5.1 Hz, 1H), 8.72 (s, 1H); $^{13}$C NMR (125 MHz, D$_2$O) δ ppm 16.75, 27.23, 28.38, 33.41, 36.07, 42.03, 51.44, 63.47, 70.17, 74.37, 84.19, 87.49, 115.91, 121.90, 143.36, 149.28, 153.15, 173.66; $^{31}$P NMR (200 MHz, D$_2$O) δ ppm 16.37, 18.85; m/z (ES$^-$) 634.1.

Example 11. Synthesis of Compound 17

DIEA (12.5 mmol, 1.6 g, 2.5 eq.) was added dropwise to a solution of 2,6-dichloro-9-(2',3',5'-tri-O-acetyl-β-D-ribofuranosyl)purine (5.0 mmol, 2.23 g, 1.0 eq.) and 2-adamantanamine hydrochloride (5.0 mmol, 0.94 g, 1.0 eq.) in 25-mL dioxane. The mixture was stirred at room temperature overnight. The solvent was evaporated in vacuo and the residue was dissolved in DCM (100 mL), washed with water (2×30 mL). The organic layer was concentrated; and the residual material was purified by column chromatography, giving an intermediate. This intermediate was dissolved in 50 mL NH$_3$/CH$_3$OH solution and stirred at 35° C. overnight. After evaporation of the solvent, the residual material was purified by column chromatography, providing 2-chloropurine nucleoside derivative S-17 (880 mg). Compound S-17 (1.0 mmol, 435 mg, 1.0 eq.) was dissolved in trimethyl phosphate (10 mL); and the mixture was cooled in an ice-bath. To the cold mixture was added a solution of bis(dichlorophosphoryl)methane (4 eq.) in trimethyl phosphate (5 mL). The resulting mixture was stirred at 0° C. for 2-4 h; and the reaction was monitored by TLC. The reaction was quenched by TEAC solution; and the pH of the mixture was adjusted to 7-8. The mixture was extracted with DCM; and the aqueous phase was isolated and concentrated. The residual material was purified by reversed-phase column chromatography (C18-column), giving compound 17 as a colorless solid (30 mg): $^1$H NMR (500 MHz, D$_2$O) δ ppm 1.60 (d, J=12.7 Hz, 2H), 1.71 (s, 2H), 1.82 (d, J=20.8 Hz, 7H), 1.96 (d, J=19.6 Hz, 4H), 2.14 (t, J=19.8 Hz, 2H), 4.10 (s, 2H), 4.20 (s, 1H), 4.31 (s, 1H), 4.47 (t, J=4.2 Hz, 1H), 5.96 (d, J=5.6 Hz, 1H), 8.41 (s, 1H); $^{13}$C NMR (125 MHz, D$_2$O) δ ppm 16.70, 26.77, 30.81, 31.44, 36.48, 36.86, 57.36, 63.51, 70.23, 74.20, 83.97, 86.73, 139.05, 154.39; $^{31}$P NMR (200 MHz, D$_2$O) δ ppm 15.85, 19.04; m/z (ES$^-$) 592.0.

Example 12. Synthesis of Compound 18

The 2-Chloropurine nucleoside derivative S-18 (1.0 mmol, 512 mg, 1.0 eq.) was dissolved in trimethyl phosphate (10 mL). The mixture was cooled in an ice-bath, followed by addition of a solution of bis(dichlorophosphoryl)methane (4 eq.) in trimethyl phosphate (5 mL). The resulting mixture was stirred at 0° C. for 2-4 h; and the reaction was monitored by thin layer chromatography. The reaction was quenched by TEAC solution; and the pH of the mixture was adjusted to 7-8. The mixture was extracted with DCM; and the aqueous phase was isolated and concentrated. The residual material was purified by reversed-phase column chromatography (C18-column), giving compound 18 as a colorless solid (70 mg): $^1$H NMR (500 MHz, CD$_3$OD-d$_4$) δ ppm 0.93 (t, J=6.8 Hz, 3H), 1.52 (s, 18H), 1.60-1.74 (m, 2H), 2.33 (t, J=19.8 Hz, 2H), 3.43 (t, J=6.6 Hz, 2H), 4.27 (d, J=21.4 Hz, 3H), 4.47-4.61 (m, 1H), 4.71 (t, J=5.3 Hz, 1H), 6.13 (d, J=5.4 Hz, 1H), 8.76 (s, 1H); $^{13}$C NMR (125 MHz, CD$_3$OD-d$_4$) δ ppm 13.01, 22.30, 26.62, 28.98, 29.28, 31.63, 39.56, 63.95, 70.57, 74.91, 84.44, 87.86, 118.78, 142.32, 150.79, 151.78, 151.97, 154.17; $^{31}$P NMR (200 MHz, CD$_3$OD-d$_4$) δ ppm 16.03, 20.25; m/z (ES$^-$), 669.2.

Example 13. Synthesis of Compound 19

DIEA (7.5 mmol, 969 mg, 1.5 eq.) was added dropwise to a solution of 2,6-dichloro-9-(2',3',5'-tri-O-acetyl-β-D-ribofuranosyl)purine (5.0 mmol, 2.23 g, 1.0 eq.) and di-N-dodecylamine (5.0 mmol, 1.8 g, 1.0 eq.) in 25 mL dioxane. The reaction mixture was stirred at room temperature overnight. The solvent was evaporated in vacuo; and the residue was dissolved in DCM (100 mL), washed with water (2×30 mL). The organic layer was concentrated to dryness; and the residual material was purified by column chromatography, giving an intermediate compound. This intermediate was dissolved in 50 mL NH$_3$/CH$_3$OH solution and the mixture was stirred at 35° C. overnight. After removal of solvent in vacuo, the residual material product was purified by column chromatography, giving 2-chloropurine nucleoside derivative S-19 (1.3 g).

S-19 (1.0 mmol, 637 mg, 1.0 eq.) was dissolved in trimethyl phosphate (10 mL). The mixture was cooled in an ice-bath, followed by addition of a solution of bis(dichlorophosphoryl)methane (4 eq.) in trimethyl phosphate (5 mL). The resulting mixture was stirred at 0° C. for 2-4 h; and the reaction was monitored by TLC. The reaction was quenched by TEAC solution; and the pH of the reaction solution was adjusted to 7-8. The mixture was extracted with DCM; and the aqueous phase was isolated and concentrated. The residual material was purified by reversed-phase column chromatography (C18-column), providing compound 19 as a colorless solid (150 mg): $^1$H NMR (500 MHz, CD$_3$OD-d$_4$) δ ppm 0.93 (t, J=6.6 Hz, 6H), 1.32-1.46 (m, 36H), 1.72 (s, 4H), 2.36 (t, J=20.0 Hz, 2H), 3.70 (s, 2H), 4.11-4.32 (m, 5H), 4.47 (s, 1H), 4.66 (t, J=5.2 Hz, 1H), 6.04 (d, J=5.4 Hz, 1H), 8.37 (s, 1H); $^{13}$C NMR (125 MHz, CD$_3$OD-d$_4$) δ ppm 13.08, 22.34, 26.44, 29.08, 29.34, 31.68, 64.24, 70.51, 74.51, 83.84, 87.46, 118.27, 137.84, 151.64, 153.46, 154.25; $^{31}$P NMR (200 MHz, CD$_3$OD-d$_4$) δ ppm 16.20, 19.99; m/z (ES$^-$) 794.6.

Example 14. Synthesis of Compound 20

DIEA (7.5 mmol, 969 mg, 1.5 eq.) was added dropwise to a solution of 2,6-dichloro-9-(2',3',5'-tri-O-acetyl-β-D-ribofuranosyl)purine (5.0 mmol, 2.23 g, 1.0 eq.) and 2-anthracenamine (5.0 mmol, 1.0 g, 1.0 eq.) in 25 mL dioxane. The reaction mixture was stirred at room temperature overnight. The solvent was evaporated in vacuo and the residue was dissolved in DCM (100 mL), washed with water (2×30 mL). The organic layer was concentrated to dryness; and the residual material was purified by column chromatography, giving an intermediate compound. This intermediate was dissolved in 50 mL NH$_3$/CH$_3$OH solution and stirred at 35° C. overnight. The solvent was evaporated in vacuo and the residual material was purified by column chromatography, giving 2-chloropurine nucleoside derivative S-20 (770 mg).

S-20 (1.0 mmol, 477 mg, 1.0 eq.) was dissolved in trimethyl phosphate (10 mL). The mixture was cooled in an ice-bath, followed by addition of a solution of bis(dichlorophosphoryl)methane (4 eq.) in trimethyl phosphate (5 mL). The resulting mixture was stirred at 0° C. for 2-4 h; and the reaction was monitored by TLC. The reaction was quenched by TEAC solution; and the pH of the reaction mixture was adjusted to 7-8. The mixture was extracted with DCM; and the aqueous phase was isolated and concentrated. The residual material was purified by reversed-phase column chromatography (C18-column), providing compound 20 as a colorless solid (80 mg): $^1$H NMR (500 MHz, D$_2$O) δ ppm 2.25 (t, J=19.4 Hz, 2H), 4.28 (d, J=58.1 Hz, 3H), 4.46 (s, 2H), 5.56 (s, 1H), 7.19 (s, 3H), 7.57 (d, J=73.7 Hz, 4H), 7.85 (s, 2H), 8.21 (s, 1H); $^{31}$P NMR (200 MHz, D$_2$O) δ ppm 18.42, 19.15; m/z (ES$^-$) 633.9.

Example 15. Synthesis of Compound 22

DIEA (7.5 mmol, 969 mg, 1.5 eq.) was added dropwise to a solution of 2,6-dichloro-9-(2',3',5'-tri-O-acetyl-β-D-ribofuranosyl)purine (5.0 mmol, 2.23 g, 1.0 eq.) and 1-adamantanamin (5.0 mmol, 756 mg, 1.0 eq.) in 25 mL dioxane. The reaction mixture was stirred at room temperature overnight. The solvent was evaporated in vacuo and the residue was dissolved in DCM (100 mL), washed with water (2×30 mL). After removal of solvent, the residual material was purified by column chromatography, providing an intermediate compound. This intermediate was dissolved in 50 mL NH$_3$/CH$_3$OH solution and the mixture was stirred at 35° C. overnight. The solvent was evaporated in vacuo and the residual material was purified by column chromatography, giving 2-chloropurine nucleoside derivative S-22 (770 mg).

S-22 (1.0 mmol, 435 mg, 1.0 eq.) was dissolved in trimethyl phosphate (10 mL). The mixture was cooled in an ice-bath, followed by addition of a solution of bis(dichlorophosphoryl)methane (4 eq.) in trimethyl phosphate (5 mL). The resulting mixture was stirred at 0° C. for 2-4 h; and the reaction was monitored by TLC. The reaction was quenched by TEAC solution; and the pH of the reaction solution was adjusted to 7-8. The mixture was extracted with DCM; and the aqueous phase was isolated and concentrated. The residual material was purified by reversed phase column chromatography (C18-column), giving compound 22 as a colorless solid (100 mg): $^1$H NMR (500 MHz, D$_2$O) δ ppm 1.64 (s, 6H), 2.06 (d, J=33.5 Hz, 9H), 2.17 (d, J=19.9 Hz, 2H), 4.09 (s, 2H), 4.30 (d, J=0.9 Hz, 1H), 4.45 (ddd, J=5.9, 3.0, 2.0 Hz, 1H), 4.68-4.65 (m, 1H), 5.94 (d, J=5.2 Hz, 1H), 8.38 (s, 1H); $^{13}$C NMR (125 MHz, D$_2$O) δ ppm 26.22, 27.22, 29.28, 35.72, 40.80, 53.50, 63.57, 70.19, 74.20, 83.95, 86.81, 138.60, 148.74, 153.76, 154.43; $^{31}$P NMR (200 MHz, D$_2$O) δ ppm 16.38, 18.81; m/z (ES$^-$) 592.2.

Example 16 Synthesis of Compound 23

The 2-Chloropurine nucleoside derivative S-23 (1.0 mmol, 481 mg, 1.0 eq.) was dissolved in trimethyl phosphate (10 mL), and the mixture was cooled in an ice-bath. To the cold mixture was added a solution of bis(dichlorophosphoryl)methane (4 eq.) in trimethyl phosphate (5 mL). The resulting mixture was stirred at 0° C. for 2-4 h; and the reaction was monitored by TLC. The reaction was quenched by TEAC solution; and the pH of the reaction mixture was adjusted to 7-8. The mixture was extracted with DCM; and the aqueous phase was isolated and concentrated. The residual material was purified by reversed-phase column chromatography (C18-column), giving compound 23 as colorless solid (141 mg): $^1$H NMR (D$_2$O, 500 MHz) δ ppm 0.90-0.97 (m, 9H), 1.18-1.20 (m, 1H), 1.36-1.40 (m, 1H), 1.75-1.80 (m, 1H), 1.90-1.97 (m, 1H), 2.00-2.30 (m, 2H), 2.40-2.45 (m, 1H), 4.20-4.25 (m, 2H), 4.40-4.44 (m, 1H), 4.44-4.57 (m, 1H), 4.72-4.73 (m, 1H), 4.91-5.05 (m, 1H), 6.43-6.45 (m, 1H), 9.02 (m, 1H); $^{13}$C NMR (D$_2$O, 125 MHz) δ 12.74, 18.03, 18.90, 35.91, 44.47, 47.41, 48.45, 63.50, 70.16, 74.34, 83.22, 84.06, 84.13, 87.37, 120.84, 142.72, 150.23, 152.41, 153.24, 153.45 ppm; $^{31}$P NMR (D$_2$O, 200 MHz) δ ppm 16.49, 18.79; m/z (ES$^-$) 638.0.

Example 17. Synthesis of Compound 31

DIEA (7.5 mmol, 969 mg, 1.5 eq.) was added dropwise to a solution of 2,6-dichloro-9-(2',3',5'-tri-O-acetyl-β-D-ribofuranosyl)purine (5.0 mmol, 2.23 g, 1.0 eq.) and 3-azaspiro[4.5]decane (5.0 mmol, 696 mg, 1.0 eq.) in 25 mL dioxane. The reaction mixture was stirred at room temperature overnight. Solvent was evaporated in vacuo and the residue was dissolved in DCM (100 mL), washed with water (2×30 mL). The organic layer was evaporated to dryness, and the residual material was purified by column chromatography, providing an intermediate compound. This intermediate was dissolved in 50 mL $NH_3/CH_3OH$ solution and stirred at 35° C. overnight. Solvent was evaporated in vacuo; and the residual material was purified by column chromatography, giving the corresponding 2-chloropurine nucleoside derivative, S-31 (1.1 g).

S-31 (1.0 mmol, 423 mg, 1.0 eq.) was dissolved in trimethyl phosphate (10 mL); and the mixture was cooled in an ice-bath. To the cold mixture was added a solution of bis(dichlorophosphoryl)methane (4 eq.) in trimethyl phosphate (5 mL). The resulting mixture was stirred at 0° C. for 2-4 h; and the reaction was monitored by TLC. The reaction was quenched by TEAC solution; and the pH of the mixture was adjusted to 7-8. The mixture was extracted with DCM; and the aqueous phase was collected and concentrated. The residual material was purified by reversed-phase column chromatography (C18-column), giving compound 31 as a colorless solid (140 mg): $^1$H NMR (500 MHz, $D_2O$) δ ppm 1.43 (t, J=22.8 Hz, 10H), 1.83 (d, J=52.0 Hz, 2H), 2.15 (t, J=19.7 Hz, 2H), 3.38 (s, 1H), 3.58 (s, 1H), 3.79 (s, 1H), 40.1 (s, 1H), 4.12 (s, 2H), 4.32 (s, 1H), 4.49 (t, J=4.4 Hz, 1H), 4.67-4.70 (m, 1H), 5.97-5.98 (d, J=5.4 Hz, 1H), 8.36-8.37 (d, J=6.8 Hz, 1H); $^{13}$C NMR (125 MHz, $D_2O$) δ ppm 7.67, 8.70, 9.72, 22.92, 27.41, 34.49, 45.49, 47.78, 69.61, 73.58, 74.79, 86.08, 87.43, 118.15, 139.22, 150.08, 153.06, 153.84; $^{31}$P NMR (200 MHz, $D_2O$) δ ppm 15.71, 19.11; m/z (ES$^-$) 580.0.

Example 18. Synthesis of Compound 51

DIEA (7.5 mmol, 969 mg, 1.5 eq.) was added dropwise to a solution of 2,6-dichloro-9-(2',3',5'-tri-O-acetyl-β-D-ribofuranosyl)purine (5.0 mmol, 2.23 g, 1.0 eq.) and nortropine (5.0 mmol, 636 mg, 1.0 eq.) in 25 mL dioxane. The reaction mixture was stirred at room temperature overnight. The solvent was evaporated in vacuo and the residue was dissolved in DCM (100 mL), washed with water (2×30 mL). The residual material was purified by column chromatography, giving an intermediate compound. This intermediate was dissolved in 50 mL $NH_3/CH_3OH$ solution, and the mixture was stirred at 35° C. overnight. After removal of solvent (in vacuo), the residual material was purified by column chromatography, giving a derivative of 2-chloropurine nucleoside S-51 (1.2 g).

Compound S-51 (1.0 mmol, 411 mg, 1.0 eq.) was dissolved in trimethyl phosphate (10 mL). The mixture was cooled in an ice-bath, followed by addition of bis(dichlorophosphoryl)methane (4 eq.) in trimethyl phosphate (5 mL). The resulting mixture was stirred at 0° C. for 2-4 h; and the reaction was monitored by TLC. The reaction was quenched by TEAC solution; and the pH of the reaction solution was adjusted to 7-8. The mixture was extracted then with DCM; and the aqueous phase was isolated and concentrated. The residual material was purified by reversed-phase column chromatography (C18-column), giving compound 51 as a colorless solid (160 mg): $^1$H NMR (500 MHz, $D_2O$) δ ppm 1.78-2.42 (m, 11H), 4.06 (s, 1H), 4.12 (s, 2H), 4.28-4.37 (m, 1H), 4.45-4.55 (m, 1H), 4.82-4.88 (m, 1H), 5.38 (dd, J=3.4, 2.4 Hz, 1H), 5.99 (d, J=5.6 Hz, 1H), 8.40 (s, 1H); $^{13}$C NMR (125 MHz, $D_2O$) δ ppm 26.05, 27.10, 27.68, 37.08, 38.20, 53.79, 54.40, 64.38, 70.20, 74.09, 83.99, 86.71, 117.78, 138.54, 151.12, 154.22; $^{31}$P NMR (200 MHz, $D_2O$) δ ppm 16.90, 18.63; m/z (ES$^-$) 568.0.

Example 19. Synthesis of Compound a-1

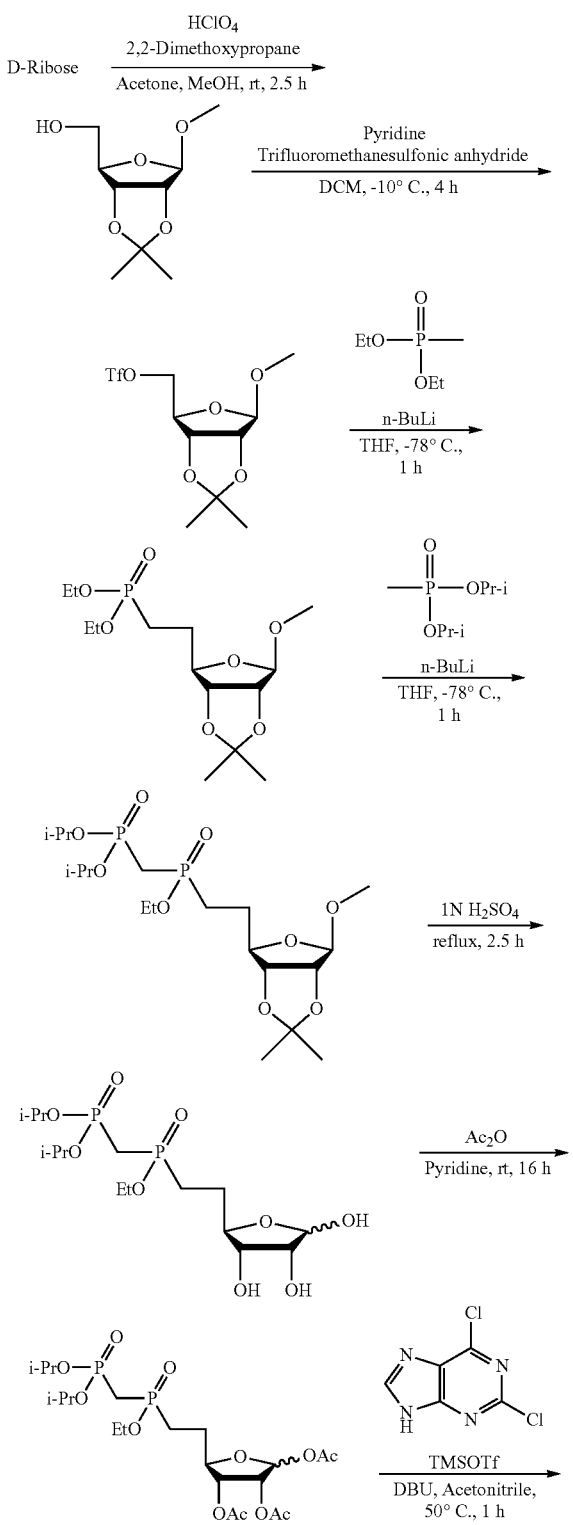

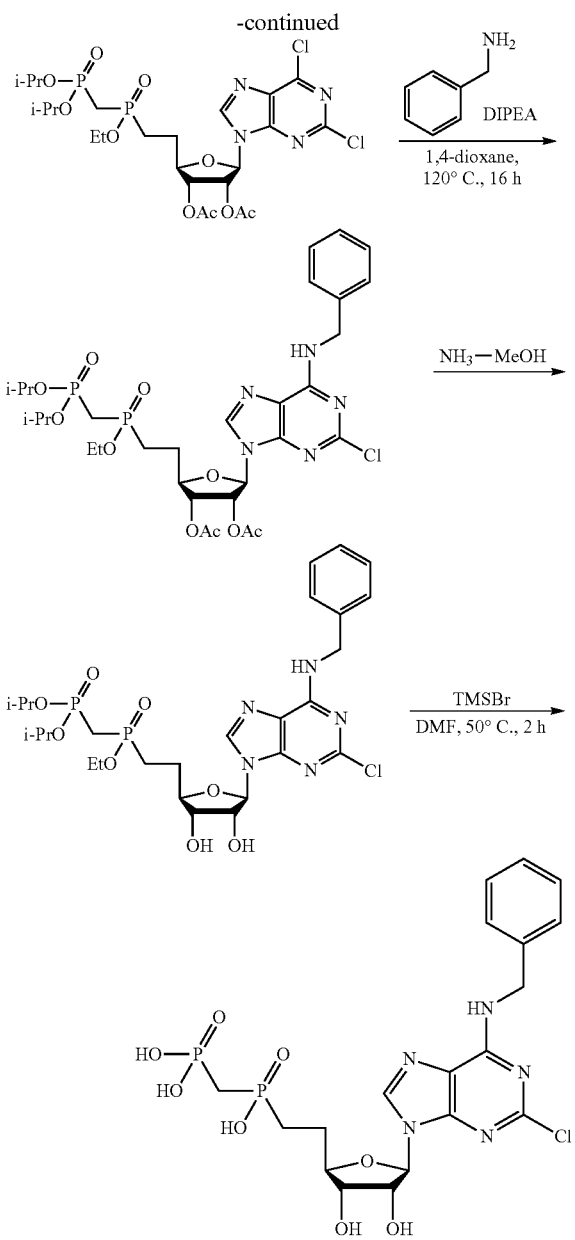

In a 1000 ml round-bottomed flask was added D-Ribose (50 g, 333.05 mmol, 1 eq.), Acetone (400 mL), 2,2-dimethoxypropane (100 mL) and HClO₄ (25 g, 25.00 mL, 70% purity). The mixture was stirred at room temperature for 2.5 h, followed by addition of a solution of MeOH (30 mL) and the mixture was stirred overnight. After the completion of the reaction, it was cooled to −30° C., then a solution of 30% Na₂CO₃ (75 mL) was slowly added so that the temperature did not exceed 10° C. The Acetone (400 mL) was removed to afford the crude product. The precipitate was filtered and washed with ethyl acetate (50 mL). The filtrate was concentrated. The resulting liquid was diluted with ethyl acetate (300 mL). The organic layer was washed with brine (300 mL), dried (Na₂SO₄), filtered and evaporated to dryness. The residue was purified by column chromatography on silica gel eluted with (PE/EA from 100:0 to 70:30) to give [(3aR,4R,6R,6aR)-4-methoxy-2,2-dimethyl-3a,4,6,6a-tetrahydrofuro[3,4-d][1,3]dioxol-6-yl]methanol (43 g, 63.22%). ¹H NMR (500 MHz, CDCl₃) δ ppm 1.29 (s, 3H), 1.44 (d, J=8.3 Hz, 3H), 3.36-3.45 (m, 3H), 3.52-3.72 (m, 2H), 4.39 (t, J=2.8 Hz, 1H), 4.56 (d, J=5.9 Hz, 1H), 4.80 (d, J=5.9 Hz, 1H), 4.94 (s, 1H).

To a solution of [(3aR,4R,6R,6aR)-4-methoxy-2,2-dimethyl-3a,4,6,6a-tetrahydrofuro[3,4-d][1,3]dioxol-6-yl] methanol (20 g, 97.93 mmol, 1 eq.) in DCM (700 mL) was added pyridine (17.82 g, 225.25 mmol, 18.13 mL, 2.3 eq.). The mixture was cooled to about −10° C. Then trifluoromethanesulfonic anhydride (58.03 g, 205.66 mmol, 34.60 mL, 2.1 eq.) was added dropwise into the mixture at about −10° C. The mixture become red and a lot of solid was formed, and kept at −10° C. for about 4 h. The organic layer was washed with water (400 mL), followed by brine (300 mL), dried with Na₂SO₄, filtered, and evaporated to dryness. The residue was purified by column chromatography on silica gel eluted with (PE/EA from 100:0 to 85:15) to give [(3aR,4R,6R,6aR)-4-methoxy-2,2-dimethyl-3a,4,6,6a-tetrahydrofuro[3,4-d][1,3] dioxol-6-yl]methyl trifluoromethanesulfonate (21.6 g, 65.59%) as a brown oil.

To a solution of 1-[ethoxy(methyl)phosphoryl]oxyethane (9.77 g, 64.23 mmol, 1.0 eq.) in THF (60 mL) was cooled to about −78° C. under N₂ protection. Then n-BuLi (2.5 M, 28.26 mL, 1.1 eq.) was added dropwise into the mixture at about −78° C. The mixture was stirred at −78° C. for 25 min. The solution of [(3aR,4R,6R,6aR)-4-methoxy-2,2-dimethyl-3a,4,6,6a-tetrahydrofuro[3,4-d][1,3]dioxol-6-yl]methyl trifluoromethanesulfonate (21.6 g, 64.23 mmol, 1 eq.) in THF (20 mL) was added dropwise into the mixture at about −78° C. The mixture was stirred at −78° C. for 1 h and then quenched by aq. NH₄Cl (60 mL) at about −78° C. H₂O (60 mL) and EtOAc (60 mL) were added into the mixture. The organic layer was separated and the water layer was extracted by EtOAc (60 mL). Combined the organic layer and concentrated and the residue was purified by column chromatography on silica gel eluted with (PE/EA from 100:0 to 0:100) to afford (3aR,4R,6R,6aR)-6-(2-diethoxyphosphorylethyl)-4-methoxy-2,2-dimethyl-3a,4,6,6a-tetrahydrofuro[3,4-d][1,3]dioxole (11 g, 50.62%) as a yellow oil. ¹H NMR (500 MHz, CDCl₃) δ ppm: 1.28-1.34 (m, 9H). 1.47 (s, 3H), 1.72-2.00 (m, 4H), 3.35 (t, J=10.7 Hz, 3H), 4.01-4.19 (m, 5H), 4.53 (d, J=5.9 Hz, 1H), 4.60 (d, J=5.3 Hz, 1H), 4.94 (s, 1H).

A solution of 2-[isopropoxy(methyl)phosphoryl]oxypropane (1.60 g, 8.87 mmol, 2 eq) in THF (6 mL) was cooled to about −78° C. under N₂ protection. n-BuLi (2.5 M, 4.43 mL, 2.5 eq.) was added dropwise into the mixture at about −78° C. The mixture was stirred at −78° C. for 1 h. (3aR,6R,6aR)-6-(2-diethoxyphosphorylethyl)-4-methoxy-2, 2-dimethyl-3a,4,6,6a-tetrahydrofuro[3,4-d][1,3]dioxole (1.5 g, 4.43 mmol, 1 eq) in THF (5 mL) was added into the mixture at about −78° C. The mixture was stirred at −78° C. for 10 minutes and room temperature for 2 h. The mixture was quenched by aq.NH₄Cl at room temperature. The organic layer was separated and the water layer was extracted by EtOAc (50 mL). Combined the organic layer and concentrated to dry, the residue was purified by column chromatography on silica gel eluted with (EA/MeOH from 100:0 to 90:10) to afford (3aR,6R,6aR)-6-[2-[diisopropoxyphosphorylmethyl (ethoxy)phosphoryl]ethyl]-4-methoxy-2, 2-dimethyl-3a,4,6,6a-tetrahydrofuro[3,4-d] [1,3]dioxole (1 g, 47.74%). ¹H NMR (500 MHz, CDCl₃): δ ppm 1.25-1.40 (m, 21H), 1.80-1.82 (m, 2H), 1.94-2.05 (m, 2H), 2.28-2.32 (m, 2H), 3.27-3.29 (m, 3H), 4.05-4.09 (m, 3H), 4.51-4.54 (m, 2H), 4.68-4.70 (m, 2H), 4.86-4.89 (m, 1H).

A solution of (2R,3S,4R,5R)-2-[2-[diisopropoxyphosphorylmethyl(ethoxy) phosphoryl]ethyl]-5-methoxy-tetrahydrofuran-3,4-diol (1.7 g, 3.93 mmol, 1 eq) in 1,4-dioxane (7.6 mL) and aq. sulfuric acid (1 M, 19 mL, 4.83 eq.) was heated to reflux for 2.5 h. After the reaction was cooled to room temperature, it was adjusted to pH 7 by saturated NaHCO₃ (38 mL) and concentrated to dryness. The residue was evaporated with dry THF twice to afford the crude product, which was used in the next step without purification.

To the above solution of (3R,4S,5R)-5-[2-[diisopropoxyphosphorylmethyl(ethoxy) phosphoryl]ethyl]tetrahydrofuran-2,3,4-triol in dry pyridine (25 mL) was added dropwise acetic anhydride (5.0 mL) at 0° C. After the reaction mixture was stirred at room temperature for 16 h, it was evaporated to dryness. The residue was adjusted to pH 2 by aq. HCl (1 M, 15 mL). It was treated with DCM (50 mL) and the organic layer was separated, washed with brine (10 mL), dried, and concentrated. The residue was purified by column chromatography on silica gel eluted with (DCM/MeOH from 100:0 to 90:10) to give [(2R,3R,4R)-4,5-diacetoxy-2-[2-[diisopropoxyphosphoryl methyl(ethoxy)phosphoryl]ethyl]tetrahydrofuran-3-yl] acetate (1.5 g, 70.28%) as a yellow oil. ¹H NMR (500 MHz, MeOD) δ ppm 1.34 (dt, J=12.6, 6.4, 15H), 1.93-2.17 (m, 13H), 2.51-2.83 (m, 2H), 4.13 (dd, J=16.8, 7.2, 2H), 4.23 (d, J=15.6, 1H), 4.66-4.80 (m, 2H), 5.06-5.21 (m, 1H), 5.30 (t, J=15.2, 1H), 5.95-6.45 (m, 1H).

94 To a solution of [(2R,3R,4R)-4,5-diacetoxy-2-[2-[diisopropoxyphosphorylmethyl(ethoxy)phosphoryl]ethyl]tetrahydrofuran-3-yl] acetate (2.5 g, 4.59 mmol, 1 eq.) and 2,6-dichloro-9H-purine (911.2 mg, 4.64 mmol, 1.05 eq.) in ACN (25 mL) was added DBU (768.7 mg, 5.05 mmol, 572.93 μL, 1.1 eq.) and TMSOTf (2.25 g, 10.10 mmol, 1.83 mL, 2.2 eq.) at −10° C. The mixture was stirred at 50° C. for 1 h. The reaction completion was detected by TLC (EA/MeOH=20:1). The mixture was concentrated and purified by column chromatography on silica gel eluted with (EA/MeOH from 100:0 to 95:5) to give [(2R,3R,4R,5R)-4-acetoxy-5-(2,6-dichloropurin-9-yl)-2-[2-[diisopropoxyphosphorylmethyl(ethoxy)phosphoryl]ethyl] tetrahydrofuran-3-yl] acetate (1.5 g, 63.83%). ¹H NMR (500 MHz, CDCl₃): δ ppm 1.21-1.31 (m, 15H), 1.65-2.06 (m, 10H), 2.35-2.46 (m, 2H), 4.07-4.14 (m, 2H), 4.72-5.16 (m, 3H), 5.28-5.77 (m, 1H), 6.08-6.11 (m, 1H), 8.40-9.20 (m, 1H).

To a solution of [(2R,3R,4R,5R)-4-acetoxy-5-(2,6-dichloropurin-9-yl)-2-[2-[diisopropoxy phosphorylmethyl(ethoxy)phosphoryl]ethyl]tetrahydrofuran-3-yl] acetate (250 mg, 371.24 μmol, 1 eq.) and phenylmethanamine (47.74 mg, 445.49 μmol, 1.2 eq.) in 1,4-dioxane (2.5 mL) was added DIPEA (143.94 mg, 1.11 mmol, 193.99 μL, 3 eq.). The mixture was stirred at 120° C. for 16 h. The reaction was complete detected by TLC (EtOAc:MeOH=10:1). The mixture was concentrated and purified by column chromatograph on silica gel eluted with (EA/MeOH from 100:0 to 90:10) to give [(2R,3R,4R,5R)-4-acetoxy-5-[6-(benzylamino)-2-chloro-purin-9-yl]-2-[2-[diisopropoxyphosphorylmethyl(ethoxy)phosphoryl]ethyl] tetrahydrofuran-3-yl] acetate (140 mg, 50.68%) as yellow semi-solid.

A solution of [(2R,3R,4R,5R)-4-acetoxy-5-[6-(benzylamino)-2-chloro-purin-9-yl]-2-[2-[diisopropoxyphosphorylmethyl(ethoxy)phosphoryl]ethyl]tetrahydrofuran-3-yl] acetate (140 mg, 188.14 μmol, 1 eq.) in NH₃-MeOH (7M, 1.5 mL, 57.56 eq.) was stirred at room temperature for 2 h. The mixture was concentrated to remove the solvent to afford the crude product (2R,3R,4S,5R)-2-[6-(benzylamino)-2-chloro-purin-9-yl]-5-[2-[diisopropoxy phosphorylmethyl(ethoxy)phosphoryl]ethyl]tetrahydrofuran-3,4-diol as yellow semi-solid. It was used directly for the next step.

To a solution of (2R,3R,4S,5R)-2-[6-(benzylamino)-2-chloro-purin-9-yl]-5-[2-[diisopropoxyphosphorylmethyl (ethoxy)phosphoryl]ethyl]tetrahydrofuran-3,4-diol (124.18 mg, 188.14 μmol, 1 eq.) in DMF (4 mL) was added bromo(trimethyl)silane (432.05 mg, 2.82 mmol, 15 eq.). The mixture was stirred at 50° C. for 2 h. Then the mixture was quenched by TEAC solution until pH=8 at 0° C. The mixture was concentrated to dry and added H₂O (5 mL) and purified by reversed-phase chromatography (C18-column) (H₂O/ACN from 100:0 to 90:10) to get a-1 (20 mg, 19.40%) as white solid. ¹H NMR (500 MHz, CD₃OD) δ ppm: 1.88-2.13 (m, 6H), 4.04-4.07 (m, 1H), 4.21-4.23 (m, 1H), 4.61-4.63 (m, 1H), 4.77 (s, 2H), 5.94 (d, J=2.5 Hz, 1H), 7.27-7.29 (m, 1H), 7.33-7.36 (m, 2H), 7.41-7.42 (m, 2H), 8.30 (s, 1H); ¹³C NMR (125 MHz, CD₃OD) δ ppm: 27.85, 28.11, 28.89, 31.15, 31.75, 32.07, 32.66, 45.09, 74.36, 75.62, 86.30, 86.43, 69.41, 119.67, 128.33, 128.84, 129.56, 139.98, 141.01, 151.25, 155.72, 156.40; ³¹P NMR (203 MHz, CD₃OD) δ ppm:14.99, 36.71; m/z (ESI⁺): 548.0 (M+H).

Example 20. Synthesis of Compound a-9

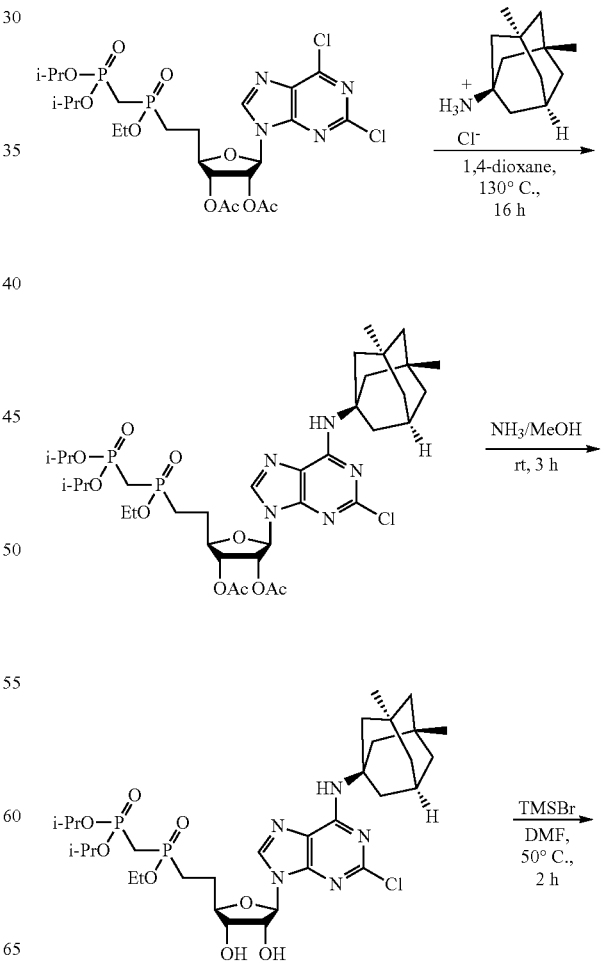

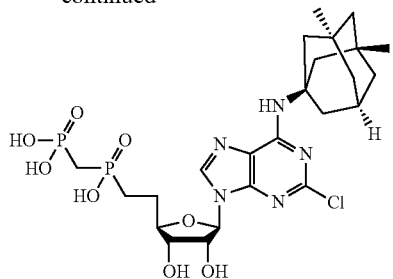

To a solution of [(2R,3R,4R,5R)-4-acetoxy-5-(2,6-dichloropurin-9-yl)-2-[2-[diisopropoxyphosphorylmethyl(ethoxy)phosphoryl]ethyl]tetrahydrofuran-3-yl] acetate (660 mg, 980.08 μmol, 1 eq.) and [(3R,5S)-3,5-dimethyl-1-adamantyl]ammonium; chloride (317.20 mg, 1.47 mmol, 1.5 eq.) in 1,4-dioxane (11 mL) was added DIPEA (380.00 mg, 2.94 mmol, 512.12 μL, 3 eq.). The mixture was stirred at 130° C. for 16 h. The reaction completion was detected by TLC (EtOAc:MeOH=10:1). The mixture was concentrated and purified by column chromatography on silica gel eluted with (EA/MeOH from 100:0 to 92:8) to give [(2R,3R,4R,5R)-4-acetoxy-5-[2-chloro-6-[[(3R,5S)-3,5-dimethyl-1-adamantyl]amino] purin-9-yl]-2-[2-[diisopropoxyphosphorylmethyl(ethoxy)phosphoryl]ethyl]tetrahydrofuran-3-yl]acetate (310 mg, 38.75%) as yellow semi-solid. $^1$H NMR (500 MHz, CD$_3$OD): δ ppm: 0.90 (s, 6H), 1.13-1.50 (m, 20H), 1.79-2.26 (m, 14H), 2.64 (dd, J=31.9, 15.0 Hz, 2H), 4.10 (qd, J=14.4, 7.1 Hz, 2H), 4.64-4.79 (m, 2H), 5.50-5.61 (m, 1H), 5.83-5.94 (m, 1H), 6.09 (d, J=4.9 Hz, 1H), 6.99 (s, 1H), 8.18 (d, J=6.0 Hz, 1H).

A solution of [(2R,3R,4R,5R)-4-acetoxy-5-[2-chloro-6-[[(3R,5S)-3,5-dimethyl-1-adamantyl]amino]purin-9-yl]-2-[2-[diisopropoxyphosphorylmethyl(ethoxy)phosphoryl]ethyl] tetrahydrofuran-3-yl] acetate (310 mg, 379.78 μmol, 1 eq.) in NH$_3$-MeOH (7M, 6 mL, 110.59 eq.) was stirred at room temperature for 3 h. The mixture was concentrated to remove the solvent. EtOAc (35 mL) was added into the residue and washed by brine. The organic layer was dried with Na$_2$SO$_4$ and concentrated to afford the crude product (2R,3R,4S,5R)-2-[2-chloro-6-[[(3R,5S)-3,5-dimethyl-1-adamantyl]amino]purin-9-yl]-5-[2-[diisopropoxyphosphorylmethyl(ethoxy)phosphoryl]ethyl]tetrahydrofuran-3,4-diol (250 mg, 89.91%) as yellow semi-solid. The solid was used directly for the next step.

To a solution of (2R,3R,4S,5R)-2-[2-chloro-6-[[(3R,5S)-3,5-dimethyl-1-adamantyl]amino]purin-9-yl]-5-[2-[diisopropoxyphosphorylmethyl(ethoxy)phosphoryl]ethyl]tetrahydrofuran-3,4-diol (250 mg, 341.44 μmol, 1 eq.) in DMF (8 mL) was added bromo(trimethyl)silane (993.18 mg, 6.49 mmol, 856.19 μL, 19 eq.). The mixture was stirred at 50° C. for 2 h. Then the mixture was quenched by TEAC solution until pH=8 at 0° C. The mixture was concentrated to dry and H$_2$O (8 mL) was added, then compound was purified by reverse-phase chromatography (C18-column) (H$_2$O/ACN from 100:0 to 80:20) to get a-9 (101 mg, 41.02%) as white solid. $^1$H NMR (500 MHz, CD$_3$OD) δ ppm: 0.89 (s, 6H), 1.13-1.23 (m, 2H), 1.35 (d, J=12.3 Hz, 2H), 1.45 (d, J=12.0 Hz, 2H), 1.81 (d, J=11.8 Hz, 2H), 1.85-2.01 (m, 5H), 2.03-2.15 (m, 5H), 2.18 (d, J=2.9 Hz, 1H), 4.02 (dd, J=12.2, 5.3 Hz, 1H), 4.17 (t, J=5.1 Hz, 1H), 4.57 (t, J=5.1 Hz, 1H), 5.89 (d, J=4.8 Hz, 1H), 8.26 (s, 1H); $^{13}$C NMR (125 MHz, CD$_3$OD) δ ppm: 27.68, 27.94, 28.72, 30.75, 31.69, 33.44, 40.72, 43.75, 51.75, 55.91, 74.37, 75.65, 86.15, 86.29, 89.47, 119.70, 140.55, 150.78, 154.97, 155.88; $^{31}$P NMR (203 MHz, CD$_3$OD) δ ppm:14.98, 38.21; m/z (ESI$^+$): 620.1 (M+H).

Example 21. Synthesis of Compound a-19

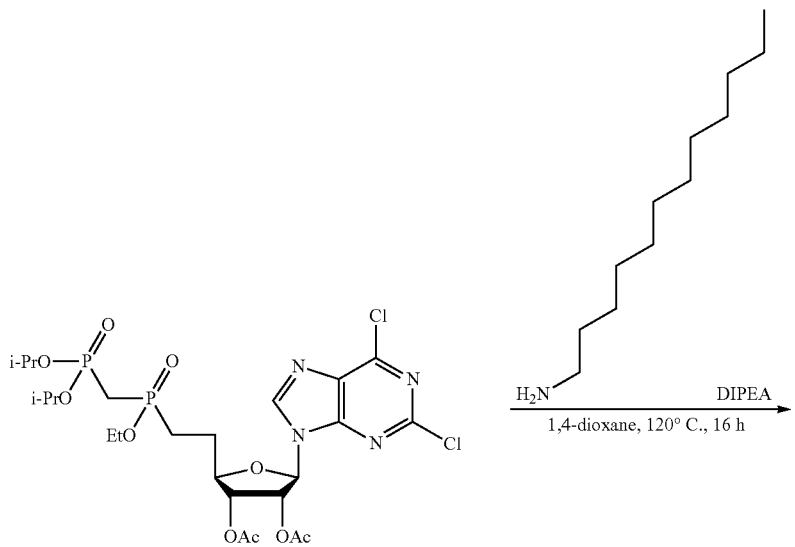

-continued
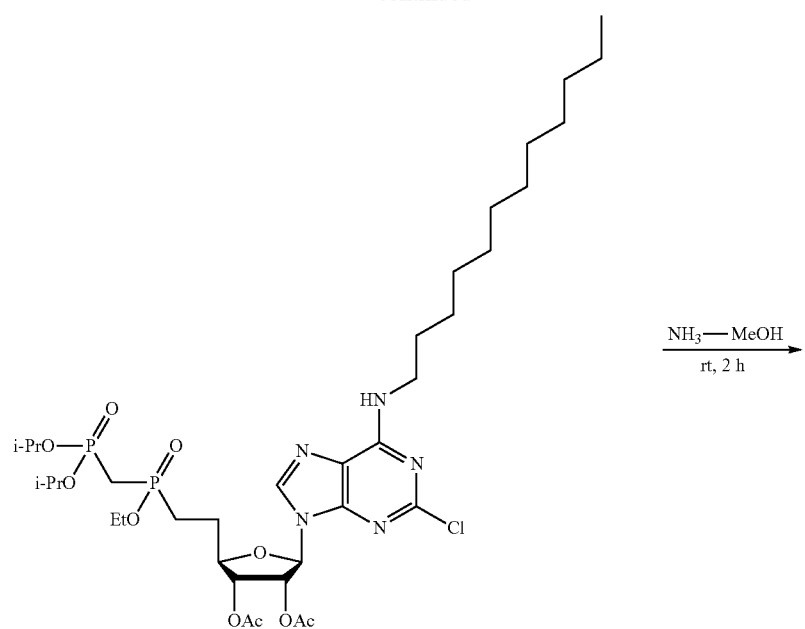
$\xrightarrow{\text{NH}_3-\text{MeOH}}_{\text{rt, 2 h}}$
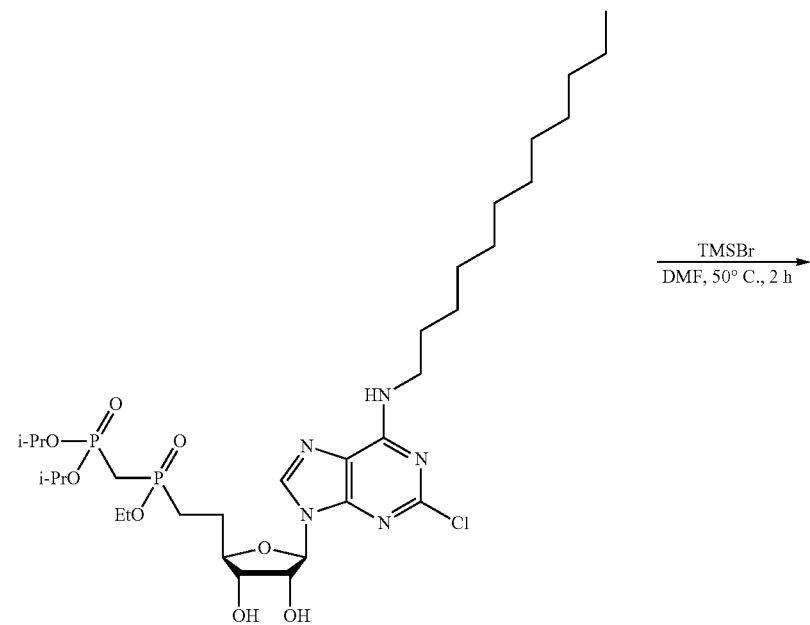
$\xrightarrow{\text{TMSBr}}_{\text{DMF, 50° C., 2 h}}$

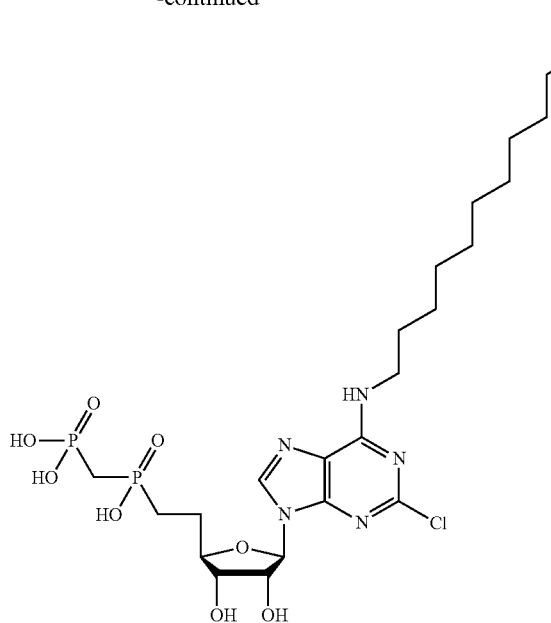

To a solution of [(2R,3R,4R,5R)-4-acetoxy-5-(2,6-dichloropurin-9-yl)-2-[2-[diisopropoxyphosphorylmethyl(ethoxy)phosphoryl]ethyl]tetrahydrofuran-3-yl] acetate (250 mg, 371.24 mol, 1 eq.) and dodecan-1-amine (82.57 mg, 445.49 μmol, 1.2 eq.) in 1,4-dioxane (2.5 mL) was added DIPEA (143.94 mg, 1.11 mmol, 193.99 μL, 3 eq.). The mixture was stirred at 120° C. for 16 h. The reaction completion was detected by TLC (EtOAc:MeOH=10:1). The mixture was concentrated and purified by column chromatography on silica gel eluted with (EA/MeOH from 100:0 to 90:10) to give [(2R,3R,4R,5R)-4-acetoxy-5-[2-chloro-6-(dodecylamino)purin-9-yl]-2-[2-[diisopropoxyphosphorylmethyl(ethoxy)phosphoryl]ethyl] tetrahydrofuran-3-yl] acetate (150 mg, 49.14%) as yellow semi-solid.

To a solution of [(2R,3R,4R,5R)-4-acetoxy-5-[2-chloro-6-(dodecylamino)purin-9-yl]-2-[2-[diisopropoxyphosphorylmethyl(ethoxy)phosphoryl]ethyl]tetrahydrofuran-3-yl] acetate (150 mg, 182.41 μmol, 1 eq.) in NH₃-MeOH (7M, 1.5 mL, 57.56 eq.) was stirred at room temperature for 2 h. The mixture was concentrated to remove the solvent to afford the crude product (2R,3R,4S,5R)-2-[2-chloro-6-(dodecylamino)purin-9-yl]-5-[2-[diisopropoxy phosphorylmethyl(ethoxy)phosphoryl]ethyl]tetrahydrofuran-3,4-diol as yellow semi-solid. It was used directly for the next step.

To a solution of (2R,3R,4S,5R)-2-[2-chloro-6-(dodecylamino)purin-9-yl]-5-[2-[diisopropoxyphosphorylmethyl(ethoxy)phosphoryl]ethyl]tetrahydrofuran-3,4-diol (134.66 mg, 182.41 μmol, 1 eq.) in DMF (4 mL) was added bromo(trimethyl)silane (418.90 mg, 2.74 mmol, 15 eq.). The mixture was stirred at 50° C. for 2 h. Then the mixture was quenched by TEAC solution until pH 8 at 0° C. The mixture was concentrated to dry and H₂O (5 mL) was added, then compound was purified by reverse-phase chromatography (C18-column) (H₂O/ACN from 100:0 to 70:30) to get a-19 (20 mg, 17.51%) as white solid. ¹H NMR (500 MHz, CD₃OD) δ ppm: 0.86-0.089 (m, 3H), 1.26-1.30 (m, 18H), 1.64-1.67 (m, 2H), 1.92-2.17 (m, 6H), 1.81 (d, J=11.8 Hz, 2H), 1.85-2.01 (m, 5H), 2.03-2.15 (m, 5H), 3.51-3.54 (m, 2H), 4.05-4.06 (d, J=5.0, 1H), 4.19 (t, J=5.0 Hz, 1H), 4.59 (t, J=5.0 Hz, 1H), 5.91 (d, J=5.0 Hz, 1H), 8.25 (s, 1H); ¹³C NMR (125 MHz, CD₃OD) δ ppm: 13.13, 22.33, 26.17, 26.45, 28.87, 28.97, 29.04, 29.26, 29.32, 31.64, 40.20, 72.95, 74.25, 84.86, 87.88, 118.09, 139.24, 149.41, 154.44, 155.17; ³¹P NMR (203 MHz, CD₃OD) δ ppm:15.01, 39.35; m/z (ESI⁺): 626.2 (M+H).

Example 22. Synthesis of Compound a-31

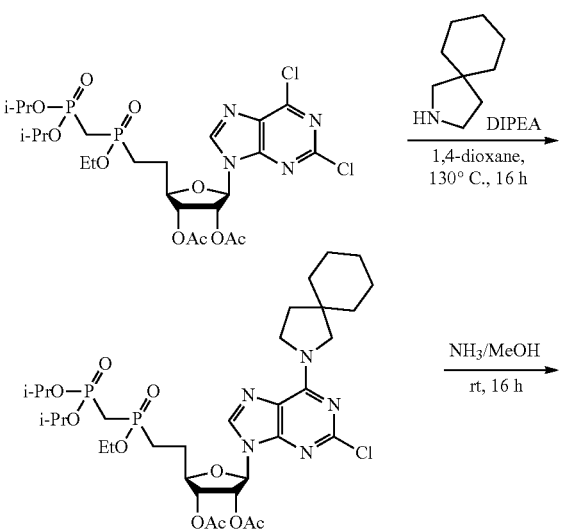

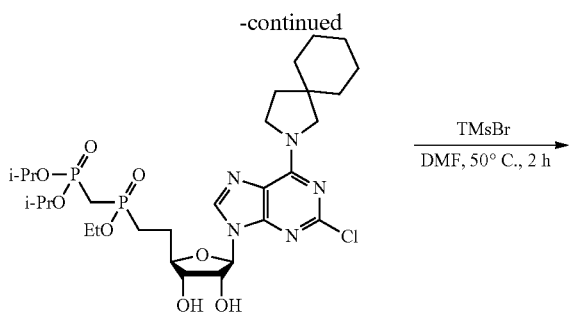

To a solution of [(2R,3R,4R,5R)-4-acetoxy-5-(2,6-dichloropurin-9-yl)-2-[2-[diisopropoxyphosphorylmethyl(ethoxy)phosphoryl]ethyl]tetrahydrofuran-3-yl] acetate (1.5 g, 2.23 mmol, 1 eq) and 2-azaspiro[4.5]decane (465.22 mg, 3.34 mmol, 1.5 eq.) in 1,4-dioxane (15 mL) was added DIPEA (1.01 g, 7.80 mmol, 1.36 mL, 3.0 eq.). The mixture was stirred at 130° C. for 16 h. The reaction completion was detected by TLC (EA/MeOH=20:1). The mixture was concentrated and purified by column chromatography on silica gel eluted with (EA/MeOH from 100:0 to 95:5) to give [(2R,3R,4R,5R)-4-acetoxy-5-[6-(2-azaspiro[4.5]decan-2-yl)-2-chloro-purin-9-yl]-2-[2-[diisopropoxyphosphorylmethyl(ethoxy) phosphoryl] ethyl] tetrahydrofuran-3-yl] acetate (950 mg, 54.95%). 1H NMR (500 MHz, CD3OD): δ ppm 1.26-1.36 (m, 17H), 1.51-1.53 (m, 2H), 1.83-2.17 (m, 12H), 2.62-2.69 (m, 2H), 3.39-3.53 (m, 1H), 3.71-3.73 (m, 1H), 3.93-3.95 (m, 1H), 4.13-4.27 (m, 4H), 4.69-4.71 (m, 2H), 5.58-5.59 (m, 1H), 5.91-5.93 (m, 1H), 6.10-6.12 (m, 1H), 6.15-6.17 (m, 1H).

A solution of [(2R,3R,4R,5R)-4-acetoxy-5-[6-(2-azaspiro[4.5]decan-2-yl)-2-chloro-purin-9-yl]-2-[2-[diisopropoxyphosphorylmethyl(ethoxy)phosphoryl]ethyl]tetrahydrofuran-3-yl] acetate (950 mg, 1.22 mmol, 1 eq.) in NH3-MeOH (7 M, 10 mL, 57.19 eq.) was prepared. The mixture was stirred at room temperature for 16 h. The mixture was concentrated and EtOAc (30 mL) was added. The organic layer was washed with NaCl aqueous, dried (Na2SO4), filtered, and evaporated to dryness to give (2R,3R,4S,5R)-2-[6-(2-azaspiro[4.5]decan-2-yl)-2-chloro-purin-9-yl]-5-[2-[diisopropoxyphosphorylmethyl (ethoxy)phosphoryl]ethyl]tetrahydrofuran-3,4-diol (650 mg, 76.73%). 1H NMR (500 MHz, CD3OD): δ ppm 1.27-1.36 (m, 15H), 1.52-1.54 (m, 10H), 1.84-1.94 (m, 2H), 2.05-2.18 (m, 4H), 2.61-2.68 (m, 2H), 3.52-3.54 (m, 1H), 3.72-3.74 (m, 1H), 3.88-4.03 (m, 2H), 4.12-4.14 (m, 3H), 4.27-4.29 (m, 1H), 4.62-4.73 (m, 3H), 5.89 (s, 1H), 8.14-8.15 (m, 1H).

To a solution of (2R,3R,4S,5R)-2-[6-(2-azaspiro[4.5]decan-2-yl)-2-chloro-purin-9-yl]-5-[2-[diisopropoxyphosphorylmethyl(ethoxy)phosphoryl]ethyl]tetrahydrofuran-3,4-diol (100 mg, 144.48 μmol, 1 eq.) in DMF (4 mL) was added bromo(trimethyl)silane (331.79 mg, 2.17 mmol, 15 eq.) at 0° C. The mixture was stirred at 50° C. for 2 h. Then the mixture was quenched by TEAC solution until pH 8 at 0° C.

The mixture was concentrated to dry and H2O (10 mL) was added, and purified by reverse-phase chromatography (C18-column) (H2O/ACN from 100:0 to 90:10) to get desired product a-31 (20 mg, 20.32%). 1H NMR (CD3OD, 500 MHz): δ ppm 1.51-1.57 (m, 10H), 1.83-2.10 (m, 8H), 3.51-3.53 (m, 1H), 3.71-3.73 (m, 1H), 3.95-3.97 (m, 1H), 4.03-4.04 (m, 1H), 4.16-4.19 (m, 2H), 4.57-4.59 (m, 1H), 5.90-5.91 (d, 1H), 8.19-8.20 (m, 1H); $^{13}$C NMR (CD3OD, 125 MHz): δ ppm 23.02, 25.87, 26.18, 26.40, 27.18, 29.21, 29.80, 30.13, 30.73, 34.89, 40.37, 42.67, 72.94, 74.05, 84.70, 87.93, 118.71, 138.65, 150.96, 153.21, 153.83; 31P NMR (CD3OD, 203 MHz): δ 15.12, 38.73; m/z (ESI+): 580.1 (M+H).

Example 23. Synthesis of Compound c-13

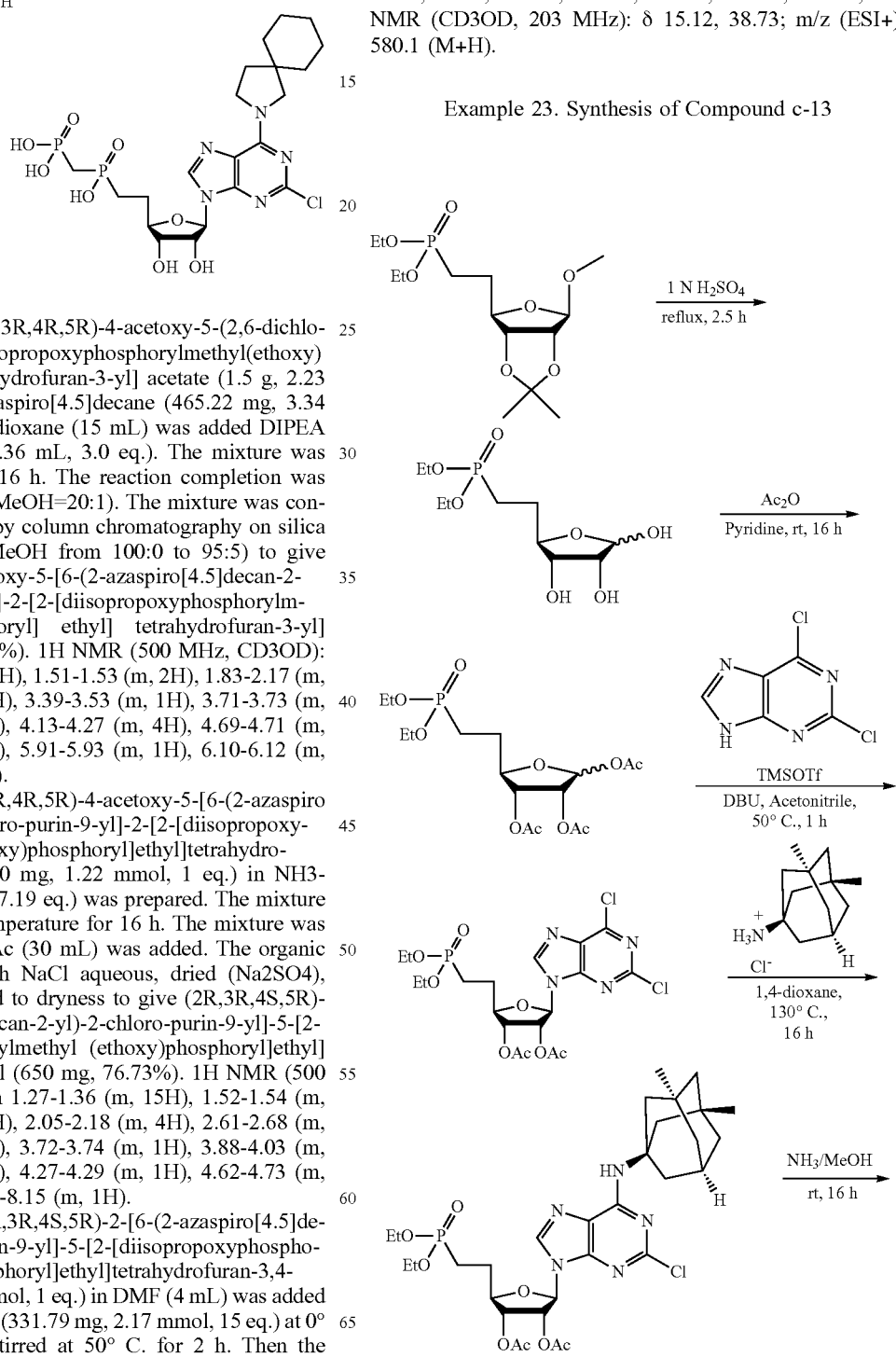

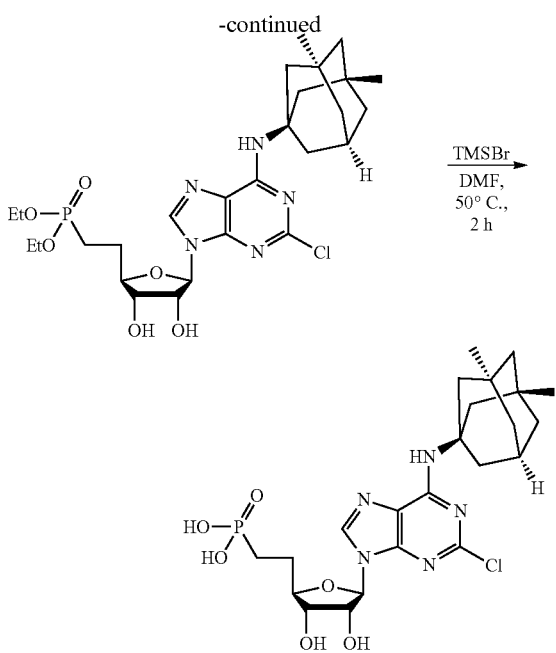

To a mixture of (3aR,4R,6R,6aR)-6-(2-diethoxyphosphorylethyl)-4-methoxy-2,2-dimethyl-3a,4,6,6a-tetrahydrofuro[3,4-d][1,3]dioxole (2.50 g, 7.39 mmol, 1 eq.) in 1,4-dioxane (10 mL) was added 1 N $H_2SO_4$ (1 M, 25 mL, 3.38 eq), and it was heated to reflux for 2.5 h. Then the pH was adjusted to 7 by aq. $NaHCO_3$ (50 mL), and it was concentrated to dryness. To the residue in Pyridine (21 mL) was added $Ac_2O$ (836.84 mg, 8.20 mmol, 4.2 mL), and it was stirred at room temperature for 16 h. The resulting solution was evaporated to dryness. The residue was purified by column chromatography on silica gel eluted with (DCM/MeOH from 100:0 to 95:05) to give [(2R,3R,4R)-4,5-diacetoxy-2-(2-diethoxyphosphorylethyl) tetrahydrofuran-3-yl] acetate (1.9 g, 62.67%). $^1$H NMR (500 MHz, CDCl3): δ ppm 1.36-1.54 (m, 6H), 1.81-2.30 (m, 13H), 1.94-2.05 (m, 2H), 4.13-4.31 (m, 5H), 4.90-5.23 (m, 2H), 6.16-6.41 (m, 1H).

To a solution of [(2R,3R,4R)-4,5-diacetoxy-2-(2-diethoxyphosphorylethyl) tetrahydrofuran-3-yl] acetate (1.9 g, 4.63 mmol, 1 eq) in ACN (19 mL) was added DBU (775.39 mg, 5.09 mmol, 760.18 μL, 1.1 eq) and TMSOTf (2.26 g, 10.19 mmol, 1.84 mL, 2.2 eq) at −10° C. The mixture was stirred at 50° C. for 1 h. The mixture was concentrated and purified by column chromatography on silica gel eluted with (EA/MeOH from 100:0 to 95:5) to give [(2R,3R,4R,5R)-4-acetoxy-5-(2,6-dichloropurin-9-yl)-2-(2-diethoxyphosphoryl ethyl) tetrahydrofuran-3-yl] acetate (1.3 g, 52.06%). $^1$H NMR (500 MHz, CDCl$_3$): δ ppm 1.24-1.34 (m, 6H), 2.01-2.14 (m, 10H), 4.09-4.12 (m, 5H), 5.56-5.58 (m, 1H), 5.88-5.90 (m, 1H), 6.24-6.25 (d, 1H), 8.68 (s, 1H).

To a solution of [(2R,3R,4R,5R)-4-acetoxy-5-(2,6-dichloropurin-9-yl)-2-(2-diethoxyphosphorylethyl)tetrahydrofuran-3-yl] acetate (1.3 g, 2.41 mmol, 1 eq.) and [(3R,5S)-3,5-dimethyl-1-adamantyl]ammonium; chloride (624.12 mg, 2.89 mmol, 1.2 eq.) in 1,4-dioxane (13 mL) was added DIPEA (934.61 mg, 7.23 mmol, 1.26 mL, 3 eq.). The mixture was stirred at 130° C. for 16 h. The reaction completion was detected by TLC. The mixture was concentrated and purified by column chromatography on silica gel eluted with (EA/MeOH from 100:0 to 90:10) to give [(2R,3R,4R,5R)-4-acetoxy-5-[2-chloro-6-[[(3R,5S)-3,5-dimethyl-1-adamantyl] amino]purin-9-yl]-2-(2-diethoxyphosphorylethyl)tetrahydrofuran-3-yl] acetate (700 mg, 42.57%). $^1$H NMR (500 MHz, CD$_3$OD): δ ppm 0.84-0.91 (m, 6H), 1.20-1.32 (m, 9H), 1.36-1.52 (m, 4H), 1.82-2.01 (m, 6H), 2.07-2.14 (m, 10H), 4.08-4.11 (m, 5H), 5.57-5.60 (m, 1H), 5.87-5.89 (m, 1H), 6.09-6.10 (m, 1H), 8.16 (m, 1H).

To a solution of [(2R,3R,4R,5R)-4-acetoxy-5-[2-chloro-6-[[(3R,5S)-3,5-dimethyl-1-adamantyl]amino]purin-9-yl]-2-(2-diethoxyphosphorylethyl)tetrahydrofuran-3-yl]acetate (700 mg, 1.03 mmol, 1 eq) was added $NH_3$-MeOH (7 M, 7 mL, 47.75 eq.). The mixture was stirred at room temperature for 16 h. The mixture was concentrated and EtOAc (30 mL) was added, and the organic layer was washed with aq. NaCl, dried ($Na_2SO_4$), filtered, and evaporated to give (2R,3R,4S,5R)-2-[2-chloro-6-[[(3R,5S)-3,5-dimethyl-1-adamantyl] amino]purin-9-yl]-5-(2-diethoxyphosphorylethyl) tetrahydrofuran-3,4-diol (400 mg, 65.18%). $^1$H NMR (500 MHz, CD$_3$OD): δ ppm 0.90-0.92 (m, 6H), 1.20-1.26 (m, 2H), 1.29-1.32 (m, 6H), 1.36-1.39 (m, 2H), 1.46-1.48 (m, 2H), 1.82-1.84 (m, 2H), 1.91-1.93 (m, 3H), 1.96-2.05 (m, 3H), 2.10-2.12 (m, 2H), 2.20-2.21 (m, 1H), 4.03-4.11 (m, 5H), 4.27-4.29 (m, 1H), 4.69-4.71 (m, 1H), 5.86-5.87 (m, 1H), 8.15 (s, 1H).

To a solution of (2R,3R,4S,5R)-2-[2-chloro-6-[[(3R,5S)-3,5-dimethyl-1-adamantyl] amino] purin-9-yl]-5-(2-diethoxyphosphorylethyl)tetrahydrofuran-3,4-diol (100 mg, 167.20 μmol, 1 eq) in DMF (4 mL) was added bromo (trimethyl)silane (383.97 mg, 2.51 mmol, 331.01 μL, 15 eq) at 0° C. The mixture was stirred at 50° C. for 2 h. Then the mixture was quenched by TEAC solution until pH 8 at 0° C. The mixture was concentrated and $H_2O$ (10 mL) was added, then compound was purified by reverse-phase chromatography (C18-column) ($H_2O$/ACN from 100:0 to 70:30) to get c-13 (40 mg, 37.20%). $^1$H NMR (CD$_3$OD, 500 MHz): δ ppm 1.19-1.26 (m, 2H), 1.36-1.38 (m, 2H), 1.45-1.48 (m, 2H), 1.63-1.74 (m, 2H), 1.82-1.84 (m, 2H), 1.90-1.95 (m, 2H), 1.98-2.10 (m, 4H), 2.19-2.21 (m, 1H), 4.02-4.03 (m, 1H), 4.15-4.17 (m, 1H), 4.55-4.56 (m, 1H), 5.90-5.91 (d, 1H), 8.22 (s, 1H). $^{13}$C NMR (CD3OD, 125 MHz): δ ppm 25.41, 26.49, 29.21, 30.75, 31.70, 33.45, 40.71, 43.76, 51.76, 55.91, 74.60, 75.76, 85.99, 86.13, 89.71, 119.74, 140.42, 150.68, 154.98, 155.88; $^{31}$P NMR (CD3OD, 203 MHz): δ ppm 24.12; m/z (ESI$^-$): 540.2 (M–H).

Biological Assays

1. CD73 Inhibitor Screening Assay

To evaluate the inhibitory effect of the compounds on CD73, Malachite Green Phosphate Detection Kit (R&D, Cat #DY996) was used. Briefly, compounds were dissolved and diluted to the desired concentration using phosphate-free buffer (Tris-HCl, pH 7.3). 25 μL of the compound solution was added to an equal volume of CD73 protein solution (2× concentration, 0.5 μg/mL, Novoprotein, Cat #C446), followed by a 5-minute incubation at room temperature. 10 μL of Malachite Green Reagent A was added to each well, mixed thoroughly and incubated for 10 minutes at room temperature. 10 μL of Malachite Green Reagent B was then added to each well, mixed thoroughly and incubated for 20 minutes at room temperature. Finally, the optical density of each well was determined using a microplate reader set to 620 nm.

The inhibitory activity of selected compounds is given in Table 2. In addition, compounds such as a-1, a-9, and a-31 showed inhibitory activity in the assay.

TABLE 2

Compound inhibitory activity in CD73 enzyme assay.

| Compound No. | Potency[1] |
|---|---|
| 1 | +++ |
| 2 | ++ |
| 6 | +++ |
| 7 | +++ |
| 8 | ++ |
| 9 | +++ |
| 10 | ++ |
| 11 | ++ |
| 12 | ++ |
| 15 | +++ |
| 16 | ++ |
| 17 | +++ |
| 18 | ++ |
| 19 | + |
| 20 | ++ |
| 22 | +++ |
| 23 | ++ |
| 31 | +++ |
| 51 | +++ |

[1] "+" denotes $IC_{50}$ >100 nM;
"++" denotes $IC_{50}$ of 10-100 nM;
"+++" denotes $IC_{50}$ <10 nM.

2. Cell-Based Assay of CD73 Activity

Prepare 5× compound solution by dissolving and diluting the compounds to desired concentrations using serum free RMPI-1640 medium containing 1 µM AMP. A375 cells are collected and washed twice with PBS, then suspended in serum-free RMPI-1640 medium to a density of $1.125 \times 10^5$/mL. Aliquot 80 µL of the cell suspension to a 96-well plate, then add 20 µL of the 5× compound solution, mix gently and culture for 16 hrs at 37° C., 5% $CO_2$. After incubation, transfer 50 µL of supernatant from each well to a new 96-well plate. Then sequentially add 2 µL of 2.5 µM ATP and 50 µL of Celltiter Glo reagent to each well. Measure luminescence using PheraStar (BMG).

3. Pharmacokinetic Evaluation of the Compounds

Following a single i.v. (1 mg/kg) or i.g. (3 mg/kg) administration of the compounds to fasted male SD rats, blood samples were collected at 0.08, 0.25, 0.5, 1, 2, 4, 6, 8 and 24 h after administration. Plasma was separated by centrifugation (8000 rpm) and frozen (−20° C.) until the sample was analyzed. Concentrations of the compounds in rat plasma were determined by HPLC-MS/MS. Plasma was dispensed into appropriate tubes containing internal standard and methanol or acetonitrile. The tubes were mixed vigorously for 3 minutes to achieve deproteinization and then centrifuged at 8000 rpm for 5 minutes. The supernatant was transferred to an autosampler vial, and was injected into the chromatographic system. Pharmacokinetic Parameters including $AUC_{0-t}$, C max, t max $t_{1/2}$, MRT, Cl and Vd were calculated using WinNonlin 6.3 software. Absolute bioavailability was calculated as follows: F=[AUC(i.g.)*dose(i.v.)]/[AUC(i.v.)*dose(i.g.)]*100%.

Although this invention is described in detail with reference to embodiments thereof, these embodiments are offered to illustrate but not to limit the invention. It is possible to make other embodiments that employ the principles of the invention and that fall within its spirit and scope as defined by the claims appended hereto.

What is claimed is:

1. A compound of Formula I, or a pharmaceutically acceptable ester or salt thereof:

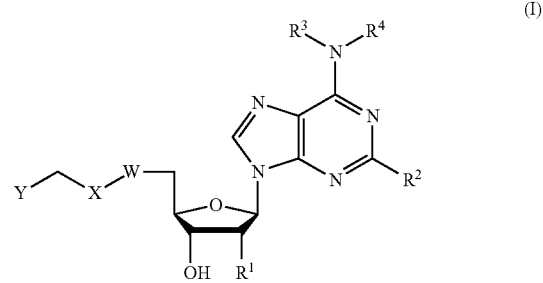

where:

W is oxygen, sulfur, nitrogen, or a methylene group;

X is a moiety selected from phosphonyl (—P(=O)(OR)—), sulfonyl (—S(=O)$_2$—), and carbonyl (—C(=O)—), where R is a hydrogen, an ester-forming group, or a protecting group; or X and W together form —(CR$^7$R$^8$)$_n$—, where n is an integer from 0 to 3, and R$^7$ and R$^8$ are independently selected from a hydrogen, a halogen, a hydroxyl group, and a lower alkyl group having 1 to 4 carbon atoms;

Y is selected from phosphonate (—PO$_3$R$_2$), sulfonate (—SO$_3$R), and carboxylate (—CO$_2$R), where R is a hydrogen, an ester-forming group, or a protecting group;

R$^1$ is a hydroxyl group or a hydrogen;

R$^2$ is a chlorine or a hydrogen; and

R$^3$ and R$^4$ are independently selected from a hydrogen, an alkyl group, an alkenyl group and an alkynyl group, where at least one of R$^3$ and R$^4$ has 1 to 30 carbon atoms, wherein at least one of R$^3$ and R$^4$ has 11 to 30 carbon atoms when W is O or S; or R$^3$ and R$^4$ are independently selected from a hydrogen and a ring system which is a monocycle, bicycle, tricycle, spiral-ring, fused-ring, or bridged-ring containing carbocyclic or heterocyclic ring system, the carbocyclic ring system being aromatic or non-aromatic, provided that R$^3$ and R$^4$ are not both hydrogen, and provided that the ring system is not a monocycle when W is O or S; or R$^3$, R$^4$, and the nitrogen atom to which they are attached form a heterocyclic system which is independently selected from a monocycle, a bicycle, a tricycle, a spiral-ring, a fused-ring, and a bridged-ring system.

2. The compound of claim 1, wherein R$^3$ is a hydrogen or a lower alkyl; and

R$^4$ is —C(=O)R$^5$, —C(=O)NHR$^5$ or —C(=O)OR$^5$, where R$^5$ is a C$_{1-30}$ alkyl group, a C$_{2-30}$ alkenyl group or a C$_{2-30}$ alkynyl group, provided that R$^5$ is a C$_{11-30}$ alkyl, C$_{11-30}$ alkenyl or C$_{11-30}$ alkynyl group when W is O or S.

3. The compound of claim 1, wherein R$^3$ is a hydrogen or a lower alkyl; and R$^4$ is —C(=O)R$^5$, —C(=O)NHR$^5$ or —C(=O)OR$^5$, where R$^5$ is a ring system having a monocycle, a bicycle, a tricycle, a spiral-ring, a fused-ring or a bridged-ring containing a carbocyclic or a heterocyclic ring system, the carbocyclic ring system being aromatic or non-aromatic, and the heterocyclic ring system being substituted or unsubstituted, provided that R$^5$ is not a monocycle ring system when W is O or S.

4. The compound of claim 1, wherein the compound is a compound of Formula IVa, Formula IVb, Formula IVc, Formula Va, Formula VIa, Formula VIIa, or Formula VIIIa, or a pharmaceutically acceptable salt or ester thereof:

(IVa)
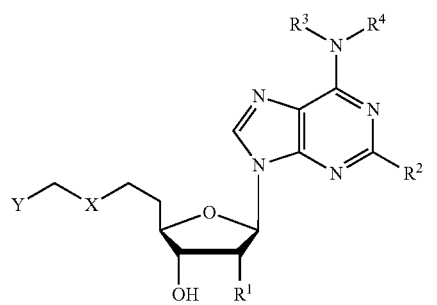

(IVb)
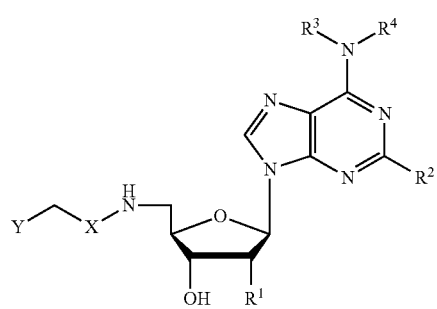

(IVc)
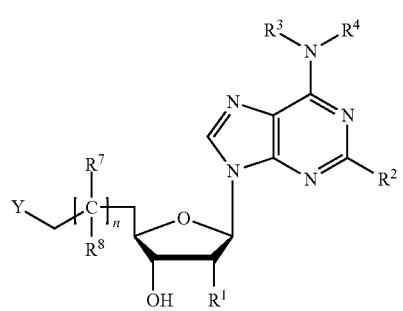

(Va)
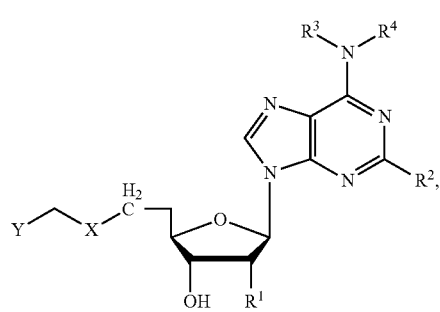

(VIa)
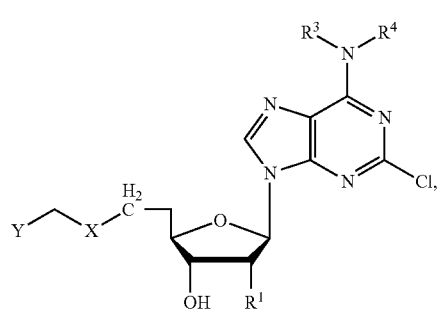

(VIIa)
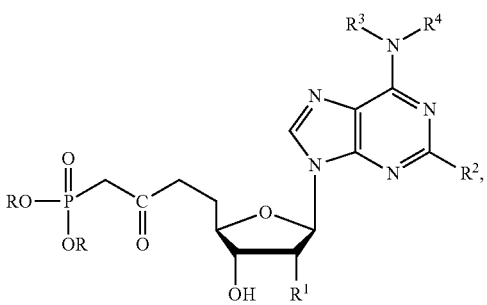

(VIIIa)
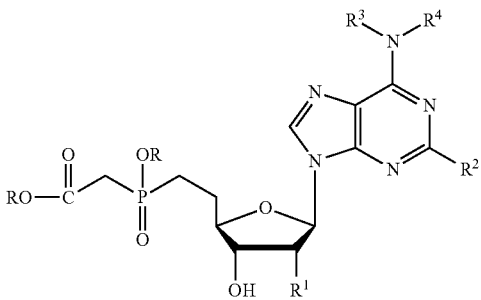

where:
in formula IVc, n is an integer from 0 to 3, and $R^7$ and $R^8$ are independently selected from a hydrogen, a halogen, a hydroxyl group and a lower alkyl group which has from 1 to 4 carbon atoms; and
in formula VIIa and formula VIIIa, R is a hydrogen, an ester-forming group, or a protecting group.

5. The compound of claim 1, wherein the compound is a compound of Formula IXa, or a pharmaceutically acceptable salt or ester thereof:

(IXa)
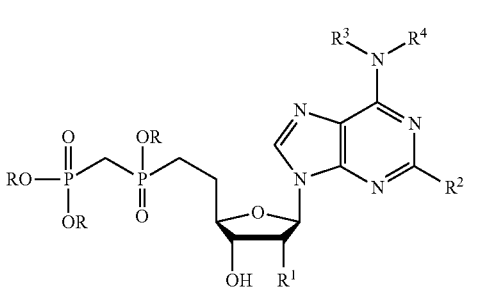

where:
R is a hydrogen, an ester-forming group, or a protecting group;
$R^1$ is a hydroxyl group or a hydrogen;
$R^2$ is a hydrogen or a chlorine; and
$R^3$ is a hydrogen or a lower alkyl, and $R^4$ is an alkyl, an alkenyl, or an alkynyl group having 1 to 30 carbon atoms; or
$R^3$ is a hydrogen or a lower alkyl, and $R^4$ is a substituent group containing a monocyclic, bicyclic, tricyclic, or multi-cyclic ring system, where the ring system is fused, spiral, bridged, or parallel, and the ring system is carbocyclic, aliphatic, aromatic, heterocyclic, or a combination thereof; or R³ is a hydrogen or a lower alkyl, and R⁴ is —C(=O)R⁵, —C(=O)NHR⁵ or —C(=O)OR⁵, where R⁵ is an alkyl group, an alkenyl group or an alkynyl group having 1 to 30 carbon atoms; or R³ is a hydrogen or a lower alkyl, and R⁴ is —C(=O)R⁵ or —C(=O)OR⁵, where R⁵ is a substituent group containing a bicycle, tricycle, spiral-ring, fused-ring or bridged-ring containing a carbocyclic or a heterocyclic ring system, the carbocyclic ring system being aromatic or non-aromatic, the heterocyclic ring system being substituted or unsubstituted), where the ring is carbocyclic, aliphatic, aromatic, heterocyclic, or a combination thereof; or R³ is a hydrogen or a lower alkyl, and R⁴ is an unsubstituted or substituted 1-adamantyl, α-naphthylmethyl, or β-naphthylmethyl; or R³, R⁴, and the nitrogen atom to which they are attached form a heterocyclic system independently selected from a monocycle, a bicycle, a tricycle, a spiral-ring, a fused-ring, and a bridged-ring.

6. The compound of claim 5 wherein R³ is a hydrogen or a lower alkyl; and R⁴ is a group containing an adamantyl moiety.

7. The compound of claim 6, wherein R⁴ is substituted or non-substituted 1-adamantyl; substituted or non-substituted 2-adamantyl; substituted or non-substituted 1-adamantylmethyl; substituted or non-substituted 1-adamantylethyl; substituted or non-substituted 1-adamantylpropyl; or substituted or non-substituted 1-adamantylbutyl.

8. The compound of claim 5, wherein R³ is a hydrogen or a lower alkyl; and R⁴ is a group containing a naphthyl moiety.

9. The compound of claim 8, wherein R⁴ is substituted or non-substituted α-naphthyl; substituted or non-substituted β-naphthyl; substituted or non-substituted α-naphthylmethyl; substituted or non-substituted β-naphthylmethyl; substituted or non-substituted naphthylethyl; substituted or non-substituted naphthylpropyl; or substituted or non-substituted naphthylbutyl.

10. The compound of claim 1, wherein the C, H, O, and N atoms in the compound are each independently selected from atoms of natural abundance and isotope-enriched atoms, wherein the isotope-enriched atoms are selected from ¹²C, ¹³C, and ¹⁴C for carbon; selected from ¹H, ²H, and ³H for hydrogen; selected from ¹⁶O, ¹⁷O, and ¹⁸O for oxygen; and selected from ¹⁴N and ¹⁵N for nitrogen.

11. A pharmaceutical composition comprising the compound or pharmaceutically acceptable salt or ester thereof of claim 1 and a pharmaceutically acceptable carrier.

12. A method of treating or preventing a CD73-associated disease, disorder or condition in a subject in need thereof, comprising administering a therapeutically effective amount of the compound of claim 1 to the subject, such that the CD73-associated disease, disorder or condition is treated or prevented in the subject, wherein the CD73-associated disease, disorder or condition is CD73-mediated immunosuppression; cancer; or an immune-related disease, disorder or condition selected from the group consisting of rheumatoid arthritis, kidney failure, lupus, asthma, psoriasis, colitis, pancreatitis, allergies, fibrosis, anemia fibromyalgia, Alzheimer's disease, congestive heart failure, stroke, aortic valve stenosis, arteriosclerosis, osteoporosis, Parkinson's disease, infections, Crohn's disease, ulcerative colitis, allergic contact dermatitis, eczema, systemic sclerosis and multiple sclerosis.

13. The method of claim 12, wherein said compound is administered in an amount effective to reverse, slow or stop the progression of CD73-mediated immunosuppression in the subject.

14. The method of claim 12, wherein the CD73-associated disease, disorder or condition is cancer.

15. The method of claim 14, wherein said cancer is a cancer of the prostate, colon, rectum, pancreas, cervix, stomach, endometrium, brain, liver, bladder, ovary, testis, head, neck, skin, mesothelial lining, white blood cell, esophagus, breast, muscle, connective tissue, lung, adrenal gland, thyroid, kidney, or bone.

16. The method of claim 12, wherein the CD73-associated disease, disorder or condition is an immune-related disease, disorder or condition selected from the group consisting of rheumatoid arthritis, kidney failure, lupus, asthma, psoriasis, colitis, pancreatitis, allergies, fibrosis, anemia fibromyalgia, Alzheimer's disease, congestive heart failure, stroke, aortic valve stenosis, arteriosclerosis, osteoporosis, Parkinson's disease, infections, Crohn's disease, ulcerative colitis, allergic contact dermatitis, eczema, systemic sclerosis and multiple sclerosis.

17. A method of treating cancer in a subject, comprising administering to said subject an effective amount of the compound of claim 1 and an immune checkpoint inhibitor, such that cancer is treated in the subject.

18. The method of claim 17, wherein said administering is prior to, concurrent with, or subsequent to, radiation treatment.

19. The method of claim 17, wherein said compound and said immune checkpoint inhibitor are administered in combination or sequentially.

20. The method of claim 17, wherein said immune checkpoint inhibitor is selected from the group consisting of ipulimumab, nivolumab and lambrolizumab.

21. A compound which is:

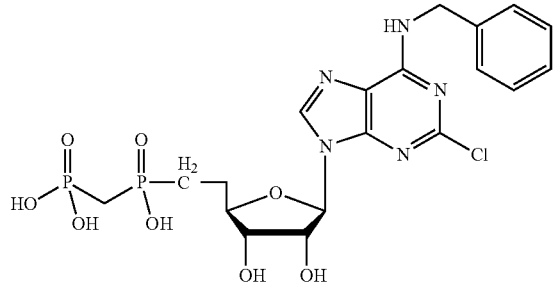

,

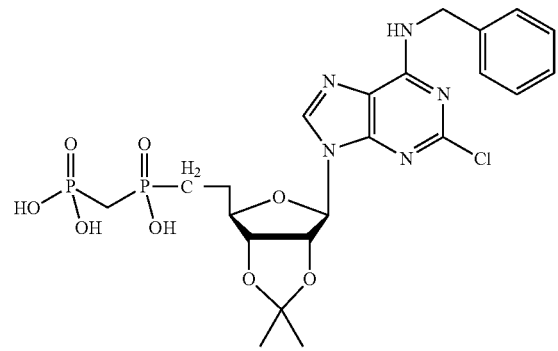

,

-continued
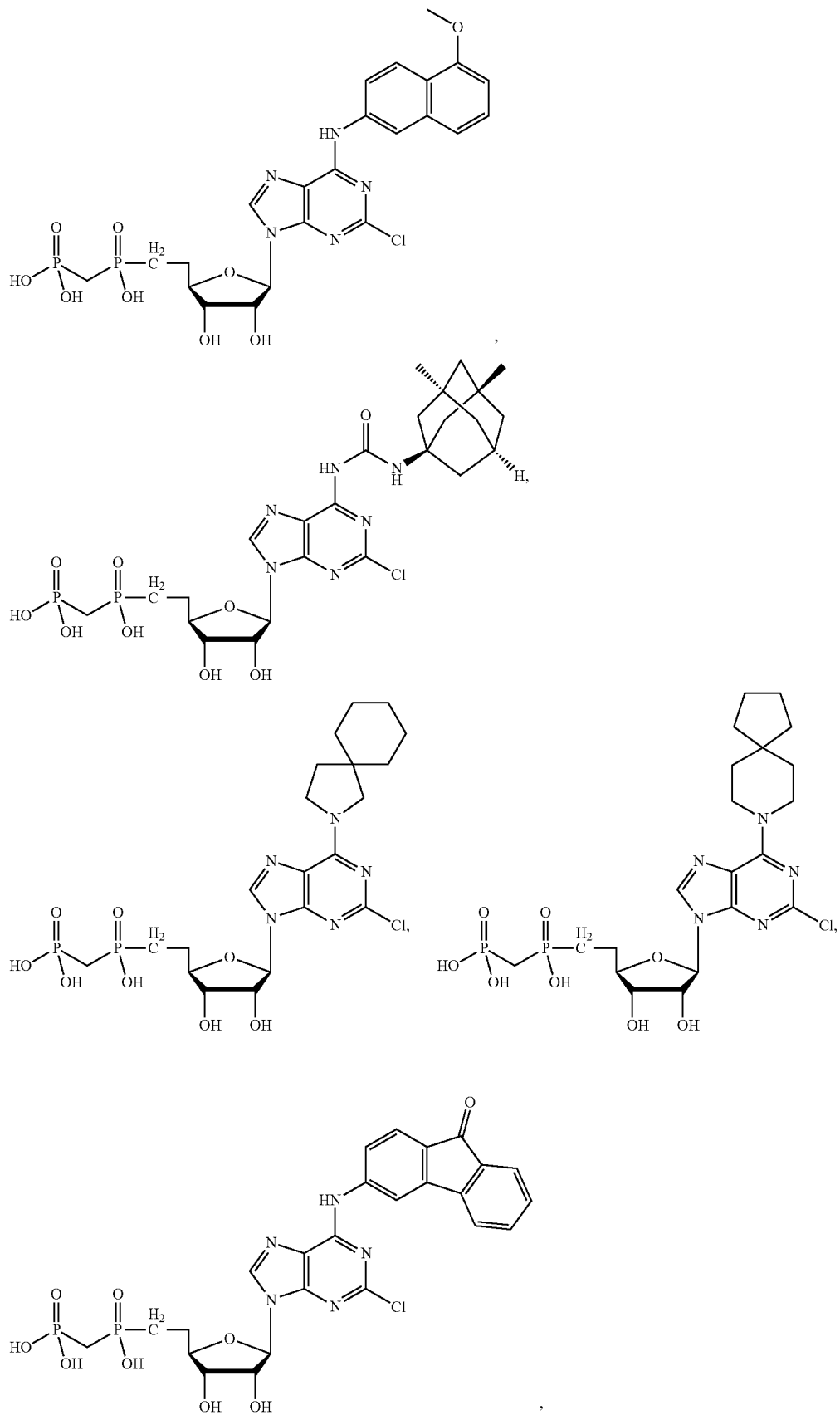

195 196
-continued
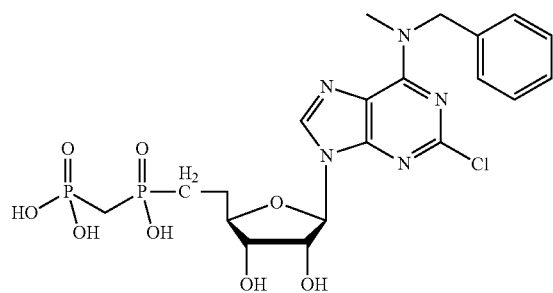
,
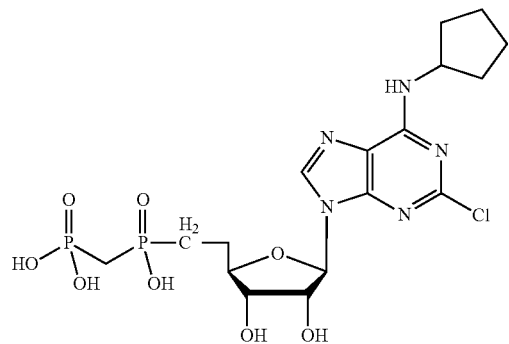
,
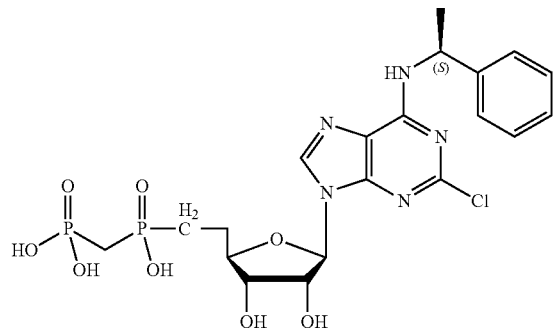
,
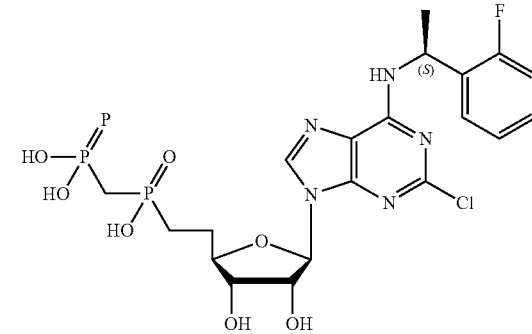
,
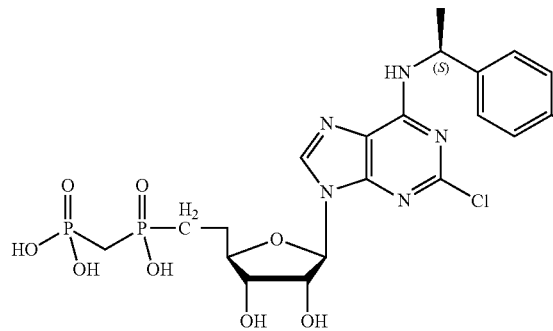
,
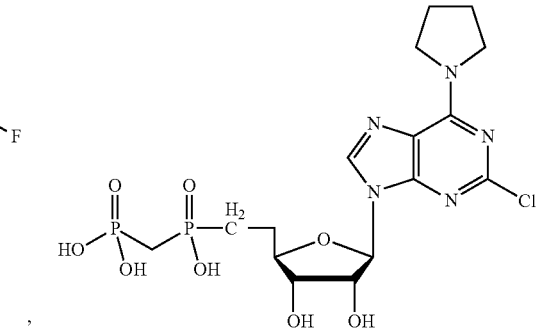
,
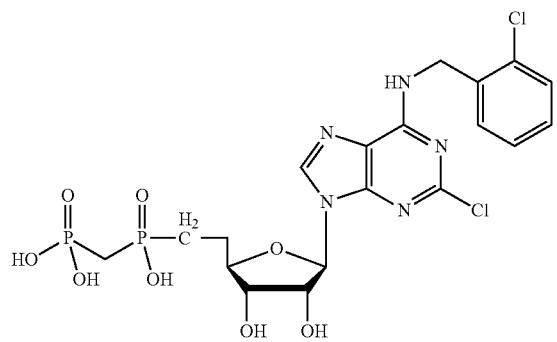
,
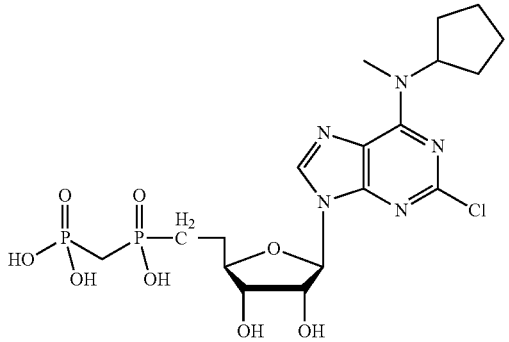
, 197 198
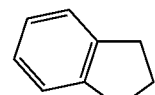
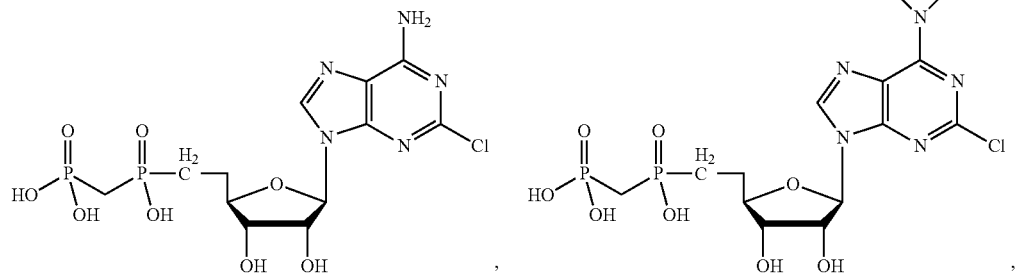
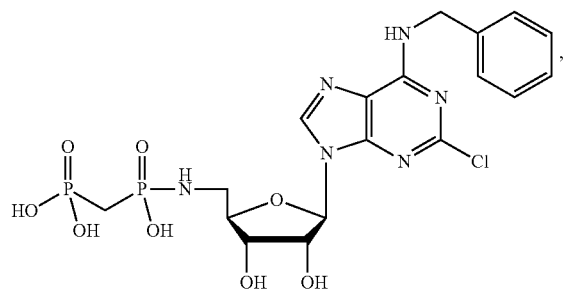
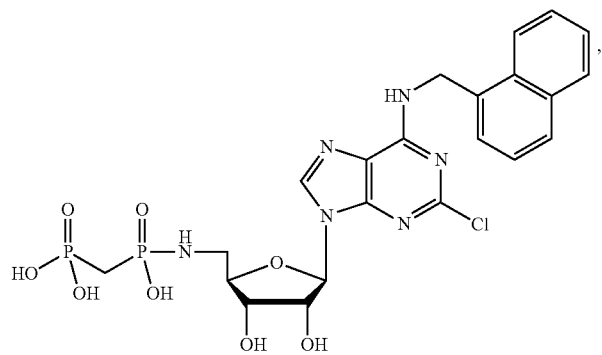
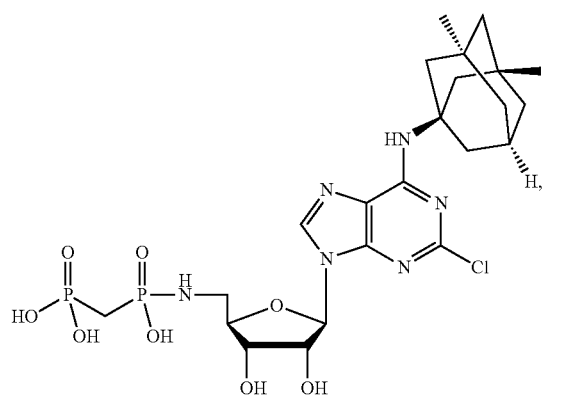

-continued
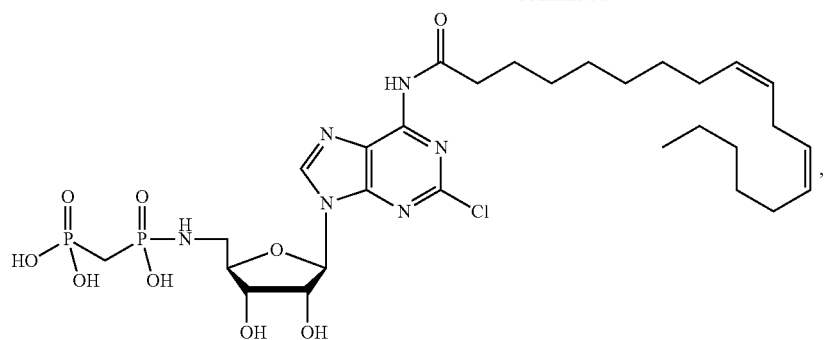
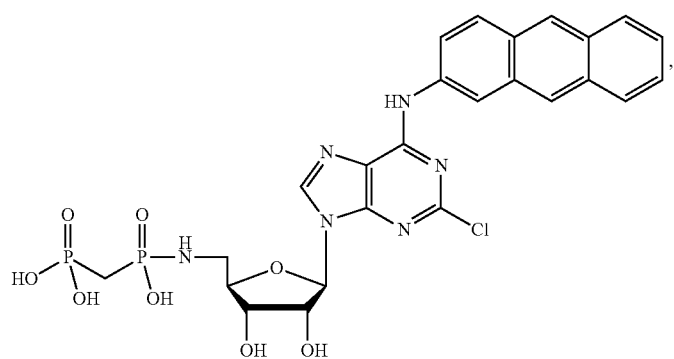
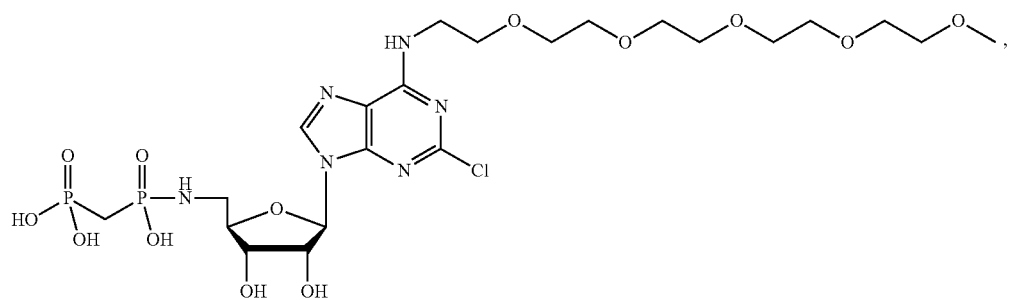
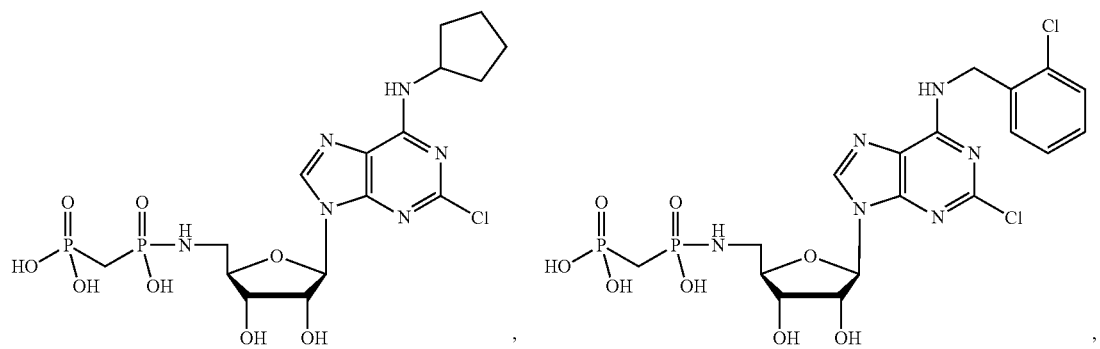

-continued
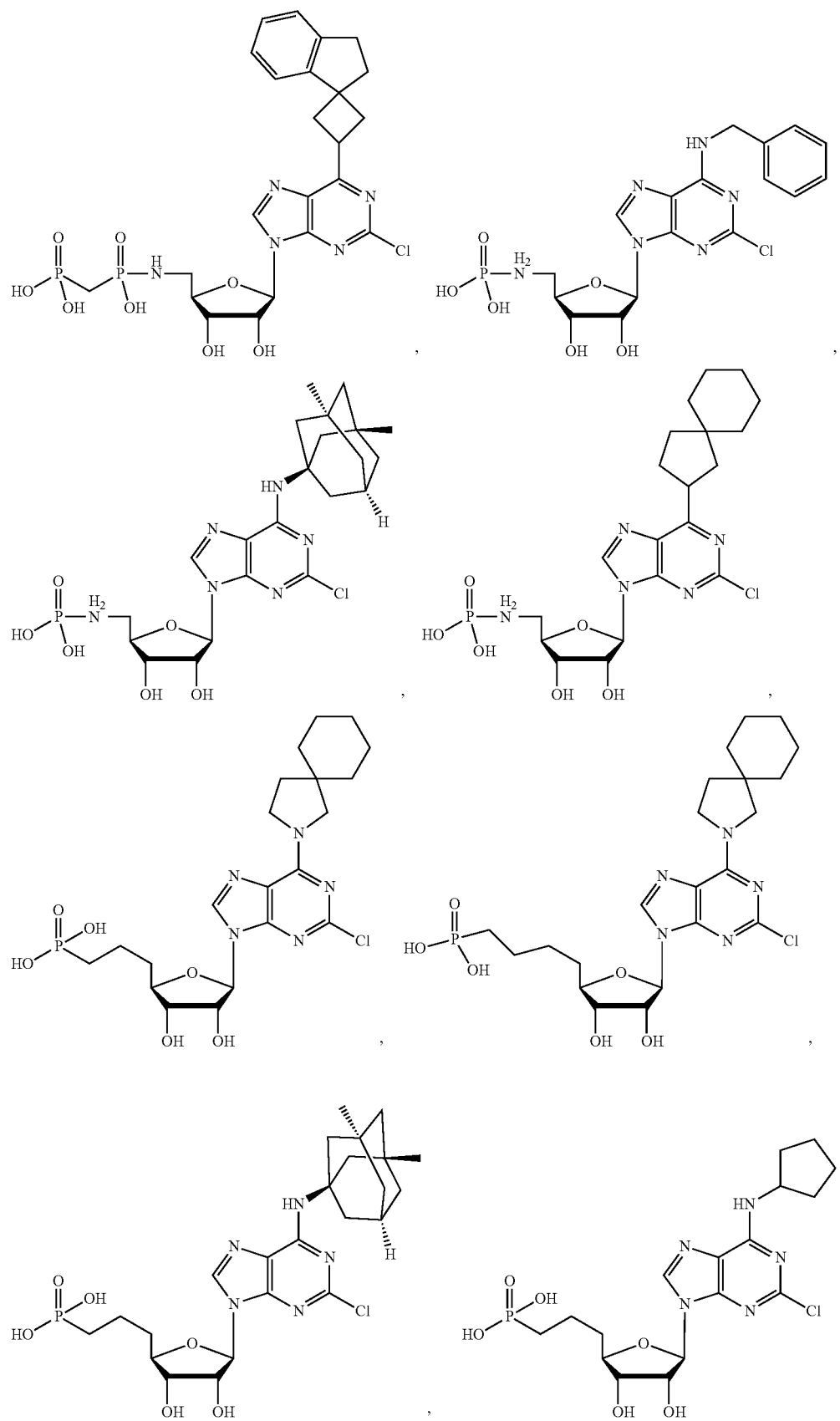

-continued
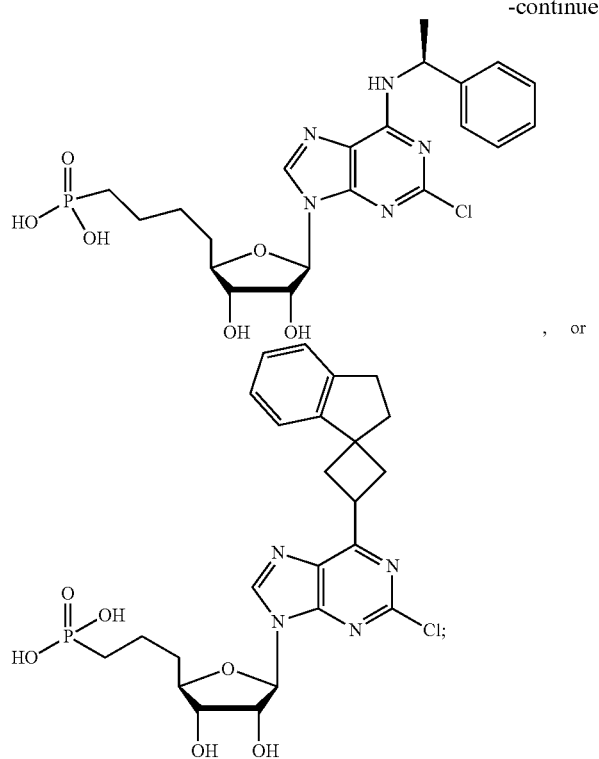
or a pharmaceutically acceptable salt or ester thereof.
* * * * *